US005683905A

United States Patent [19]

Capon et al.

[11] Patent Number: 5,683,905

[45] Date of Patent: Nov. 4, 1997

[54] VECTORS AND CELL LINES CAPABLE OF CORRECTLY SPLICING EXON REGIONS

[75] Inventors: Daniel J. Capon, San Mateo; Richard M. Lawn, San Francisco; Gordon A. Vehar, San Carlos; William L. Wood, San Mateo, all of Calif.

[73] Assignee: Genentech, Inc., South San Francisco, Calif.

[21] Appl. No.: 448,171

[22] Filed: May 23, 1995

Related U.S. Application Data

[63] Continuation of Ser. No. 595,481, Oct. 9, 1990, which is a continuation of Ser. No. 83,758, Aug. 7, 1987, Pat. No. 4,965,199, which is a continuation of Ser. No. 602,312, Apr. 20, 1984, abandoned.

[51] Int. Cl.$^6$ .............................. C12N 15/63; C12N 5/00
[52] U.S. Cl. ............................ 435/320.1; 435/240.1
[58] Field of Search .............................. 435/320.1, 240.1

[56] References Cited

U.S. PATENT DOCUMENTS

| | | | |
|---|---|---|---|
| Re. 32,011 | 10/1985 | Zimmerman et al. | 530/383 |
| 4,027,013 | 5/1977 | Bick et al. | 514/21 |
| 4,069,216 | 1/1978 | Shanbrom | 530/383 |
| 4,085,095 | 4/1978 | Bick et al. | 530/383 |
| 4,093,608 | 6/1978 | Iga et al. | 530/383 |
| 4,104,266 | 8/1978 | Wickerhauser | 530/383 |
| 4,188,318 | 2/1980 | Shanbrom | 530/383 |
| 4,221,780 | 9/1980 | Cort | 530/383 |
| 4,289,691 | 9/1981 | Rock | 530/383 |
| 4,294,826 | 10/1981 | Feldman | 530/383 |
| 4,341,764 | 7/1982 | Wallace et al. | 514/2 |
| 4,348,315 | 9/1982 | Blomback et al. | 530/383 |
| 4,359,463 | 11/1982 | Rock | 424/529 |
| 4,361,509 | 11/1982 | Zimmerman et al. | 530/383 |
| 4,387,092 | 6/1983 | Liautaud et al. | 530/383 |
| 4,396,601 | 8/1983 | Salser et al. | 424/94.5 |
| 4,399,216 | 8/1983 | Axel et al. | 435/6 |
| 4,404,131 | 9/1983 | Schwarz et al. | 530/383 |
| 4,495,175 | 1/1985 | Chavin et al. | 530/383 |
| 4,508,709 | 4/1985 | Amphlett et al. | 530/383 |
| 4,522,751 | 6/1985 | Linnau et al. | 530/383 |
| 4,556,558 | 12/1985 | Rubinstein | 530/383 |
| 4,614,795 | 9/1986 | Chavin et al. | 530/383 |
| 4,632,981 | 12/1986 | Bock et al. | 514/8 |
| 4,657,894 | 4/1987 | Zimmerman et al. | 514/21 |
| 4,659,805 | 4/1987 | Schilling, Jr. et al. | 530/350 |
| 4,757,006 | 7/1988 | Toole, Jr. et al. | 435/69.6 |
| 4,879,226 | 11/1989 | Wallace et al. | 435/68.1 |
| 4,965,199 | 10/1990 | Capon et al. | 435/69.6 |
| 5,004,804 | 4/1991 | Kuo et al. | 530/387.9 |
| 5,101,016 | 3/1992 | Zimmerman et al. | 530/383 |
| 5,252,475 | 10/1993 | Reth | 435/172.3 |
| 5,498,531 | 3/1996 | Jarrell | 435/91.31 |
| 5,561,053 | 10/1996 | Crowley | 435/69.1 |

FOREIGN PATENT DOCUMENTS

| | | |
|---|---|---|
| 123945 | 11/1984 | European Pat. Off. |
| 127603 | 12/1984 | European Pat. Off. |
| 150735 | 8/1985 | European Pat. Off. |
| 152746 | 8/1985 | European Pat. Off. |
| 157556 | 10/1985 | European Pat. Off. |
| 169562 | 1/1986 | European Pat. Off. |
| 182372 | 5/1986 | European Pat. Off. |
| 251843 | 1/1988 | European Pat. Off. |
| 253455 | 1/1988 | European Pat. Off. |
| 2172000 | 9/1986 | United Kingdom. |
| WO 84/00560 | 2/1984 | WIPO. |
| WO 85/01961 | 5/1985 | WIPO. |
| WO 86/06101 | 10/1986 | WIPO. |
| WO 86/06409 | 11/1986 | WIPO. |

OTHER PUBLICATIONS

Hamer et al. Splicing and the Formation of Stable RNA. Cell 18:1299–1302. 1979.
Okayama et al. A cDNA Cloning Vector that Permits Expression of cDNA Inserts in Mammalian Cells. Molecular and Cellular Biology 3(2):280–289. 1983.
*Nexis Report, Business Week* (Feb. 16, 1987).
*Biotechnology Law Report* 6:389–390 (Sep.–Oct. 1987).
*Nexis Report, Business Week* (Apr. 13, 1987).
*Nexis Report, Genetic Technology News* (Nov. 1987).
*Newswatch* 7(21):5–6 (Nov. 2, 1987).
*FDC Reports* 50(18):T&G–12 (May 2, 1988).
Monoclate R Product Disclosure.
Andersson et al., "Isolation and characterization of human factor VIII: molecular forms in commercial factor VIII concentrate, cryoprecipitate, and plasma" *Proc. Natl. Acad. Sci. USA* 83 (9):2979–2983 (1986).
Beck et al., "Nucleotide sequence and exact localization of the neomycin phosphotransferase gene from transposon Tn5" *Gene* 19(3):327–336 (1982).
Brownlee and Rizza, "Clotting factor VIII cloned" *Nature* 312 (5992):307 (1984).
Choo et al., "Vectors for expression and amplification of cDNA in mammalian cells: expression of rat phenylalanine hydroxylase" *DNA* 5(6):529–537 (1986).
de Saint Vincent et al., "The cloning and reintroduction into animal cells of a functional CAD gene, a dominant amplifiable genetic marker" *Cell* 27(1):267–277 (Dec. 1981).
Eaton et al., "Proteolytic processing of human factor VIII. Correlation of specific cleavages by thrombin, factor Xa, and activated protein C with activation and inactivation of factor VIII coagulant activity" *Biochemistry* 25(2):505–512 (1986).
Fass et al., "Monoclonal antibodies to porcine factor VIII coagulant and their use in the isolation of active coagulant protein" *Blood* 59(3):594–600 (1982).

(List continued on next page.)

*Primary Examiner*—Douglas W. Robinson
*Assistant Examiner*—Thanda Wai
*Attorney, Agent, or Firm*—Janet E. Hasak; Janet M. McNicholas

[57] ABSTRACT

A recombinant DNA vector is provided that expresses exons of genomic DNA fragments that are inserted into the vector. The vector contains a promoter and a genomic DNA fragment so characterized and configured that the vector, upon transcription in a transfected eukaryotic cell culture, expresses the corresponding RNA segment of the genomic DNA fragment free of any intron.

6 Claims, 32 Drawing Sheets

OTHER PUBLICATIONS

Fay et al., "The effect of carbohydrate depletion on procoagulant activity and in vivo survival of highly purified human factor VIII" *Biochimica et Biophysica Acta* 800(2):152–158 (Jul. 1984).

Fay et al., "Propolypeptide of von Willebrand factor circulates in blood and is identical to von Willebrand antigen II" *Science* 232:995–998 (May 1986).

Fay et al., "Purification and characterization of a highly purified human factor VIII consisting of a single type of polypeptide chain" *Proc. Natl. Acad. Sci. USA* 79 (23):7200–7204 (Dec. 1982).

Fay et al., "The size of human factor VIII heterodimers and the effects produced by thrombin" *Biochimica et Biophysica Acta* 871 (3):268–278 (Jun. 1986).

Fulcher & Zimmerman, "Characterization of the human factor VIII procoagulant protein with a heterologous precipitating antibody" *Proc. Natl. Acad. Sci. USA* 79 (5):1648–1652 (Mar. 1982).

Giri et al., "Comparative studies of the expression of linked *Escherichia coli* gpt gene and BPV–1 DNAs in transfected cells" *Virology* 127 (2):385–396 (Jun. 1983).

Gitschier et al., "Characterization of the human factor VIII gene" *Nature* 312:326–330 (Nov. 1984).

Haber et al., "Chromosome–Mediated Transfer and Amplification of an Altered Mouse Dihydrofolate Reductase Gene" *Somatic Cell Genetics* 8 (4):499–508 (1982).

Harris, "Isolation and characterization of low molecular weight non–aggregated antihemophelic factor from fresh human plasma" (Dissertation Abstract) (1979).

Hoyer and Trabold, "The effect of thrombin on human factor VIII" *J. Laboratory and clin. Med.* 97 (1):50–64 (1981).

Kaufman, "Construction of a Modular Dyhydrofolate Reductase cDNA Gene: Analysis of Signals Utilized for Efficient Expression" *Molecular & Cellular Biology* 2 (11):1304–1319 (1982).

Kaufman et al., "Amplification and Expression of Sequences Cotransfected with a Modular Dihydrofolate Reductase Complementary DNA Gene" *J. Mol. Biol.* 159:601–621 (1992).

Kaufman et al., "Selection and amplification of heterologous genes encoding adenosine deaminase in mammalian cells" *Proc. Natl. Acad. Sci. USA* 83 (10):3136–3140 (May 1986).

Kaufman et al., "Site–specific mutagenesis to study the structure and function of factor VIII" *Journal of Cellular Biochemistry Supplement* (UCLA Symposia on Molecular & Cellular Biology, Jan. 20, 1986–Feb. 15, 1986), New York:Alan R. Liss, Inc. vol. 10A:275 (1986).

Kemp et al., "Stable mutants of mammalian cells that overproduce the first three enzymes of pyrimidine nucleotide biosynthesis" *Cell* 9 (4):541–550 (Dec. 1976).

Knutson and Fass, "Porcine factor VIII:C prepared by affinity interaction with von Willebrand factor and heterologous antibodies: sodium dodecyl sulfate polyacrylamide gel analysis" *Blood* 59 (3):615–624 (1982).

Legaz et al., "Isolation and characterization of human Factor VIII (antihemophilic factor)" *Journal of Biological Chemistry* 248 (11):3946–3955 (Jun. 1973).

Maddox, "Who will clone a chromosome?" *Nature* 312 (22):306 (1984).

McConlogue et al., "Molecular cloning and expression of the mouse ornithine decarboxylase gene" *Proc. Natl. Acad. Sci. USA* 81 (2):540–544 (Jan. 1984).

Milbrandt et al., "Amplification of a cloned Chinese hamster dihydrofolate reductase gene after transfer into a dihydrofolate reductase–deficient cell line" *Molecular & Cellular Biology* 3 (7):1274–1282 (Jul. 1983).

Murray et al., "Construction and use of a dominant, selectable marker: a Harvey sarcoma virus–dihydrofolate reductase chimera" *Molecular & Cellular Biology* 3 (1):32–43 (Jan. 1983).

Norris et al., "Efficient site–directed mutagenesis by simultaneous use of two primers" *Nucleic Acids Research* 11 (15):5103–5112 (1983).

Orr et al., *Thrombosis Haemostasis* 54 (1):54 (1985).

Ringold et al., "Co–expression and Amplification of Dihydrofolate Reductase cDNA and the *Escherichia coli* XGPRT Gene in Chinese Hamster Ovary Cells" *Journal of Molecular & Applied Genetics* 1 (3):165–175 (1981).

Schoner and Littlefield, "The organization of the dihydrofolate reductase gene of baby hamster kidney fibroblasts" *Nucleic Acids Research* 9 (23):6601–6614 (1981).

Simonsen and Levinson, "Isolation and expression of an altered mouse dihydrofolate reductase cDNa" *Proc. Natl. Acad. Sci. USA* 80 (9):2495–2499 (1983).

Stel et al., "Detection of factor VIII coagulant antigen in human liver tissue" *Nature* (Abstract only) 303:530–532 (1983).

Toole et al., "A large region (approximately equal to 95 kDa) of human factor VIII is dispensable for in vitro procoagulant activity" *Proc. Natl. Acad. Sci. USA* 83 (16):5939–5942 (Aug. 1986).

Toole et al., "Molecular cloning of a cDNA encoding human antihaemophilic factor" *Nature* 312:342–347 (1984).

Vehar and Davie, "Preparation and properties of bovine factor VIII (antihemophilic factor)" *Biochemistry* 19 (3):401–410 (1980).

Vehar et al., "Structure of human factor VIII" *Nature* 312:337–342 (1984).

Wahl, et al., "Effect of chromosomal position on amplification of transfected genes in animal cells" *Nature* 307:516–520 (1984).

Weinstein et al., "Apparent molecular weight of purified human factor VIII procoagulant protein compared with purified and plasma factor VIII procoagulant protein antigen" *Blood* 62 (5):1114–1117 (Nov. 1983).

Wigler et al., "Transformation of mammalian cells with an amplifiable dominant–acting gene" *Proc. Natl. Acad. Sci. USA* 77 (6):3567–3570 (1980).

Wigler et al., "Transformation of Mammalian Cells with Genes from Procaryotes and Eucaryotes" *Cell* 16:777–785 (1979).

Wood et al., "Expression of active human factor VIII from recombinant DNA clones" *Nature* 312:330–337 (1984).

Zimmerman et al. *Haemostasis and Thrombosis*, Bloom et al., ed. p. 111 (1981).

SURFACE-MEDIATED ACTIVATION OF BLOOD COAGULATION
(INTRINSIC SYSTEM)

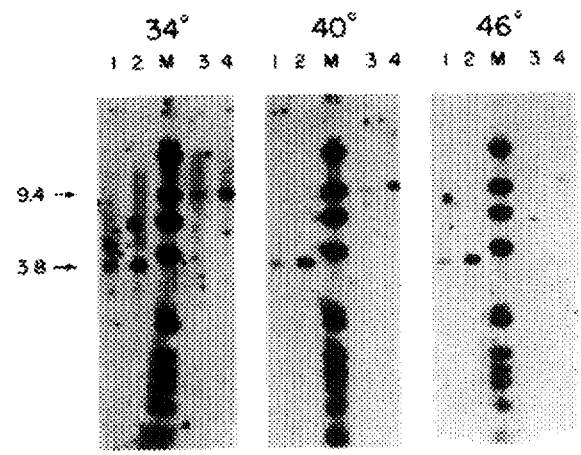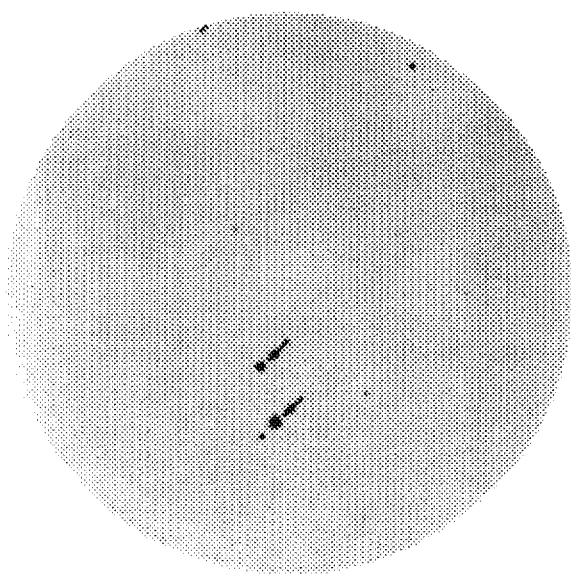
FIG.3A  FIG.3B  FIG.3C  FIG.3D

SEQUENCE OF pESVDA.S127 cDNA

```
         sacI   VECTOR│EXON C
    1    GAGCTCGCCCC CTGTTGGGGG CTCAGAGTGG CAGTGTCCCT CAGTTCAAGA AGTTGTTTT CCAGGAATTT ACTGATGGCT CCTTTACTCA GCCCTTATAC
                                                                                    C│EXON A (minus 47 b)
  101    CGTGGAGAAC TAAATGAACA TTTGGGACTC CTGGGGCCAT ATATAAGAGC AGAAGTTGAA GATAATATCA TGCCTTATTT CTTATGAGGA AGATCAGAGG
                                                                                              ndeI
  201    CAAGGAGCAG AACCTAGAAA AAACTTTGTC AAGCCTAATG AAACCAAAAC TTACTTTTGG AAAGTGCAAC ATCATATGGC ACCCACTAAA GATGAGTTTG
                                              A│EXON D                     stuI
  301    ACTGCAAAGC CTGGCCTTAT TTCTCTGATG TTGACCTGGA AAAAGATGTG CACTCAGGCC TGATTGGACC CCTTCTGGTC TGCCACACTA ACACTACCTG
                                                                hincII
  401    CCCTGCTCAT GGGAGACAAG TGACAGTACA GGAATTTGCT CTGTTTTCA CCATCTTTGA TGAGACCAAA AGCTGGTACT TCACTGAAAA TATGGAAAGA
               pstI                                     ahaII                                          D│EXON E
  501    AACTGCAGGG CTCCCCTCGAA TATCCAGATG GAAGATCCCA CTTTTAAAGA GAATTATCGC TTCCATGCAA TCAATGGCTA CATAATGGAT ACACTACCTG
  601    GCTTAGTAAT GGCTCAGGAT CAAAGGATTC GATGGTATCT GCTCAGCATG GGCAGCAATG AAACATCCA TTCTATTCAT TTCAGTGGAC ATGTGTTCAC
                                                                 E│EXON I
  701    TGTACGAAAA AAAGAGGAGT ATAAAATGGC ACTGTACAAT CTCTATATCC AG GTGGATCTGT TGGCACCAAT GATTATTCAC GGCATCAAGA CCCAGGGTGC
  801    CCGTCAGAAG TTCTCCAGCC TCTACATCTC TCAGTTTATC ATCATGTATA GTCTTGATGG GAAGAAGTGG CAGACTTATC GAGGAAATTC CACTGGAACC
               I│VECTOR                                                          sacI
  901    TTAATGCAGC CGCCGCCATG AGCGCCAACT CGTTTGATGG AAGCATTGTG AGCTC
```

```
-109  CTTTCATTAAATCAGAAATTTACTTTTTTCCCCTCCTGGGAGCTAAAGATATTTTAGAGAAGAATTAACCTTTTGCTTCTCCAGTTGAACATTTGTAGCAATAAGTC
                                                                                                        S1
                                                                                                        met gln
                                                                                                        ATG CAA
           sacI                                 S19    1                                          10
       ile glu leu ser thr cys phe leu arg phe cys ser ala thr arg arg tyr tyr leu gly ala val glu leu ser
  7    ATA GAG CTC TCC ACC TGC TTC CTG CGA TTC TGC AGT GCC ACC AGA AGA TAC TAC CTG GGT GCA GTG GAA CTG TCA
                                S10                           20                                  40
       trp asp tyr met gln ser asp leu gly glu leu pro arg val pro lys ser phe pro trp met gly phe pro asn thr ser
  97   TGG GAC TAT ATG CAA AGT GAT CTC GGT GAG CTG CCT AGA GTG CCA AAA TCT TTT CCA TGG ATG GGT TTC CCA AAC ACC TCA
                                            ecoRI                             50                              70
       val val tyr lys lys thr leu phe val glu phe thr asp his leu phe asn ile ala lys pro arg pro trp met gly leu leu gly
 187   GTC GTG TAC AAA AAG ACT CTG TTT GTA GAA TTC ACG GAT CAC CTT TTC AAC ATC GCT AAG CCA AGG CCA TGG ATG GGT CTA GGT
                                                            80                                100
       pro thr ile gln ala glu val tyr asp thr val val ile thr leu lys asn met ala ser his pro val ser leu his ala val gly val
 277   CCT ACC ATC CAG GCT GAG GTT TAT GAT ACA GTG GTC ATT ACA CTT AAG AAC ATG GCT TCC CAT CCT GTC AGT CTT CAT GCT GTT GGT GTA
                   hindIII                110                             120                              130
       ser tyr trp lys ala ser leu asn ser gln thr ser gln arg glu lys glu asp asp lys val phe pro gly gly ser
 367   TCC TAC TGG AAA GCT TCT CTG AAT AGC CAG ACC AGT CAA AGG GAG AAA GAA GAT GAT AAA GTC TTC CCT GGT GGA AGC
                                            140                                   150                          160
       his thr ile gln val leu lys glu asn gly ile ala ser asp pro leu cys ser arg glu thr tyr ser leu ser his val asp
 457   CAT ACA ATC CAG GTC CTG AAA GAG AAT GGA ATT GCC TCT GAC CCA CTG TGT AGT AGA GAA ACA TAC TCA TCT CAT GTG GAC
                              ecoRI   170                                 180                           190
       leu val lys asp leu asn ser gly leu val phe asp gly lys lys arg glu glu gly gly ser leu ala lys lys thr gln thr leu his
 547   CTG GTA AAA GAC TTG AAT TCA GGC CTC GTA TTT GAT GGA AAG AAG AGA GAA GGG AGT CTG GCC AAG AAG ACA CAG ACC TTG CAC
                                             200                               210                              220
       lys phe ile leu phe ala val phe asp gly lys ser glu thr lys ser leu asn ser met gln asp arg asp ala ala
 637   AAA TTT ATA CTA CTT TTT GCT GTA TTT GAT GGA AAG AGT GAA ACA AAG TCC TTG ATG CAG GAT AGG GAT GCT GCA
                                          230                              240                           250
       ser ala arg ala trp pro lys met his thr val asn arg ser leu pro gly leu ile gly cys his arg lys ser val
 727   TCT GCT CGG GCC TGG CCT AAA ATG CAC ACA GTC AAC AGG TCT CTG CCA GGT CTG ATT GGA TGC CAC AGG AAA TCA GTC
```

FIG. 10A-2

```
       tyr trp his val ile gly met gly thr thr pro glu val his ser ile gly his thr phe leu val arg asn his arg gln
                                260                     270                     280
 817   TAT TGG CAT GTG ATT GGC ATG GGC ACC ACT CCT GAA GTG CAC TCA ATA TTC GGT CAC ACA TTT CTT GTG AAC CAT CGC CAG ala ser leu glu ile ser pro ile thr ala gln thr leu thr phe leu gly gln phe leu leu phe cys his ile ser
                                290                     300                     310
 907   GCG TCC TTG GAA ATC TCG CCA ATA ACT GCT CAA ACA CTC CTT CTA GGA CAG TTT CTA CTG TGT CAT ATC TCT ser his gln his asp gly met glu ala tyr val lys val asp ser cys pro gln leu arg met lys asn asn glu glu ala
                 320 hindIII     330                     340
 997   TCC CAC CAA CAT GAT GGC ATG GAA GCT TAT GTC AAA GTA GAC AGC TGT CCA CAA CTA CGA ATG AAA AAT AAT GAA GAA GCG glu asp tyr asp asp asp leu thr asp ser glu met asp val val arg phe ile gln ser pro ser phe ile gln ile arg ser
                                350                     360                     370
1087   GAA GAC TAT GAT GAT GAT CTT ACT GAT TCT GAA ATG GAT GTG GTG AGG TTT ATC CAA TCT CCT TCC TTT ATC CAA ATT CGC TCA val ala lys lys his pro lys thr trp val his tyr ile ala ala glu glu asp trp asp lys lys val lys tyr gly pro leu val leu ala pro asp
                                380                     390                     400
1177   GTT GCC AAG AAG CAT CCT AAA ACT TGG GTA CAT TAT ATT GCT GCT GAA GAG GAC TGG GAC AAA AAG GTC AAA TAT GGG CCC CTA GTC GCC CCC GAT asp arg ser tyr lys ser gln gln arg pro tyr asn ile gly pro gln arg ile thr arg lys val arg phe met ala tyr thr asp
                                410                     420                     430
1267   GAC AGA AGT TAT AAA AGT CAA CAA AGG CCA TAT AAC ATC GGC CCT CAG CGG ATT ACT AGG AAG GTC CGA TTT ATG GCA TAC ACA GAT glu thr phe lys thr arg glu ala ile gln his leu glu ser gly ile leu leu gly pro leu leu tyr gly val glu val thr leu leu ile
                                440                     450                     460
1357   GAA ACC TTT AAG ACT CGT GAA GCT CAG CAT TTG GAA TCA GGA ATC TTG CTT GGA CCT CTT TTA TAT GGG GAA GTT ACA CTG TTG ATT ile phe lys asn gln ala ser arg pro pro tyr asn ile tyr pro his gly ile thr asp val arg pro leu tyr ser arg arg leu pro lys
                                470                     480                     490
1447   ATA TTT AAG AAT CAA GCA AGC AGA CCA CCT TAC AAC ATC TAC CCT CAC GGA ATC ACT GAT GTC CGT CCT TTG TAT TCA AGG AGA TTA CCA AAA gly val lys his leu lys asp phe pro ile leu pro gly glu ile phe lys tyr lys trp thr val thr val glu asp gly pro thr lys
                                500                     510                     520
1537   GGT GTA AAA CAT TTG AAG GAT TTT CCA ATT CTG CCA GGA GAA ATA TTC AAA TAT AAA TGG ACA GTG ACT GTA GAA GAT GGG CCA ACT AAA ser asp pro arg cys leu thr arg tyr tyr ser ser phe val asn met glu arg asp leu ala ser gly leu ile gly pro leu leu ile
                                530                     540                     550
1627   TCA GAT CCT CGG TGC CTG ACC CGC TAT TAC TCT AGT TTC GTT AAT ATG GAG AGA GAT CTA GCT TCA GGA CTC ATT GGC CCT CTC CTC ATC
```

FIG.10A-3

```
                      560                          570                               580
      cys tyr lys glu ser val asp gln arg gly asn gln ile met ser asp lys arg asn val ile leu phe ser val phe asp glu asn arg
1717  TGC TAC AAA GAA TCT GTA GAT CAA AGA GGA AAC CAG ATA ATG TCA GAC AAG AGG AAT GTC ATC CTG TTT TCT GTA TTT GAT GAG AAC CGA
      kpnI                                                                                             bamHI
                      590                          600                               610
      ser trp tyr leu thr glu ile gln arg phe leu pro asn pro ala gly val gln leu glu asp pro glu phe gln ala ser asn ile
1807  AGC TGG TAC CTC ACA GAG ATA CAA CGC TTT CTC CCC AAT CCA GCT GGA GTG CAG CTT GAG GAT CCA GAG TTC CAA GCC TCC AAC ATC
                      620                          630                               640
      met his ser ile asn gly tyr val phe asp ser leu gln leu ser val cys leu his glu val ala tyr trp tyr ile leu ser ile gly
1897  ATG CAC AGC ATC AAT GGC TAT GTT TTT GAT AGT TTG CAG TTG TCA GTT TGT TTG CAT GAG GTG GCA TAC TGG TAC ATT CTA AGC ATT GGA
                      650                          660                               670
      ala gln thr asp phe leu ser val phe ser phe lys met val tyr glu asp thr leu thr phe arg asn ser phe arg gly met thr
1987  GCA CAG ACT GAC TTC CTT TCT GTC TTC TCA GTT TTT AAA ATG GTC TAT GAA GAC ACA CTC ACC TTC AGA AAC TCA TTC CGG AGA GGC ATG ACC
                      680                          690                               700
      ser gly glu thr val phe met ser met glu asn pro gly cys his asn ser asp ile ser ala tyr leu ser lys
2077  TCA GGA GAA ACT GTC TTC ATG TCG ATG GAA AAC CCA GGT TGC CAC AAC TCA GAT ATT TCA GCA TAC TTG AGT AAA
                      710                          720                               730
      ala leu leu lys val ser ser cys asp lys ser asn thr gly leu asp ser tyr tyr glu asp ile ser ala tyr leu ser lys
2167  GCC TTA CTG AAG GTT TCT AGT TGT GAC AAG AGC AAT ACT GGT GAT TAT TAC GAA GAT ATT TCA GCA TAC TTG AGT
                      hindIII                      ecoRI                             760
      asn asn ala ile glu pro ser phe ser gln asn asn ser arg his pro met pro lys gln phe asn ala thr ile pro glu
2257  AAC AAT GCC ATT GAA CCA AGC TTC TCC CAG AAT AAT TCA AGA CAC CCT ATG CCT AAA CAA TTT AAT GCC ACA ATT CCA GAA
                      770                          780                               790
      asn asp ile glu lys thr asp pro trp phe ala his arg thr pro met pro lys gln ala lys tyr glu thr phe ser asp asp leu met leu
2347  AAT GAC ATA GAG AAG ACT GAC CCT TGG TTT GCA CAC AGA ACA CCT ATG CCT AAA CAA GCC AAA TAT GAG ACT TTT TCT GAT GAT TTG ATG CTC
                      800                          810                               820
      leu arg gln ser pro thr pro his gly leu leu ser leu gln glu ala lys tyr glu ala lys tyr glu thr phe ser asp asp pro gly
2437  TTG CGA CAG AGT CCT ACT CCA CAT GGG CTA TCC TTA CTC GAA GCC AAA GCC CCA TCA CCT GGA
                      830                          840                               850
      ala ile asp ser asn asn ser leu met thr his phe arg pro gln leu his his ser gly asp met val phe thr pro glu ser
2527  GCA ATA GAC AGT AAT AAC AGC CTG GAA ATG ACA CAC TTC AGG CCA CAG CTC CAT CAC AGT GGG GAC ATG GTA TTT ACC CCT GAG TCA
```

FIG. 10B-1

```
                    860                         870                         880
       gly leu gln leu arg leu asn glu lys leu gly thr ala ala thr glu leu lys lys leu asp phe lys val ser ser thr ser asn
2617   GGC CTC CAA TTA AGA TTA AAT GAG AAA CTG GGG ACA ACT GCA GCA ACA GAG TTG AAG AAA CTT GAT TTC AAA GTT TCT AGT ACA TCA AAT 890                         900                         910
       asn leu ile ser thr ile pro ser asp asn leu ala ala gly thr asp asn thr thr ser ser pro pro met pro val his tyr
2707   AAT CTG ATT TCA ACA ATT CCA TCA GAC AAT TTG GCA GCA GGT ACT GAT AAT ACA AGT TCC CCA CCC ATG CCA GTT CAT TAT 920                         930                         940
       asp ser gln leu asp thr leu phe gly lys lys ser ser gln glu ser thr leu gly gly pro leu ser leu ser glu asn asn
2797   GAT AGT CAA TTA GAT ACC ACT CTA TTT GGC AAA AAG TCA TCT CCC CTT GAG TCT ACT CTG GGA CCT CTG AGC TTG AGT GAA AAT AAT 950                         960                         970
       asp ser lys leu leu glu ser gly leu met asn ser gln glu ser ser trp gly lys asn val ser ser thr glu ser gly arg leu phe
2887   GAT TCA AAG TTG TTA GAA TCA GGT TTA ATG AAT AGC CAA GAA AGT TCA TGG GGA AAA AAT GTA TCG TCA ACA GAG AGT GGT AGG TTA TTT sacI    980                         990                         1000
       lys gly lys arg ala his gly pro ala leu leu thr val ser ile ser leu leu lys thr asn lys thr
2977   AAA GGG AAA AGA GCT CAT GGA CCT GCT TTG CTT ACT GTT AGC ATC TCT TTG TTA AAG ACA AAC AAA ACT 1010                        1020                        1030
       ser asn asn ser ala thr asn arg lys arg lys leu phe his ile asp gly pro ser val trp gln asn ile leu
3067   TCC AAT AAT TCA GCA ACT AAT AGA AAG AGG AAG CTT TTC CAC ATT GAT GGC CCA CCA TCA GTC TGG CAA AAT ATA TTA 1040                        1050                        1060
       glu ser asp thr glu phe lys val thr lys lys val pro leu ile his asp arg met leu met asp lys asn ala leu arg leu asn his
3157   GAA AGT GAC ACT GAG TTT AAA GTG ACA CCT TTG ATT CAT GAC AGA ATG CTT ATG GAC AAA AAT GCT ACA GCT TTG AGG CTA AAT CAT 1070                        1080                        1090
       met ser asn lys thr ser ser asn met glu met val gln arg thr arg trp gln lys lys gly pro ile pro pro asp ala gln asn pro asp
3247   ATG TCA AAT AAA ACT TCA TCA AAC ATG GAA ATG GTC CAA AGG ACT AGG TGG CAA AAG AAA GGG CCC ATT CCA CCA GAT GCA CAA AAT CCA GAT 1100                        1110                        1120
       met ser phe phe lys pro met leu phe leu pro glu ser ala arg trp ile gln arg thr his gly lys asn ser leu asn ser gly gln gly
3337   ATG TCG TTC TTT AAG CCT ATG CTA TTC TTG CCA GAA TCA GCA AGG TGG ATA CAA AGG ACT CAT GGA AAG AAC TCT CTG AAC TCT GGG CAA GGC 1130                        1140                        1150
       pro ser pro lys gln leu val ser leu gly pro glu lys gly gln asn phe leu ser glu lys asn phe val val gly
3427   CCC AGT CCA AAG CAA TTA GTA TCC TTA GGA CCA GAA AAG GGT CAG AAT TTC TTG TCT GAG AAA AAC TTC GTA GTG GGA
```

FIG. 10B-2

```
                              1160                    1170                    1180
         lys gly phe thr lys asp val gly leu lys lys ile gln glu met val phe pro ser arg asn leu phe leu thr asn leu asp asn leu his
3517     AAG GGT GAA TTT ACA AAG GAC GTA GGA CTC AAA AAA ATT CAG GAA ATG GTT TTT CCA AGC AGA AAC CTA TTT CTT ACT AAC TTG GAT AAT TTA CAT 1190                    1200                    1210
         glu asn asn thr his asn gln ile glu lys lys ile gln glu glu ile gln lys glu thr leu ile gln asn val glu val leu pro gln
3607     GAA AAT AAT ACA CAC AAT CAG GAA AAA ATT CAG GAA GAA ATA CAA GAG AAT ACA TTA ATC CAA AAT GTA GAA GTT TTG CCT CAG 1220                    1230                    1240
         ile his thr val thr gly thr lys asn phe met lys asn leu phe met lys asn val glu gly ser asp tyr asp gly ala
3697     ATA CAT ACA GTG ACT GGC ACT AAG AAT TTC ATG AAG AAC CTT TTC ATG AAG AAT GTA GAA GGT TCA GAC TAT GAC GGG GCA
         scaI 1250                    1260                    1270
         tyr ala pro val leu gln asp phe arg ser leu asn asp ser lys gln thr lys his thr lys lys lys thr arg asn thr ser gln
3787     TAT GCT CCA GTA CTT CAA GAT TTT AGG TCA TTA AAT GAT TCA AAG CAA ACC AAA CAC ACA AAA AAA AAA ACA AGC CAG 1280                    1290                    1300
         glu glu asn leu gly leu gly asn ile lys gln phe arg ala cys thr arg ile ser glu pro asn arg ile ile val
3877     GAA GAA AAC TTG GGA CTT GGA AAT ATT AAA CAG TTC AGG GCT TGC ACA AGG ATA TCT GAA CCT AAT AGG ATA GTG
                                          sphI 1310                    1320                    1330
         gln asn phe val thr val lys arg ser lys arg ala leu leu pro leu arg leu glu thr lys arg ile ser arg ile ile val gly
3967     CAG AAT TTT GTC ACG GTC AAA CGT AGT AAG AGA GCT TTG TTA CCA CTC AGA CTC GAA ACA CTT GAA AGG ATA AGG ATT GTG 1340                    1350                    1360
         asp asp thr ser thr gln trp ser lys asn met lys his thr pro ser thr leu thr gln ile asp tyr asn glu lys glu glu gly lys gly
4057     GAT GAC ACC TCA ACC CAG TGG TCC AAA AAC ATG AAA CAT ACC CCG AGC ACC CTC ACA CAG ATA GAC TAC AAT GAG AAG GAG AAA GGG 1370                    1380                    1390
         ala ile thr gln ser pro leu ser asp cys leu thr arg ser his ser ile pro gln ala asn ser pro leu ala lys val
4147     GCC ATT ACT CAG TCT CCC TTA TCA GAT TGC CTT ACG AGG AGT CAT AGC ATC CCT CAA GCA AAT AGT CCA TTA GCA AAG GTA 1400                    1410                    1420
         ser ser phe pro ser ile arg pro ile tyr leu thr arg val leu phe gln asp asn ser ser his leu pro ala ala ser tyr arg lys
4237     TCA TCA TTT CCA TCT ATT AGA CCT ATA TAT CTG ACC AGG GTC CTA TTC CAA GAC AAC TCT TCT CAT CTT CCA GCA GCA TCT TAT AGA AAG 1430                    1440                    1450
         lys asp ser gly val gln ser ser his phe leu gln gly ala lys lys asn asn leu asn leu ala ile leu thr leu glu met thr
4327     AAA GAT TCT GGG GTC CAA GAA AGC AGT CAT TTC TTA CAA GGA GCC AAA AAA AAT AAT CTT TCT CTA GCC ATT CTA ACC TTG GAG ATG ACT
```

FIG. 10B-3

```
                                                                                                              1480
      gly asp gln arg glu val gly ser leu gly thr ser ala thr asn ser val thr tyr lys val glu asn thr val leu pro lys pro
4417  GGT GAT CAA AGA GAG GTT GGC TCC CTG GGG ACA AGT GCC ACA AAT TCA GTC ACA TAC AAG GTT GAG AAC ACT GTT CTC CCG AAA CCA
                                                                        1500                                                          1510
      asp leu pro lys thr ala ser gly lys val glu leu leu pro lys his ile tyr gln lys asp phe pro thr ser asn gly
4507  GAC TTG CCC AAA ACA TCT GGC AAA GTT GAA TTG CTT CCA AAA GTT CAC ATT TAT CAG AAG GAC TTC CCT ACG AGC ACT GGG
                                                                        1530                                              1540
      ser pro gly his leu asp val gly ser leu leu gln gly thr gln gly ala ile lys trp asn glu ala asn arg pro gly lys
4597  TCT CCT GGC CAT CTG GAT GTG GAG AGC CTT CTT CAG GGA ACA CAG GGA GCG ATT AAG TGG AAT GAA GCA AAC AGA CCT GGA AAA
                                                                        1560 bamHI                                   1570
      val pro phe leu arg val ala thr glu ser ser ala lys thr pro ser lys leu leu asp pro leu ala trp asp thr asn his tyr gly thr
4687  GTT CCC TTT CTG AGA GTA GCA ACA GAA AGC TCT GCA AAG ACT CCC TCC AAG CTA TTG GAT CCT CTT GCT TGG GAT ACC CAC TAT GGT ACT
                                                                        1590                                              1600
      gln ile pro lys glu glu trp lys ser pro gln glu val ala ile asn glu thr lys lys asp thr ile leu ser leu asn ala
4777  CAG ATA CCA AAA GAA GAG TGG AAA TCC CAA GAG GTA GCA ATA AAT GAG ACA AAA AAG GAT ACC ATT TTG TCC CTG AAC GCT
                                                                        1620                                              1630
      cys glu ser asn his ala ile ala ala ile glu met lys lys val pro glu ile glu val thr arg ala lys gln gly leu gly thr glu
4867  TGT GAA AGC AAT CAT GCA ATA GCA GCA ATA GAG ATG AAG AAA GTC CCC GAA ATA GAA GTC ACC TGG GCA AAG CAA GGT AGG ACT GAA
                                                                        1650                                              1660
      arg leu cys ser gln asn pro val leu lys his gln arg thr leu glu arg leu gln ser asp pro arg ser phe gln lys
4957  AGG CTG TGC TCT CAA AAC CCA GTC TTG AAA CAT CAA CGG ACT CTT GAG CGC CTC CAG TCA GAT CCC AGC AGC TTT CAA AAG
                                                                        1680                                              1690
      tyr asp asp thr ile ser val glu met lys lys glu asp phe ile tyr asp tyr gly met ser ser ser pro his val leu arg asn arg ala gln
5047  TAT GAT GAT ACC ATA TCA GTT GAA ATG AAG AAG GAA GAT TTT ATT TAT GAT TAT GGG ATG AGT AGT TCC CCA CAT GTT CTA AGA AAC AGG GCT CAG
                                                                        1710                                              1720
      lys thr arg his tyr phe ile ala val glu arg leu trp asp tyr gly met ser ser ser pro his val leu arg asn arg ala gln lys
5137  AAA ACA CGA CAC TAT TTT GCT GCA GTG GAG AGG CTC TGG GAT TAT GGG ATG AGT AGT TCC CCA CAT GTT CTA AGA AAC AGG GCT CAG
                                                                        1740                                              1750
      ser gly ser val pro gln phe lys val val phe gln gln phe thr asp gly ser phe thr gln glu phe gln pro leu tyr arg gly glu leu asn
5227  AGT GGC AGT GTC CCT CAG TTC AAG GTT GTT TTC CAG CAG TTC ACT GAT GGC TCC TTT ACT CAG GAA TTT CAG CCC CTT TAC CGT GGA GAA CTA AAT
```

FIG.10C-1

```
                                                1760                            1770                            1780
      glu his leu gly leu gly pro tyr ile arg ala glu val glu asp asn ile met val thr phe arg asn gln ala ser arg pro tyr
5317  GAA CAT TTG GGA CTC GGG CCA TAT ATA AGA GCA GAA GTT GAA GAT AAT ATC ATG GTA ACT TTC AGA AAT CAG GCC TCJ CGT CCC TAT 1790                            1800                            1810
      ser phe tyr ser ser leu ile ser tyr glu asp gln gly ala glu pro arg lys asn phe val lys pro asn glu thr lys
5407  TCC TTC TAT TCT TCT CTT ATT TCT TAT GAG GAT CAG GGA GCA GAA CCT AGA AAA AAC TTT GTC AAG CCT AAT GAA ACC AAA 1820                            1830                            1840
      thr tyr phe trp lys val gln his his met ala pro thr lys asp glu phe asp cys lys ala trp ala tyr phe ser asp val asp leu
5497  ACT TAC TTT TGG AAA GTG CAA CAT CAT ATG GCA CCC ACT AAA GAT GAG TTT GAC TGC AAA GCC TGG GCT TAT TTC TCT GAT GTT GAC CTG 1850                            1860                            1870
      glu lys asp val his ser gly leu ile gly pro leu leu val cys his thr asn thr leu asn pro ala his gly arg gln val thr val
5587  GAA AAA GAT GTG CAC TCA GGC CTG ATT GGA CCC CTT CTG GTC CAC ACT AAC ACA CTG AAC CCT GCT CAT GGG AGA CAA GTG ACA GTA 1880                            1890                            1900
      gln glu phe ala leu phe phe thr ile phe asp glu thr lys ser trp tyr phe thr glu asn met glu arg asn cys arg ala pro cys
5677  CAG GAA TTT GCT CTG TTT TTC ACC ATC TTT GAT GAG ACC AAA AGC TGG TAC TTC ACT GAA AAT ATG GAA AGA AAC TGC AGG GCT CCC TGC 1910                            1920                            1930
      asn ile gln met glu asp pro thr phe lys glu asn tyr arg phe his ala ile asn gly tyr ile met asp thr leu pro gly leu val
5767  AAT ATC CAG ATG GAA GAT CCC ACT TTT AAA GAG AAT TAT CGC TTC CAT GCA ATC AAT GGC TAC ATA ATG GAT ACA CTA CCT GGC TTA GTA 1940                            1950                            1960
      met ala gln asp gln arg ile arg trp tyr leu leu ser met gly ser asn glu asn ile his ser ile his phe ser gly his val phe
5857  ATG GCT CAG GAT CAG AGG ATT CGA TGG TAT CTG CTC AGC ATG GGC AGC AAT GAA AAT ATC CAT TCT ATT CAT TTC AGT GGA CAT GTG TTC 1970                            1980                            1990
      thr val arg lys lys glu glu tyr lys met ala leu tyr asn leu tyr pro gly val phe glu thr val glu met leu pro ser lys ala
5947  ACT GTA CGA AAA GAG GAG TAT AAA ATG GCA CTG TAC AAT CTC TAT CCA GGT GTT TTT GAG ACA GTG GAA ATG TTA CCA TCC AAA GCT 2000                            2010                            2020
      gly ile trp arg val glu val cys leu ile gly glu his leu his ala gly met ser thr leu phe leu val tyr ser asn lys cys gln thr
6037  GGA ATT TGG CGG GTG GAA GTG TGC CTT ATT GGC GAG CAT CTA CAT GCT GGG ATG AGC ACA CTT TTT CTG GTG TAC AGC AAT AAG TGT CAG ACT 2030                            2040                            2050
      pro leu gly met ala ser gly his ile arg asp phe gln ile thr ala ser gly gln tyr gly gln trp ala pro lys leu ala arg leu
6127  CCC CTG GGA ATG GCT TCT GGA CAC ATT AGA GAT TTT CAG ATT ACA GCT TCA GGA CAA TAT GGA CAG TGG GCC CCA AAG CTG GCC AGA CTT
```

FIG.10C-2

```
                                                                                                                            2080
        his tyr ser gly ser ile asn ala trp ser thr lys glu pro phe ser trp ile lys val asp leu ala pro met ile leu ile his gly
6217    CAT TAT TCC GGA TCA ATC AAT GCC TGG AGC ACC AAG GAG CCC TTT TCT TGG ATC AAG GTG GAT CTG TTG GCA CCA ATG ATT ATT CAC GGC
                         2090                                2100                                2110
        ile lys thr gln gly ala arg gln lys phe ser ser leu tyr ile ile met tyr ser leu asp gly lys trp gln
6307    ATC AAG ACC CAG GGT GCC CGT CAG AAG TTC TCC AGC CTC TAC ATC ATG TAT AGT CTT GAT GGG AAG TGG CAG
                         2120                                2130                                2140
        thr tyr arg gly asn ser thr gly thr leu met val phe phe gly asn val asp ser ser gly ile lys his asn ile phe asn pro pro
6397    ACT TAT CGA GGA AAT TCC ACT GGA ACC TTA ATG GTC TTC TTT GGC AAT GTG GAT TCA TCT GGG ATA AAA CAC AAT ATT TTT AAC CCT CCA
                         2150                                2160                                2170
        ile ile ala arg tyr ile leu his pro thr his tyr ser ile arg ser thr leu arg ser met glu leu met gly cys asp leu asn ser
6487    ATT ATT GCT CGA TAC ATC CTT CAC CCA ACT CAT TAT AGC ATT CGC AGC ACT CTT CGC AGT ATG GAG TTG ATG GGC TGT GAT TTA AAT AGT
          sphI               2180                                2190                                2200
        cys ser met pro leu gly met glu ser lys ala ile thr asp gln ile thr ala ser ser tyr phe thr asn met phe ala thr trp
6577    TGC AGC ATG CCA TTG GGA ATG GAG AGT AAA GCA ATA TCA GAT CAG ATT ACT GCT TCA TCC TAC TTT ACC AAT ATG TTT GCC ACC TGG
                         2210                                2220                                2230
        ser pro ser lys ala arg leu his leu gln gly arg ser asn ala pro arg pro gln val asn asn pro lys glu trp leu gln val asp
6667    TCT CCT TCA AAA GCT CGA CTT CAC CTC CAA GGA AGG AGT AAT GCC CCT AGA CCT CAG GTG AAT AAT CCA AAA GAG TGG CTG CAA GTG GAC
                         2240                                2250                                2260
        phe gln lys thr met lys val thr gly val thr arg gln trp thr gln leu phe gln asn asp ser met tyr val lys val phe leu ile ser
6757    TTC CAG AAG ACA ATG AAA GTC ACA GGA GTA ACT CGA CAG TGG ACT CAG CTT TTT CAG AAT GAC AGC ATG TAT GTG AAG GAG TTC CTC ATC TCC
                         2270                                2280                                2290
        ser ser gln asp pro pro leu leu thr arg tyr leu thr gln ile ala leu arg met glu val
6847    AGC AGT CAA GAT CCA CCG TTA CTG ACT CGC TAC CTC CAG ATT GCC CTG AGG ATG GAG GTT
                         2300                   ecoRI     2310                                2320
6937    GTG AAC TCT CTA GAC CCC CCA CAG ATT CAC CCC CAG AGT TGG GTG CAC CAG ATT GCC CTG AGG ATG GAG GTT
```

FIG.10C-3

```
                              2330      2332
     leu gly cys glu ala gln asp leu tyr OP
     CTG GGC TGC GAG GCA CAG GAC CTC TAC TGA GGGTGGCCACTGCAGCACTGCACCTCTCCCTCCTCAGCTCCAGGGCAGTGTCCTCCCTGGCTTGCCTT
7027
7137 CTACCTTTGTGCTAAATCCTAGCAGACACTGCCTTGAAGCCTCTGAATTAACTATCATCAGTCCTGCATTCTTTGGTGGGGGCCAGGAGGGTGCATCCAATTAACTAACTCTTAC
7257 CTATTTTCTGCAGCTGCTCCCAGATTACTCCTCCTTCCCAATATAACTAGGCAAAAGAAGTGAGGAGAAACCTGCATGAAAGCATTCTTCCCTGAAAAGTTAGGCCTTCAGAGTCACC
7377 ACTTCCTCTGTTGTAGAAAAACTATGTGATGAAACTTTGAAAAAGATATATTTGATGTTAAGCCTCATACGTTTAAAAATAAACTCTCAGTTGTTATTATCCTGAT
7497 CAAGCATGGAACAAAGCATGTTTCAGGATCAGATCAATACAATCTTGGACAATCATTTGGACAATCTGCAAATGAGAGAATACAATAACTACACAGTAAAGTCTGTT
7617 TCTGCTTCCTTACACATAGATATAAGGCATTCTGTATAAATGCAAATGTGCATTTTCTGACGAGTGTCCATAGATATAAACTGAGAATTATAGATGGGGTTCAAGAATCCCTAAGT
                                                     hindIII
7737 CCCCTGAAATTATATAAGGCATTCTGTATAAATGCAAATGTGCATTTTCTGACGAGTGTCCATAGATATAAAGCCATTTGGTGTCTTAATTCTGACCAATAAAAAATAGTCAGGAGGAT
7857 GCAATTGTTGAAAGCTTTGAAATAAAATAACATGTCTTCTTGAAATTGTGATGGCCAAGAAGAAAATTGGACTTCTAAAGGACATACCATTTAATATTTCTGTGGAA
7977 ATATGAGGAAATCCATGGTTATCTGAGATAGGAGAGATACAAACTTTGTAATTCTAATAATGCACTCAGTTACTCTCCCTCTACTAATTCCTGCTGAAAATAACACAACAAAAATGT
8097 AACAGGGGAAATTATATACCGTGACTGAAAAACTAGAGTCCTACTTACAGTTGAAATATCAAGGAGGTCAGAAGAAAAACACTCCAGTCTGCCATA
8217 TCACCACACAATAGGATCCCCCCTTCTTGCCCTCCACCCCCATAAGATTGTGAAGGGTTTACTGCTCCTCCATCTGCCTGACCCCTCACTATGACTACACAGAATCTCTGATAGTAAA
                                                                                                            bamHI
8337 GGGGGGCTGGAGGCAAGGATTATAGAGCAGTTGGAGGAAGCATCCAAAGATTGCAACCCAGGGCAAATGGAAAACAGGAGAGATCCTAATATGAAAGAAAAATGGATCCAATCTGAGA
8457 AAAGGCAAAAGAATGGCTACTTTTTTCTATGCTGGAGTATTTTCTAATAATCCTGCTTGACCCTTATCTGACCTCTTTGGAAACTATAACATAGCTGTCACAGTATAGTCACAATCCACA
8577 AATGATGCAGGTGCAAATGGTTTATAGCCCTGTGAAGTTCTTAAAGTTTAGAGGCTAACTTACAGAAATGAATAAGTTGTTTGTTTATAGCCCGGTAGAGGAGTTAACCCAAAGGTG
8697 ATATGGTTTATTTCCTGTTATGTTAACTTGATAATCTTATTTTGGCATTCTTTTCCCATTGACTACTATATACATCTCTATATTTCTCAAATGTTCATGAACTAGCTCTTTTATTTCCTGC
8817 TGGTTCTTCAGTAATGAGTTAAATAAAACATTGACACATACAAAAAAAA
```

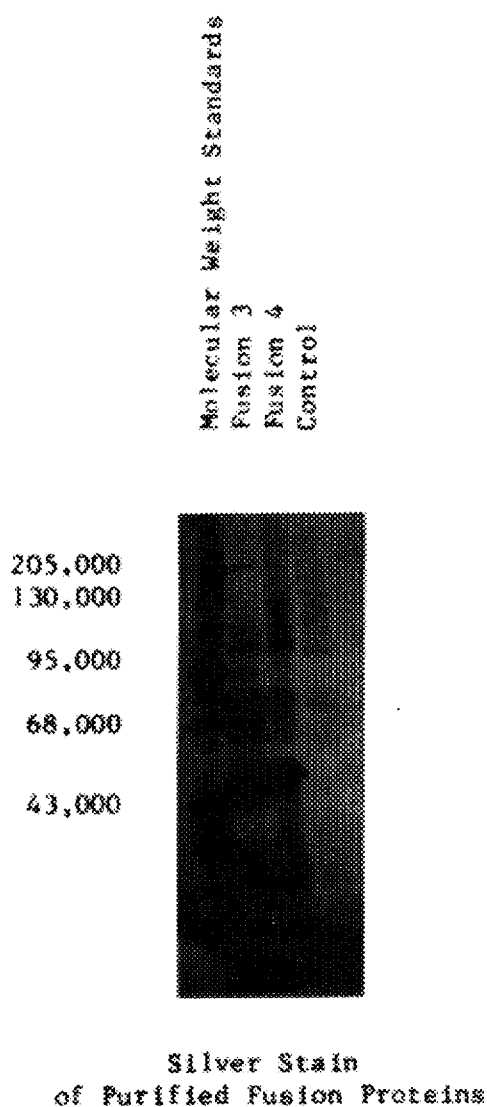 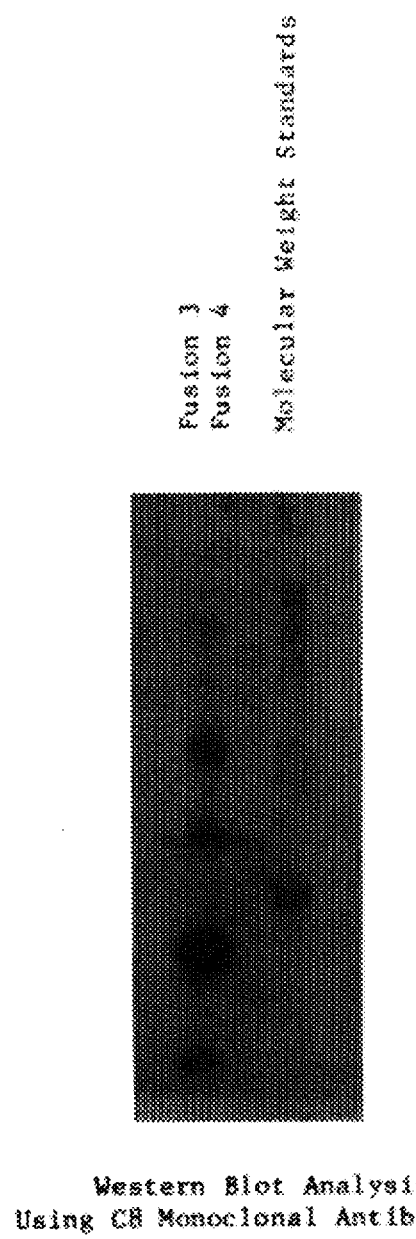
Silver Stain
of Purified Fusion Proteins
FIG. 14A
Western Blot Analysis
Using C8 Monoclonal Antibody
FIG. 14B

VECTORS AND CELL LINES CAPABLE OF CORRECTLY SPLICING EXON REGIONS

This is a continuation of applications(s) Ser. No. 07/595,481 filed on 09 Oct. 1990 which is a continuation of Ser. No. 07/083,758 filed 07 Aug. 1987, now U.S. Pat. No. 4,965,199 which is a continuation of Ser. No. 06/602,312 filed 20 Apr. 1984, now abandoned, which applications are incorporated herein by reference and to which applications priority is claimed under 35 USC §120.

FIELD OF THE INVENTION

The present invention relates to human factor VIII, to novel forms and compositions thereof and particularly to means and methods for the preparation of functional species of human factor VIII, particularly via recombinant DNA technology.

The present invention is based in part on the discovery of the DNA sequence and deduced amino acid sequence of human factor VIII as well as associated portions of the factor VIII molecule found in our hands to be functional bioactive moieties. This discovery was enabled by the production of factor VIII in various forms via the application of recombinant DNA technology, thus, in turn enabling the production of sufficient quality and quantity of materials with which to conduct biological testing and prove biological functionality. Having determined such, it is possible to tailor-make functional species of factor VIII via genetic manipulation and in vitro processing, arriving efficiently at hitherto unobtainable commercially practical amounts of active factor VIII products. This invention is directed to these associated embodiments in all respects.

The publications and other materials hereof used to illuminate the background of the invention, and in particular cases, to provide additional details concerning its practice are incorporated herein by reference and listed at the end of the specification in the form of a bibliography.

BACKGROUND OF THE INVENTION

The maintenance of an intact vascular system requires the interaction of a variety of cells and proteins. Upon injury to the vascular bed, a series of reactions is initiated in order to prevent fluid loss. The initial response is the activation of platelets, which adhere to the wound and undergo a series of reactions. These reactions include the attraction of other platelets to the site, the release of a number of organic compounds and proteins, and the formation of a thrombogenic surface for the activation of the blood coagulation cascade. Through this combined series of reactions, a platelet plug is formed sealing the wound. The platelet plug is stabilized by the formation of fibrin threads around the plug preventing unwanted fluid loss. The platelet plug and fibrin matrix are subsequently slowly dissolved as the wound is repaired. For a general review, see (1).

A critical factor in the arrest of bleeding is the activation of the coagulation cascade in order to stabilize the initial platelet plug. This system consists of over a dozen interacting proteins present in plasma as well as released and/or activated cellular proteins (2, 3). Each step in the cascade involves the activation of a specific inactive (zymogen) form of a protease to the catalytically active form. By international agreement (4), each protein of the cascade has been assigned a Roman numeral designation. The zymogen form of each is represented by the Roman numeral, while the activated form is represented by the Roman numeral followed by a subscript "a". The activated form of the protease at each step of the cascade catalytically activates the protease involved in the subsequent step in the cascade. In this manner a small initial stimulus resulting in the activation of a protein at the beginning of the cascade is catalytically amplified at each step such that the final outcome is the formation of a burst of thrombin, with the resulting thrombin catalyzed conversion of the soluble protein fibrinogen into its insoluble form, fibrin. Fibrin has the property of self-aggregating into threads or fibers which function to stabilize the platelet plug such that the plug is not easily dislodged.

FIG. 1 summarizes the current understanding of the interactions of the proteins involved in blood coagulation. The lack or deficiency of any of the proteins involved in the cascade would result in a blockage of the propagation of the initial stimulus for the production of fibrin. In the middle of the cascade represented in FIG. 1 is a step wherein factor $IX_a$ initiates the conversion of factor X to the activated form, factor $X_a$. Factor VIII (also synonomously referred to as factor VIIIC) is currently believed to function at this step, in the presence of phospholipid and calcium ions, as a cofactor; that is, it has no known function in itself, and is required to enhance the activity of factor IXa. This step in the cascade is critical since the two most common hemophilia disorders have been determined to be caused by the decreased functioning of either factor VIII (hemophilia A or classic hemophilia) or factor IXa (hemophilia B). Approximately 80 percent of hemophilia disorders are due to a deficiency of factor VIII. The clinical manifestation in both types of disorders are the same: a lack of sufficient fibrin formation required for platelet plug stabilization, resulting in a plug which is easily dislodged with subsequent rebleeding at the site. The relatively high frequency of factor VIII and factor IX deficiency when compared with the other factors in the coagulation cascade is due to their genetic linkage to the X-chromosome. A single defective allele of the gene for factor VIII or factor IX results in hemophilia in males, who have only one copy of the X chromosome. The other coagulation factors are autosomally linked and generally require the presence of two defective alleles to cause a blood coagulation disorder—a much less common event. Thus, hemophilia A and B are by far the most common hereditary blood clotting disorders and they occur nearly exclusively in males.

Several decades ago the mean age of death of hemophiliacs was 20 years or younger. Between the early 1950's and the late 1960's, research into the factor VIII disorder led to the treatment of hemophilia A initially with whole plasma and, later, with concentrates of factor VIII. The only source for human factor VIII has been human plasma. One factor contributing to the expense is the cost associated with obtaining large amounts of usable plasma. Commercial firms must establish donation centers, reimburse donors, and maintain the plasma in a frozen state immediately after donation and through the shipment to the processing plant. The plasma samples are pooled into lots of over 1000 donors and processed. Due to the instability of the factor VIII activity, large losses are associated with the few simple purification procedures utilized to produce the concentrates (resulting in approximately a 15 percent recovery of activity). The resulting pharmaceutical products are highly impure, with a specific activity of 0.5 to 2 factor VIII units per milligram of protein (one unit of factor VIII activity is by definition the activity present in one milliliter of plasma). The estimated purity of factor VIII concentrate is approximately 0.04 percent factor VIII protein by weight. This high impurity level is associated with a variety of serious complications including precipitated protein, hepatitis, and possibly the agent responsible for Acquired Immune Deficiency Syndrome. These disadvantages of the factor VIII concentrates are due to the instability of the plasma derived factor VIII, to its low level of purity, and to its derivation from a pool of multiple donors. This means that should one individual out of the thousand donors have, for example, hepatitis, the whole lot would be tainted with the virus. Donors are screened for hepatitis B, but the concentrates are known to contain both hepatitis A and hepatitis non-A non-B. Attempts to produce a product of higher purity result in unacceptably large losses in activity, thereby increasing the cost.

The history of purification of factor VIII illustrates the difficulty in working with this protein. This difficulty is due in large part to the instability and trace amounts of factor VIII contained in whole blood. In the early 1970's, a protein was characterized which was then believed to be factor VIII (5, 6, 7). This protein was determined to be an aggregate of a subunit glycoprotein, the subunit demonstrating a molecular weight of approximately 240,000 daltons as determined by SDS gel electrophoresis. This subunit aggregated into a heterogeneous population of higher molecular weight species ranging from between one million and twenty million daltons. The protein was present in hemophiliac plasma, but missing in plasma of patients with von Willebrand's disease, an autosomally transmitted genetic disorder characterized by a prolonged bleeding time and low levels of factor VIII (8). The theory then proposed was that this high molecular weight protein, termed von Willebrand factor (vWF) or factor VIII related antigen (FVIIIRAg), was responsible for the coagulation defect in both diseases, with the protein being absent in von Willebrand's disease and somehow non-functional in classic hemophilia disease states (9). However, it was later observed that under certain conditions, notably high salt concentrations, the factor VIII activity could be separated from this protein believed responsible for the activity of factor VIII (10–20). Under these conditions, the factor VIII coagulant activity exhibited a molecular weight of 100,000 to 300,000. Since this time, great effort has concentrated on identifying and characterizing the protein(s) responsible for the coagulant activity of factor VIII. However, the availability of but trace amounts of the protein in whole blood coupled with its instability have hampered such studies.

Efforts to isolate factor VIII protein(s) from natural source, both human and animal, in varying states of purity, have been reported (21–27, 79). Because of the above mentioned problems, the possibility exists for the mistaken identification and subsequent cloning and expression of a contaminating protein in a factor VIII preparation rather than the factor VIII protein intended. That this possibility is real is emphasized by the previously mentioned mistaken identification of von Willebrand protein as being the factor VIII coagulant protein. Confusion over the identification of factor VIII-like activity is also a distinct possibility. Either factor Xa or thrombin would cause a shortening of the clotting time of various plasmas, including factor VIII deficient plasma, thereby appearing to exhibit factor VIII-like activity unless the proper controls were performed. Certain cells are also known to produce activities which can function in a manner very similar to that expected of factor VIII (28, 29, 30). The latter reference (30) proves that this factor VIII-like activity is in fact a protein termed tissue factor. The same or similar material has also been purified from human placenta (31). This protein functions, in association with the plasma protein factor VII, at the same step as factor VIII and factor $IX_a$, resulting in the activation of factor X to factor $X_a$.

The burden of proof for expression of a recombinant factor VIII would therefore rest on the proof of functional expression of what is unquestionably a factor VIII activity. Even were prior workers to show that they obtained a full or partial clone encoding all or a portion of factor VIII, the technical problems in the expression of a recombinant protein which is four times larger than any other recombinant protein expressed to date could well have proven insurmountable to workers of ordinary skill.

SUMMARY OF THE INVENTION

The potential artifacts and problems described above combine to suggest the need for close scrutiny of any claims of successful cloning and expression of human factor VIII. The success of the present invention is evidenced by:

1) Immunological cross-reactivity of antibodies raised against clone-derived factor VIII proteins with plasma-derived factor VIII proteins.
2) Cross-reaction of neutralizing monoclonal antibodies raised against human plasma factor VIII with protein encoded by the clone.
3) Identification of a genomic DNA corresponding to the factor VIII cDNA of the invention as being located in the X-chromosome, where factor VIII gene is known to be encoded.
4) Expression of a functional protein which exhibits:
    a) Correction of factor VIII deficient plasma.
    b) Activation of factor X to factor $X_a$ in the presence of factor $IX_a$, calcium and phospholipid.
    c) Inactivation of the activity observed in a) and b) by antibodies specific for factor VIII.
    d) Binding of the activity to an immobilized monoclonal antibody column specific for factor VIII.
    e) Activation of the factor VIII activity by thrombin.
    f) Binding of the activity to and subsequent elution from immobilized von Willebrand factor.

Thus, the present invention is based upon the successful use of recombinant DNA technology to produce functional human factor VIII, and in amounts sufficient to prove identification and functionality and to initiate and conduct animal and clinical testing as prerequisites to market approval. The product, human factor VIII, is suitable for use, in all of its functional forms, in the prophylactic or therapeutic treatment of human beings diagnosed to be deficient in factor VIII coagulant activity. Accordingly, the present invention, in one important aspect, is directed to methods of diagnosing and treating classic hemophilia (or hemophilia A) in human subjects using factor VIII and to suitable pharmaceutical compositions therefor.

The present invention further comprises essentially pure, functional human factor VIII. The product produced herein by genetically engineered appropriate host systems provides human factor VIII in therapeutically useful quantities and purities. In addition, the factor VIII hereof is free of the contaminants with which it is ordinarily associated in its non-recombinant cellular environment.

The present invention is also directed to DNA isolates as well as to DNA expression vehicles containing gene sequences encoding human factor VIII in expressible form, to transformant host cell cultures thereof, capable of producing functional human factor VIII. In still further aspects, the present invention is directed to various processes useful for preparing said DNA isolates, DNA expression vehicles, host cell cultures, and specific embodiments thereof. Still further, this invention is directed to the preparation of fermentation cultures of said cell cultures.

Further, the present invention provides novel polypeptides comprising moiety(ies) corresponding to functional segments of human factor VIII. These novel polypeptides may represent the bioactive and/or antigenic determinant segments of native factor VIII. For example, such polypeptides are useful for treating hemophiliacs per se, and particularly those who have developed neutralizing antibodies to factor VIII. In the latter instance, treatment of such patients with polypeptides bearing the requisite antigen determinant(s) could effectively bind such antibodies, thereby increasing the efficiency of treatment with polypeptides bearing the bioactive portions of human factor VIII.

The factor VIII DNA isolates produced according to the present invention, encoding functional moiety(ies) of human factor VIII, find use in gene therapy, restoring factor VIII activity in deficient subjects by incorporation of such DNA, for example, via hematopoetic stem cells.

Particularly Preferred Embodiment

Human factor VIII is produced in functional form in a particularly suitable host cell system. This system comprises baby hamster kidney cells (BHK-21 (C-13), ATCC No. CCL 10) which have been transfected with an expression vector comprising DNA encoding human factor VIII, including 3'- and 5'- untranslated DNA thereof and joined at the 3'-untranslated region with 3'- untranslated terminator DNA sequence, e.g., such as from hepatitis B surface antigen gene. Expression of the gene is driven by transcriptional and translational control elements contributed by the adenovirus major late promoter together with its 5' spliced leader as well as elements derived from the SV40 replication origin region including transcriptional enhancer and promoter sequences. In addition, the expression vector may also contain a DHFR gene driven by an SV40 early promoter which confers gene amplification ability, and a selectable marker gene, e.g., neomycin resistance (which may be provided via cotransfection with a separate vector bearing neomycin resistance potential).

DESCRIPTION OF THE DRAWINGS

FIG. 3. Detection of the Factor VIII gene with probe 8.3. Left three panels: Southern blots of 46,XY (1X, male) DNA and 49,XXXXY (4X) human DNA digested with EcoRI and BamHI were hybridized in 6× SSC, 50 mM sodium phosphate (pH 6.8), 5× Denhardt's solution, 0.1 g/l boiled, sonicated salmon sperm DNA, 20 percent formamide at 42° C. as described in Methods. The three blots were washed in 1× SSC, 0.1 percent SDS at the temperature indicated. Lane 1, EcoRI 1X; lane 2, EcoRI 4X; lane 3, BamHI 1X; and lane 4, BamHI 4X. Lane M, end-labeled λHindIII and φX174 HaeIII digested marker fragments. Right panel: One nitrocellulose filter from the λ/4X library screen hybridized with probe 8.3. Arrows indicate two of the independent Factor VIII positive clones. Hybridization and washing for the library screen was as described above for the Southern blots, with a wash temperature of 37° C.

Figure 6:
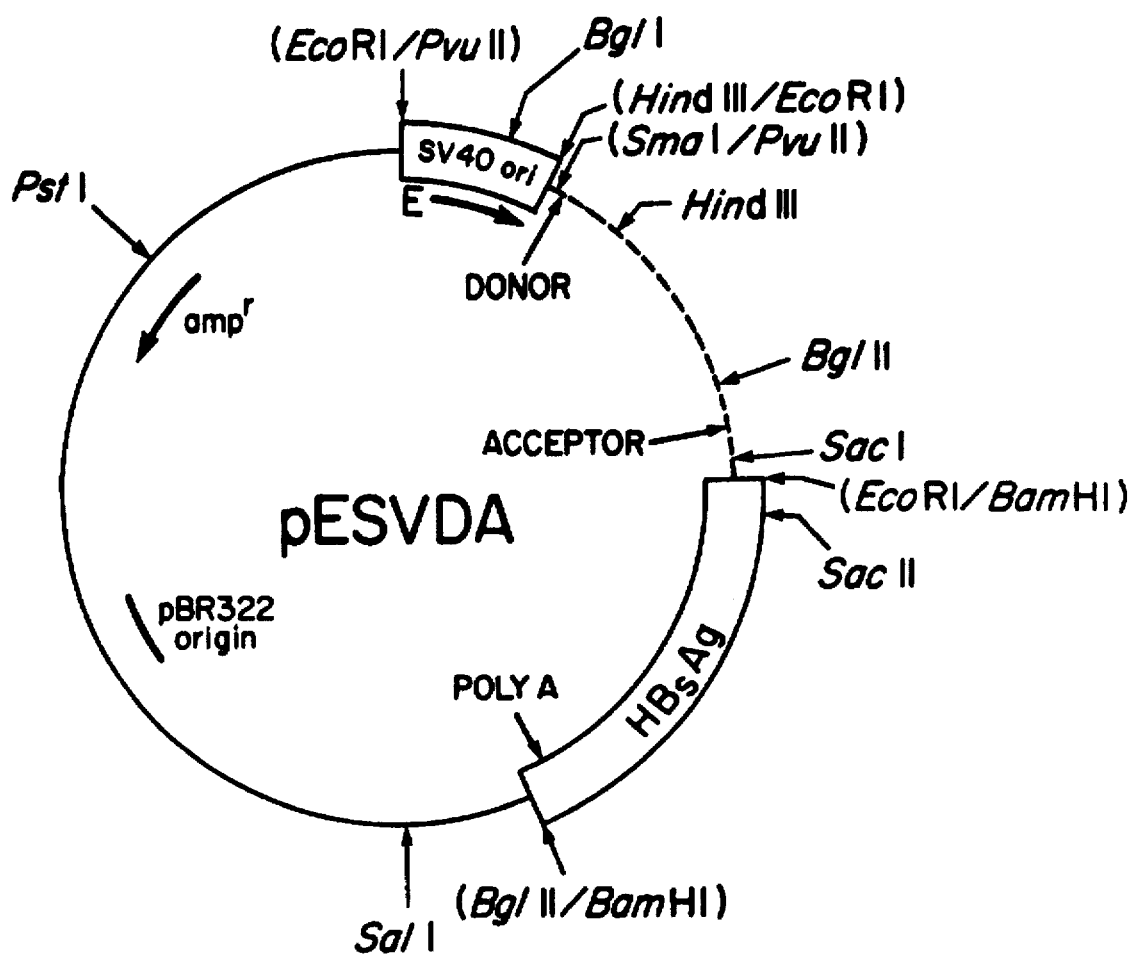
FIG. 6. Map of pESVDA. The 342 b PvuII-HindIII fragment of SV40 virus spanning the SV40 origin of replication and modified to be bounded by EcoRI sites (73), the polyadenylation site of hepatitis B virus (HBV) surface antigen (49n), contained on a 580 bp BamHI-BglII fragment, and the pBR322 derivative pML (75) have been previously described. Between the EcoRI site following the SV40 early promoter and the BamHI site of HBV was inserted the PvuII-HindIII fragment (map coordinates 16.63–17.06 of Adenovirus 2) containing the donor splice site of the first late leader (position 16.65) immediately followed by the 840 bp HindIII-SacI fragment of Adenovirus 2 (position 7.67–9.97) (49j), containing the E1b acceptor splice site at map position 9.83. Between the donor and acceptor sites lie unique BglII and HindIII sites for inserting genomic DNA fragments.

The 9.4 kb BamHI fragment of λ114 containing exon A (see FIG. 4) was cloned into the BglII site of pESVDA (FIG. 6). Plasmid pESVDA111.6 contained the fragment inserted in the orientation such that the SV40 early promoter would transcribe the genomic fragment in the proper (i.e., sense) direction. pESVDA111.7 contains the 9.4 kb BamHI fragment in the opposite orientation. Plasmid pESVDA.S127 contains the 12.7 kb SacI fragment of λ114 inserted (by blunt end ligation) into the BglII site of pESVDA in the same orientation as pESVDA111.6.

A. Hybridization of filters containing total cytoplasmic RNA from cells transfected with pESVDA, pESVDA111.7 and pESVDA111.6. pESVD RNA (lane 1), pESVDA111.7 (lane 2), pESVDA111.6 (lanes 3–5). Probed with Factor 8 exon A containing fragment (lanes 1–4) or 1800 b StuI/Bam fragment (lane 5). Faint cross-hybridization is seen to 18S RNA.

B. Hybridization of RNA with StuI/BamHI probe ("intron robe"). RNA from: 1) pESVDA, polyA$^-$; 2) pESVDA, polyA$^+$; 3) pESVDA111.7, polyA$^-$; 4) pESVDA111.7, polyA$^+$; 5) pESVDA111.6, polyA$^-$; 6) pESVDA111.6, polyA$^+$. The small dark hybridizing band seen in lanes A5, B1, B3 and B5 probably represents hybridization to tRNA or to an Alu repeat sequence found in this region.

C. Comparison of cytoplasmic RNA from pESVDA111.6 (lane 1) and pESVDA.S127 (lane 2) probed with exon A containing fragment. Note the slight size increase in lane 2 representing additional exon sequences contained in the larger genomic fragment.

FIG. 8. Sequence of pESVDA.S127 cDNA clone S36. The DNA sequence of the human DNA insert is shown for the cDNA clone S36 obtained from the exon expression plasmid pESVDA.S127 (see infra for details). Vertical lines mark exon boundaries as determined by analysis of genomic and cDNA clones of factor VIII, and exons are lettered as in FIG. 4. Selected restriction endonuclease sites are indicated.

Figure 9:
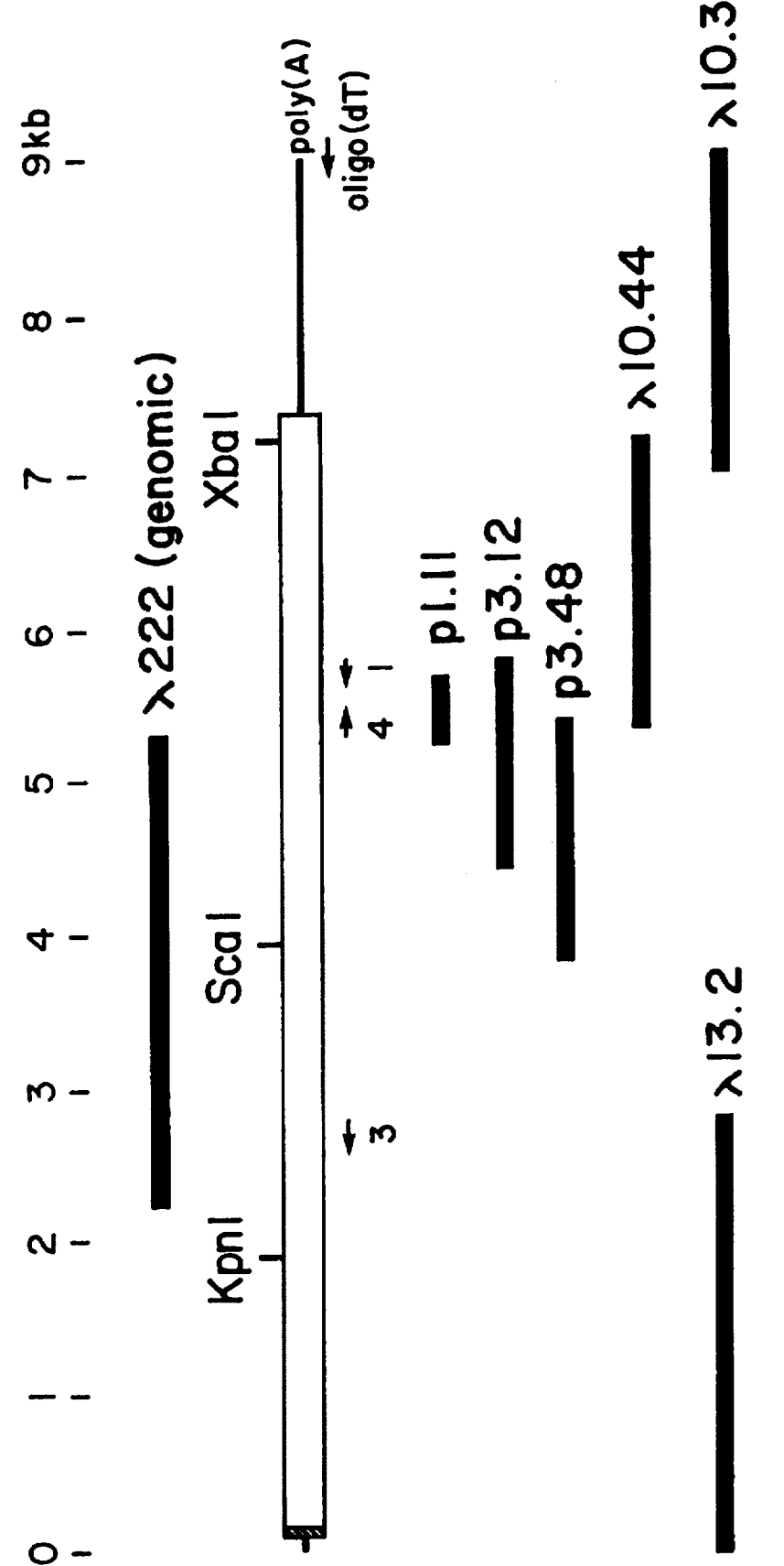
Figure 11A:
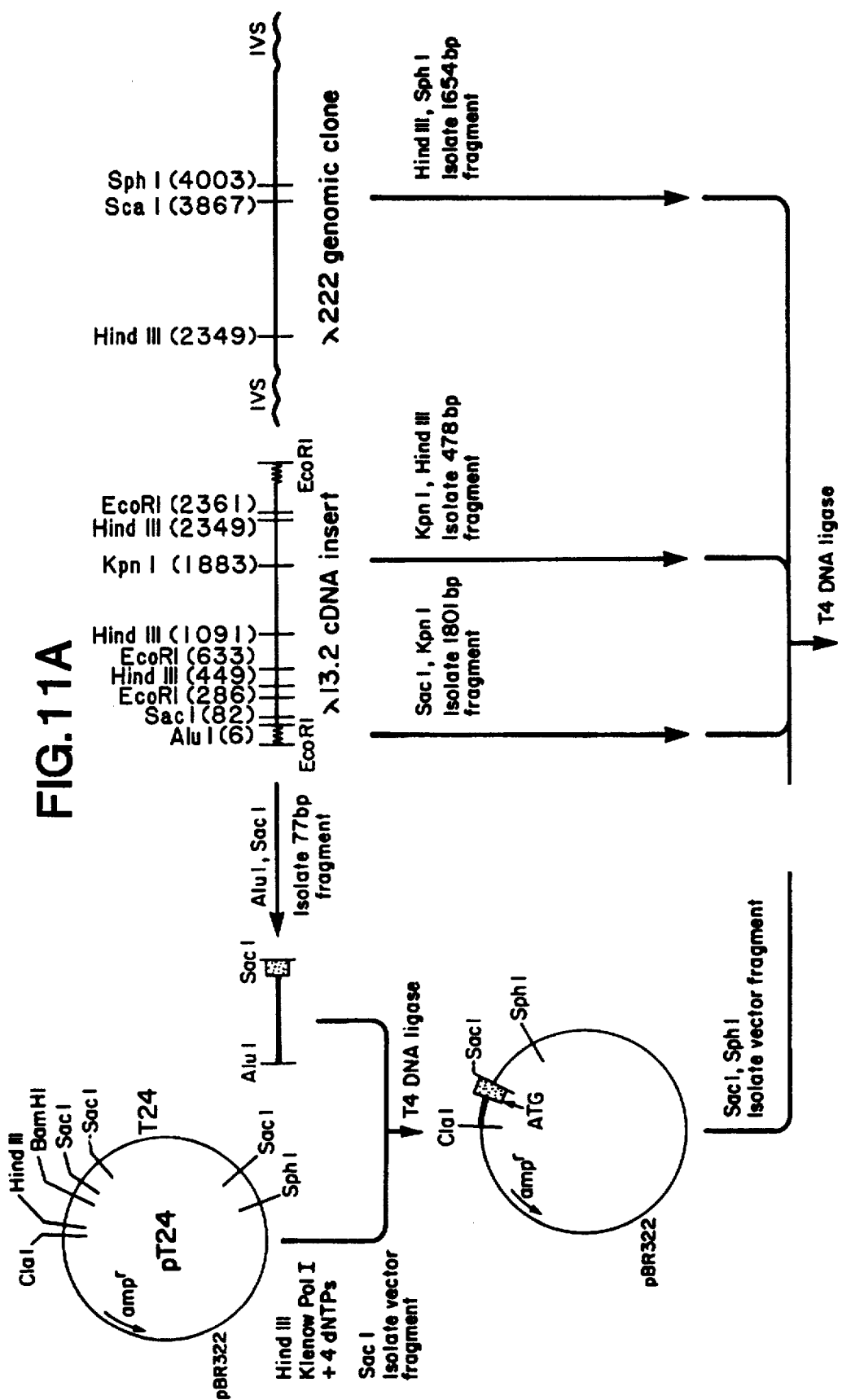
Figure 11B:
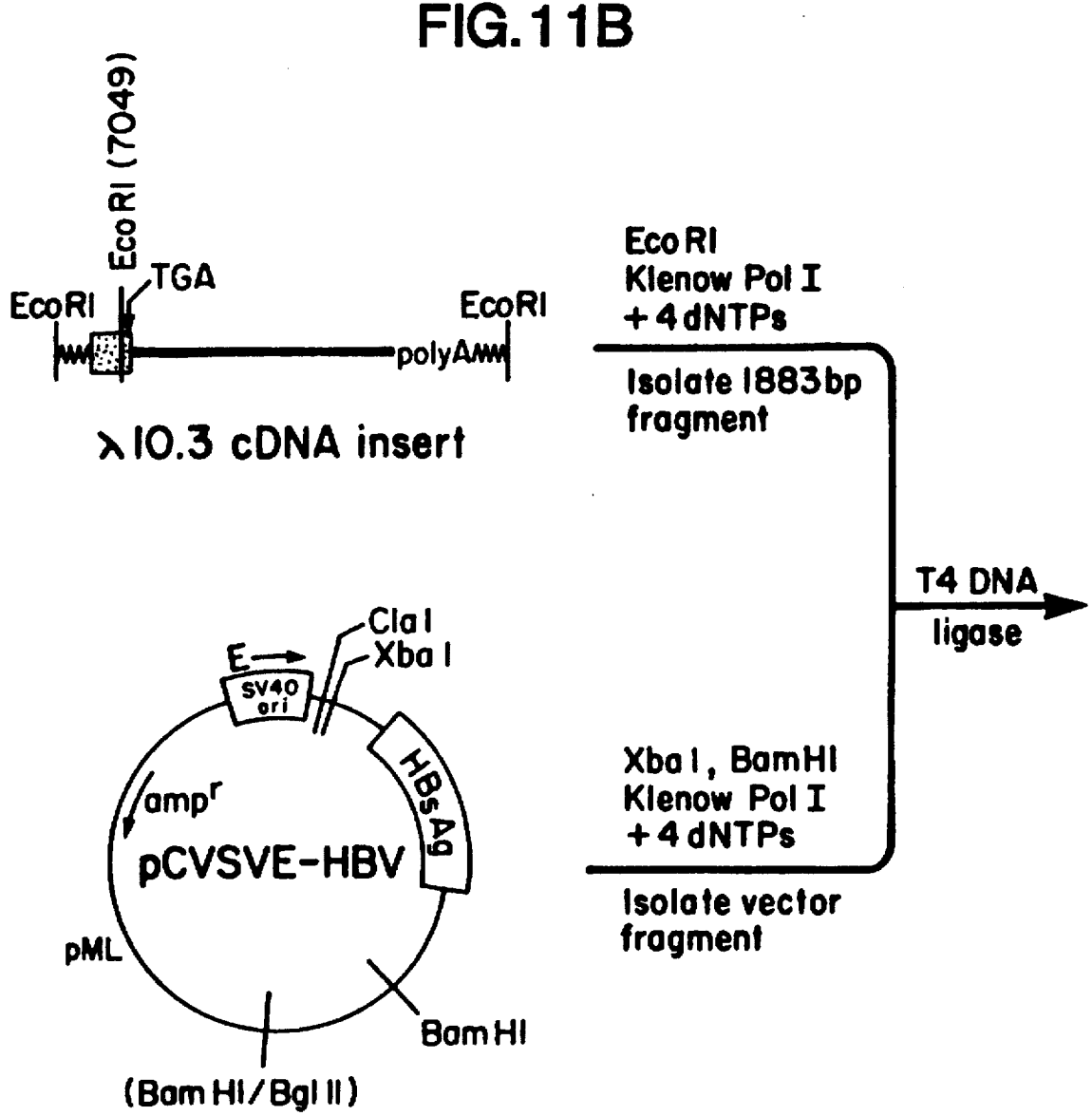
Figure 11C:
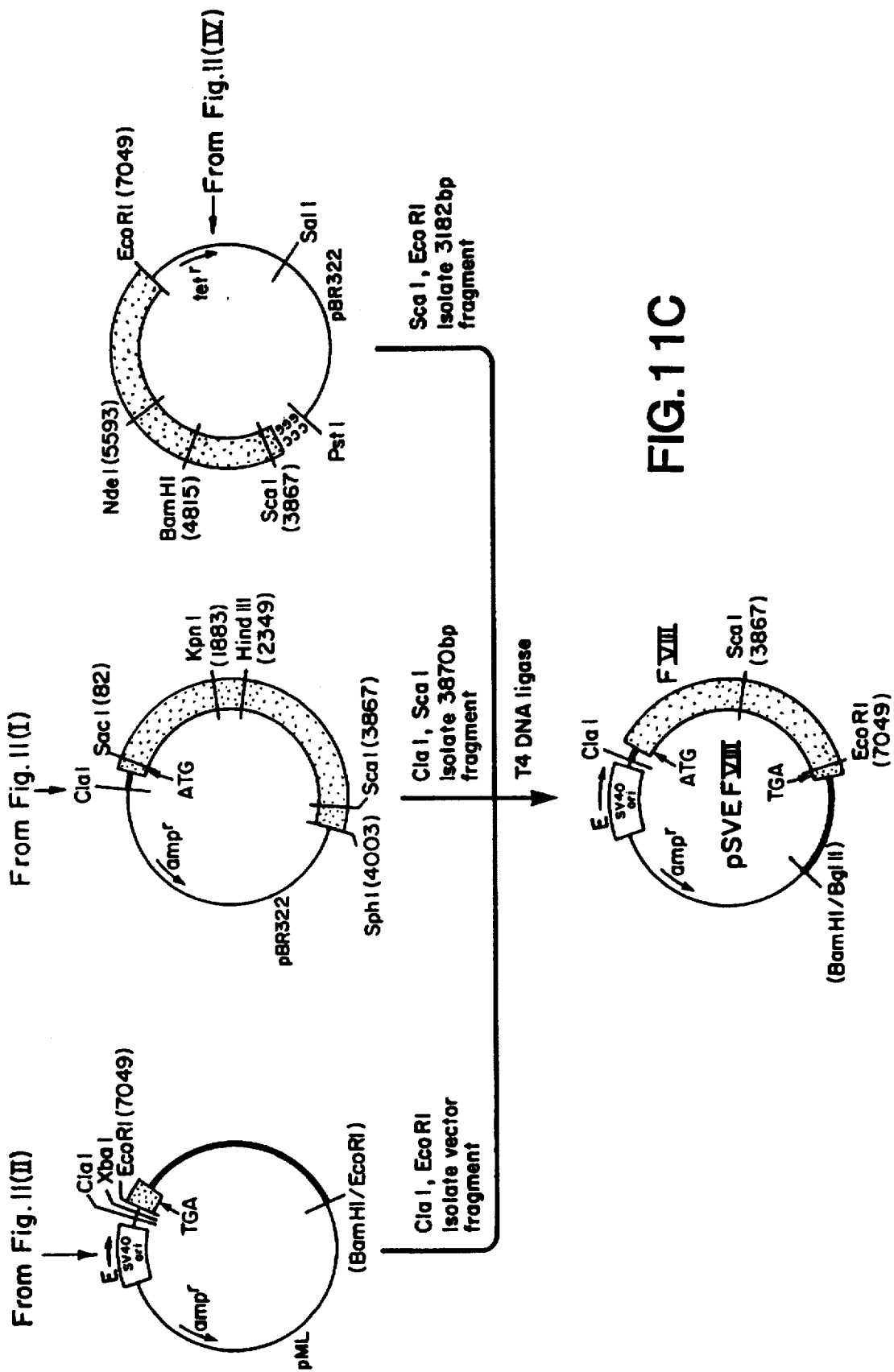
Figure 11D:
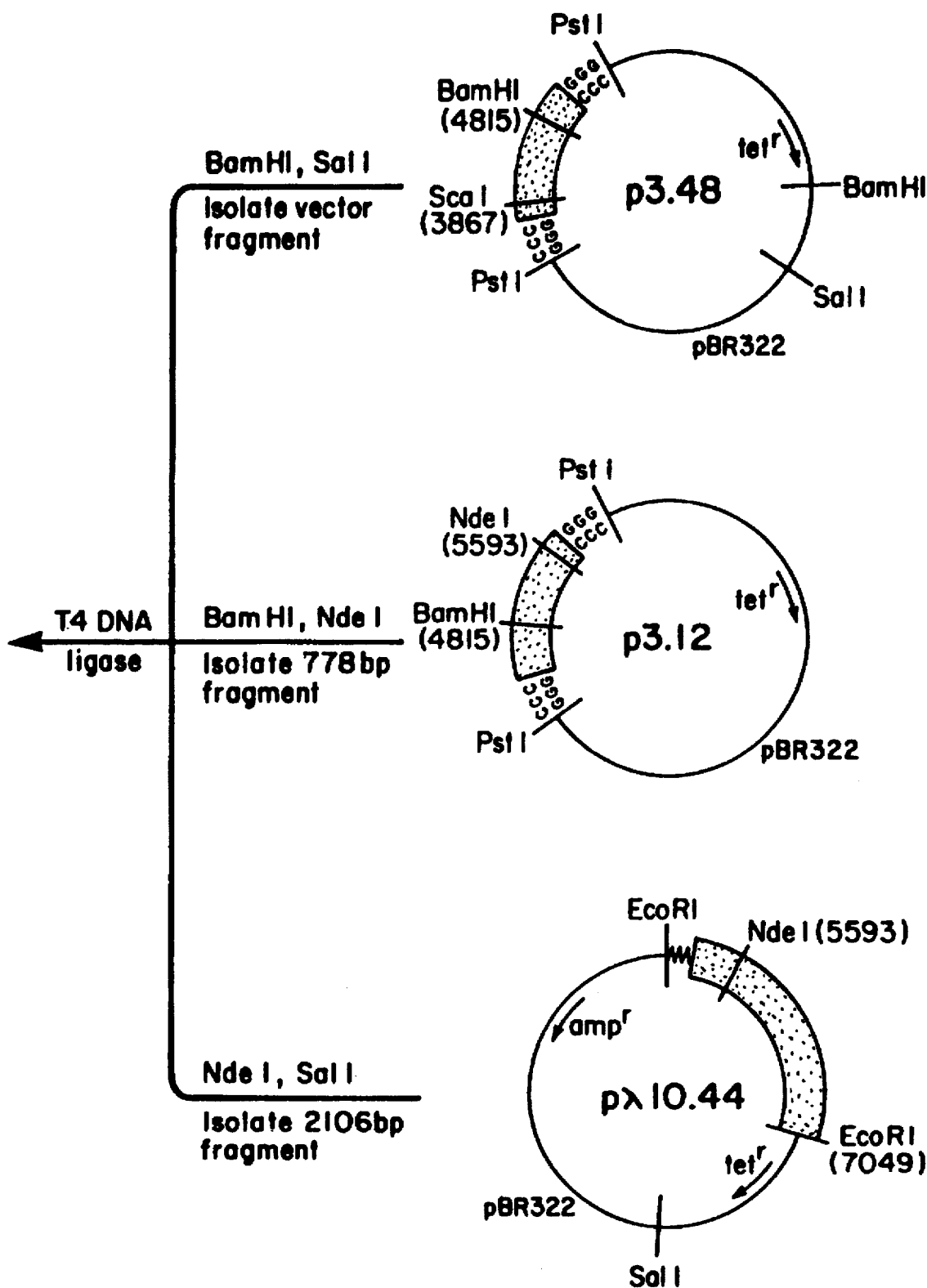

FIG. 9. cDNA cloning. Factor VIII mRNA is depicted on the third line with the open bar representing the mature protein coding region; the hatched area the signal peptide coding region, and adjacent lines the untranslated regions of the message. The 5' end of the mRNA is at the left. Above this line is shown the extent of the exon B region of the genomic clone λ222, and below the mRNA line are represented the six cDNA clones from which were assembled the full length factor VIII clone (see text for details). cDNA synthesis primers 1, 3, 4 and oligo(dT) are shown with arrows depicting the direction of synthesis for which they primed. Selected restriction endonuclease sites and a size scale in kilobases are included.

FIG. 10 (A–C). Sequence of Human Factor VIII Gene. The complete nucleotide sequence of the composite Factor VIII cDNA clone is shown with nucleotides numbered at the left of each line. Number one represents the A of the translation initiation codon ATG. Negative numbers refer to 5' untranslated sequence. (mRNA mapping experiments suggest that Factor VIII mRNA extends approximately 60 nucleotides farther 5' than position −109 shown here.) The predicted protein sequence is shown above the DNA. Numbers above the amino acids are S1-19 for the predicted signal peptide, and 1-2332 for the predicted mature protein. "Op" denotes the opal translation stop codon TAG. The 3' polyadenylation signal AATAAA is underlined and eight residues of the poly(A) tail (found in clone λc10.3) are shown. The sequence homologous to the synthetic oligonucleotide probe 8.3 has also been underlined (nucleotides 5557–5592). Selected restriction endonuclease cleavage sites are shown above the appropriate sequence. Nucleotides 2671–3217 represent sequence derived from genomic clones while the remainder represents cDNA sequence.

The complete DNA sequence of the protein coding region of the human factor VIII gene was also determined from the genomic clones we have described. Only two nucleotides differed from the sequence shown in this figure derived from cDNA clones (except for nucleotides 2671–3217). Nucleotide 3780 (underlined) is G in the genomic clone, changing the amino acid codon 1241 from asp to glu. Nucleotide 8728 (underlined) in the 3' untranslated region is A in the genomic clone.

FIG. 11. Assembly of full length recombinant factor VIII plasmid. See the text section 8a for details of the assembly of the plasmid pSVEFVIII containing the full length of human factor VIII cDNA. The numbering of positions differs from those in the text and FIG. 10 by 72 bp.

Figure 12A:
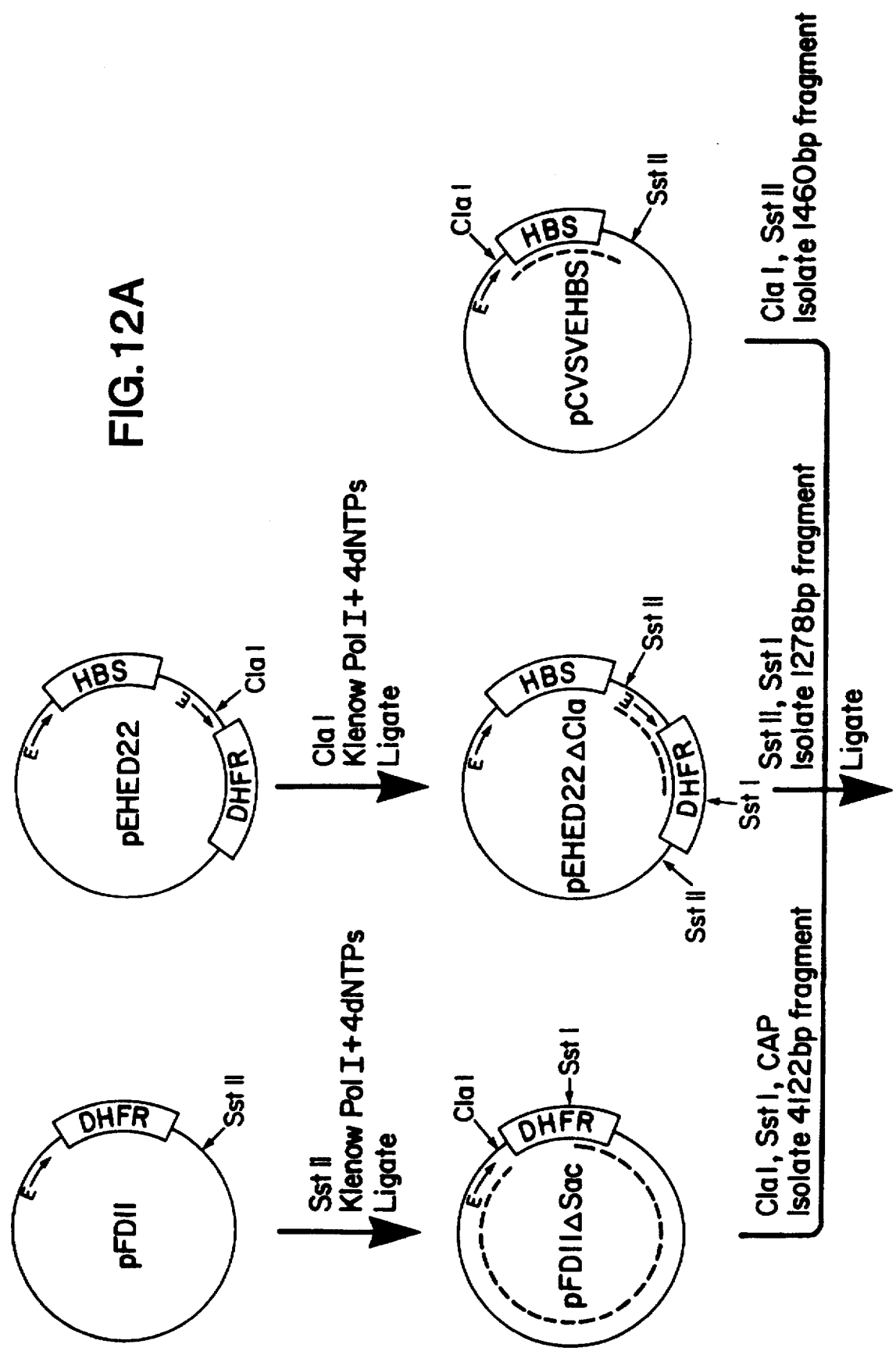
Figure 12B:
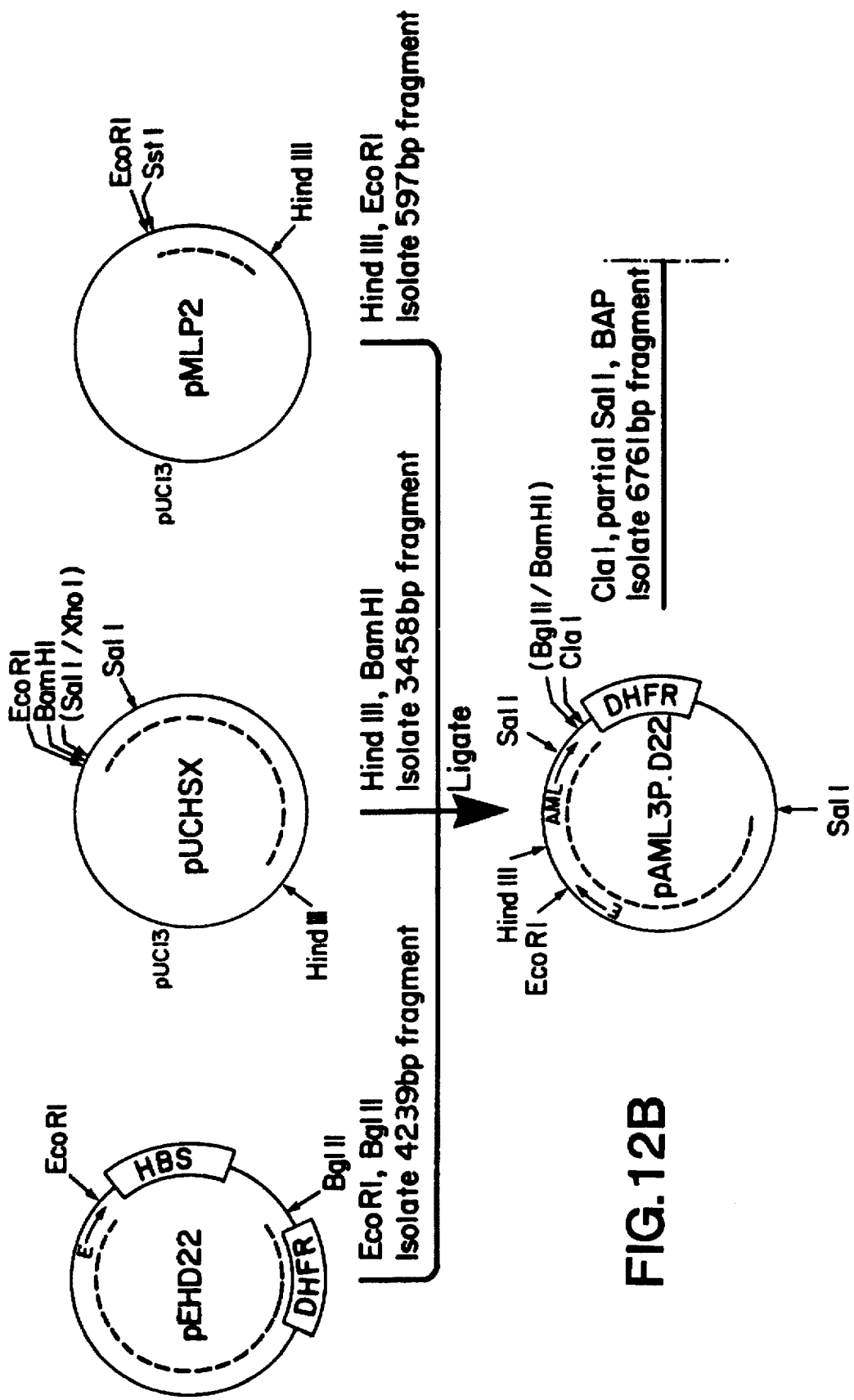
Figure 12C:
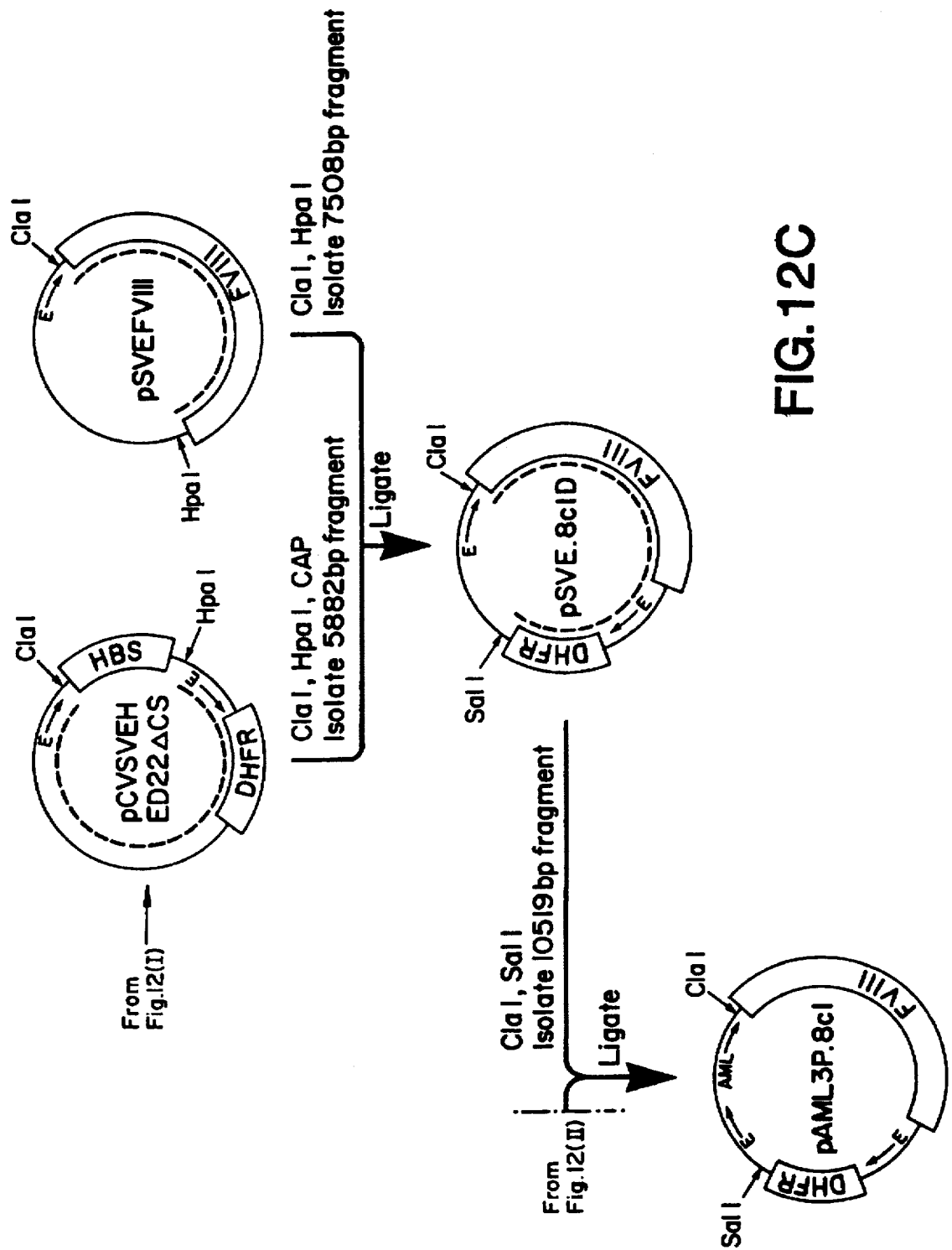

FIG. 12. Assembly of the factor VIII expression plasmid. See the text section 8b for details of the assembly of the plasmid pAML3p.8c1 which directs the expression of functional human factor VIII in BHK cells.

Figures 13A, 13B, 13C, 13D:
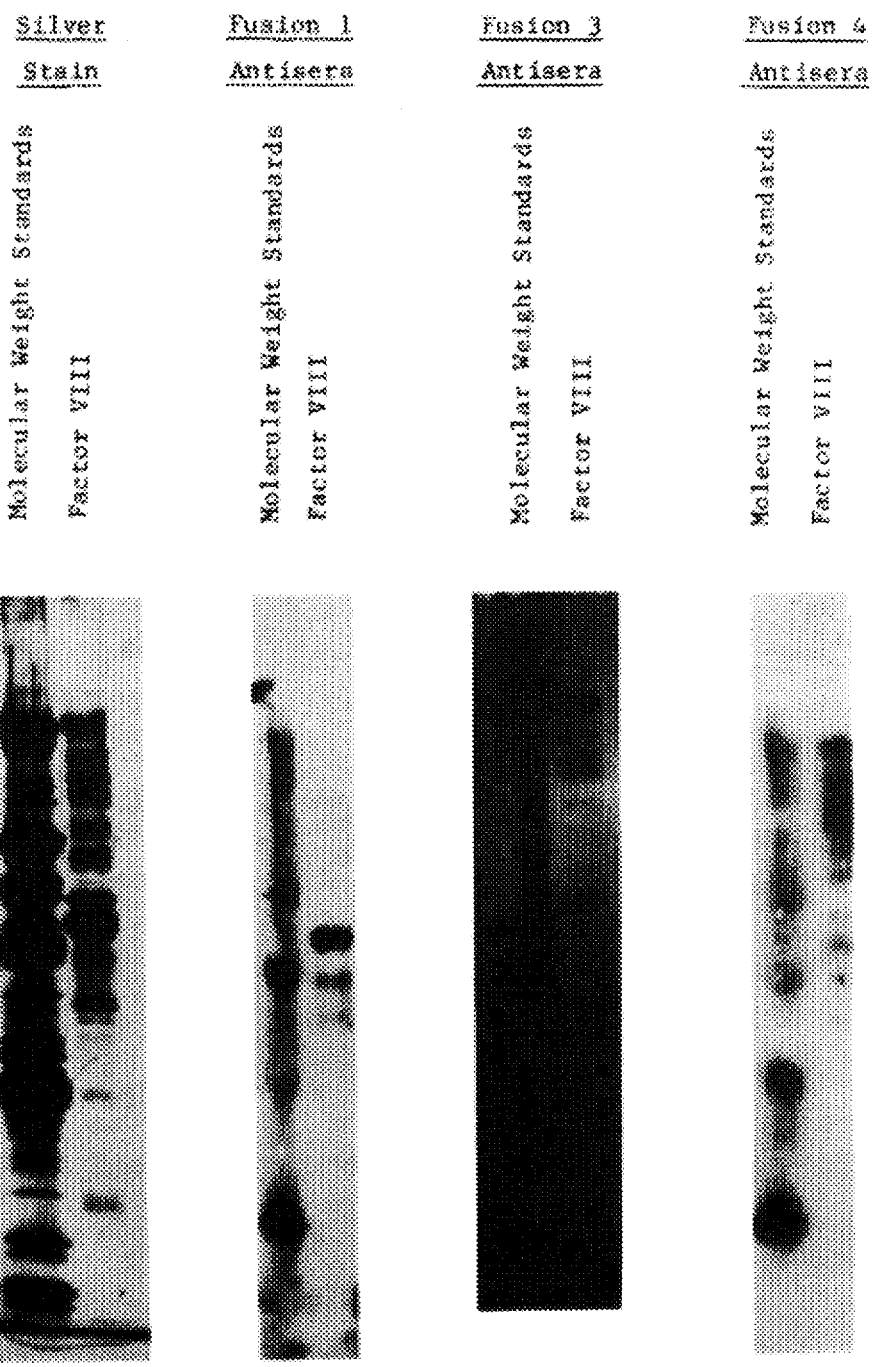

FIG. 13. Western Blot analysis of factor VIII using fusion protein antisera. Human factor VIII was separated on a 5–10 percent polyacrylamide gradient SDS gel according to the procedure of (81). One lane of factor VIII was stained with silver (80). The remaining lanes of factor VIII were electrophoretically transferred to nitrocellulose for Western Blot analysis. Radiolabeled standards were applied into lanes adjacent to factor VIII in order to estimate the molecular weight of the observed bands. As indicated, the nitrocellulose strips were incubated with the appropriate antisera, washed, and probed with $^{125}$I protein A. The nitrocellulose sheets were subjected to autoradiography.

FIG. 14. Analysis of fusion proteins using C8 monoclonal antibody. Fusion proteins 1, 3 and 4 were analyzed by Western blotting analysis for reactivity with the factor VIII specific monoclonal antibody C8.

Figure 15:
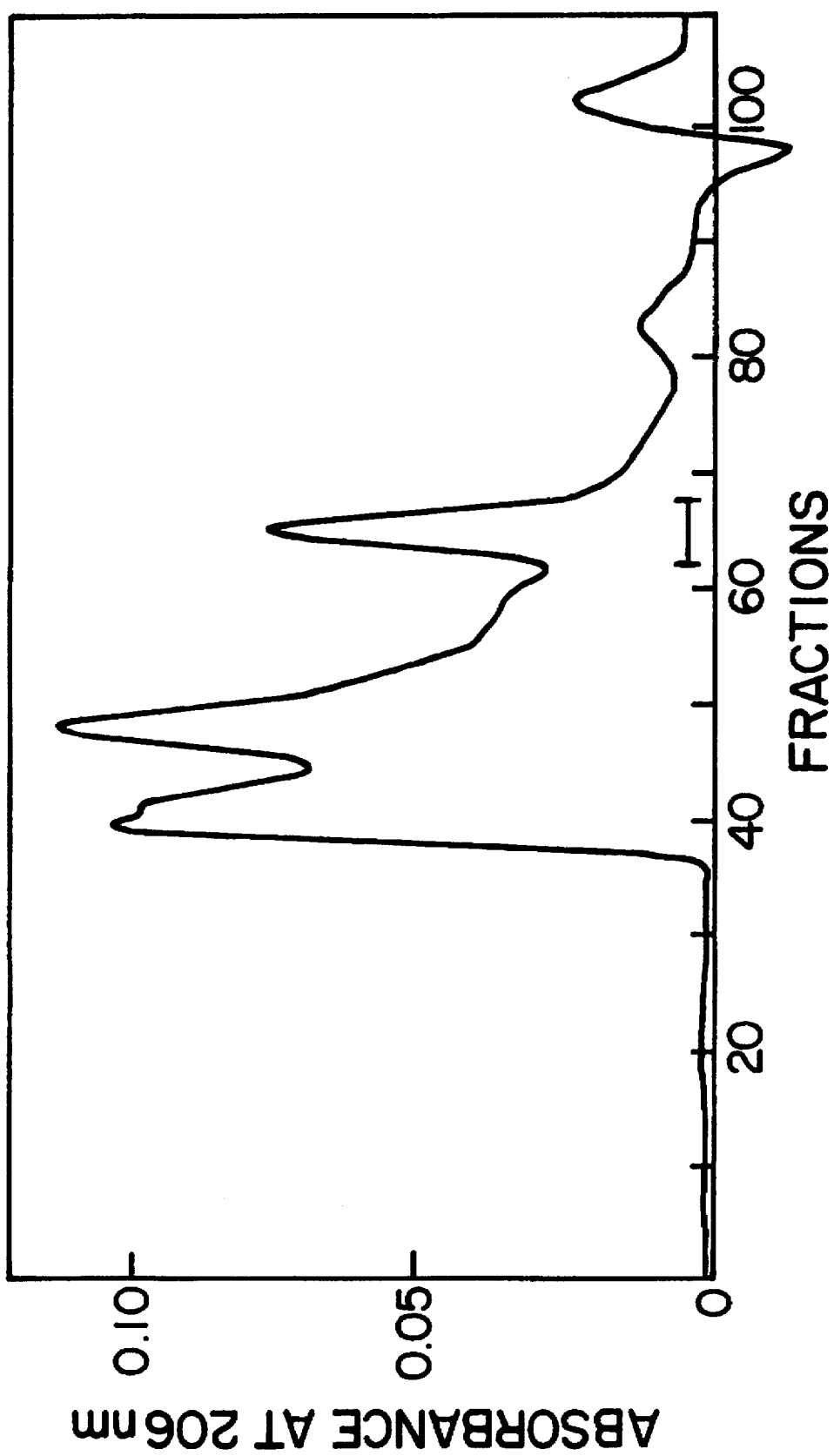

FIG. 15. Elution profile for high pressure liquid chromatography (HPLC) of factor VIII on a Toya Soda TSK 4000 SW column. The column was equilibrated and developed at room temperature with 0.1 percent SDS in 0.1M sodium phosphate, pH 7.0.

Figure 16:
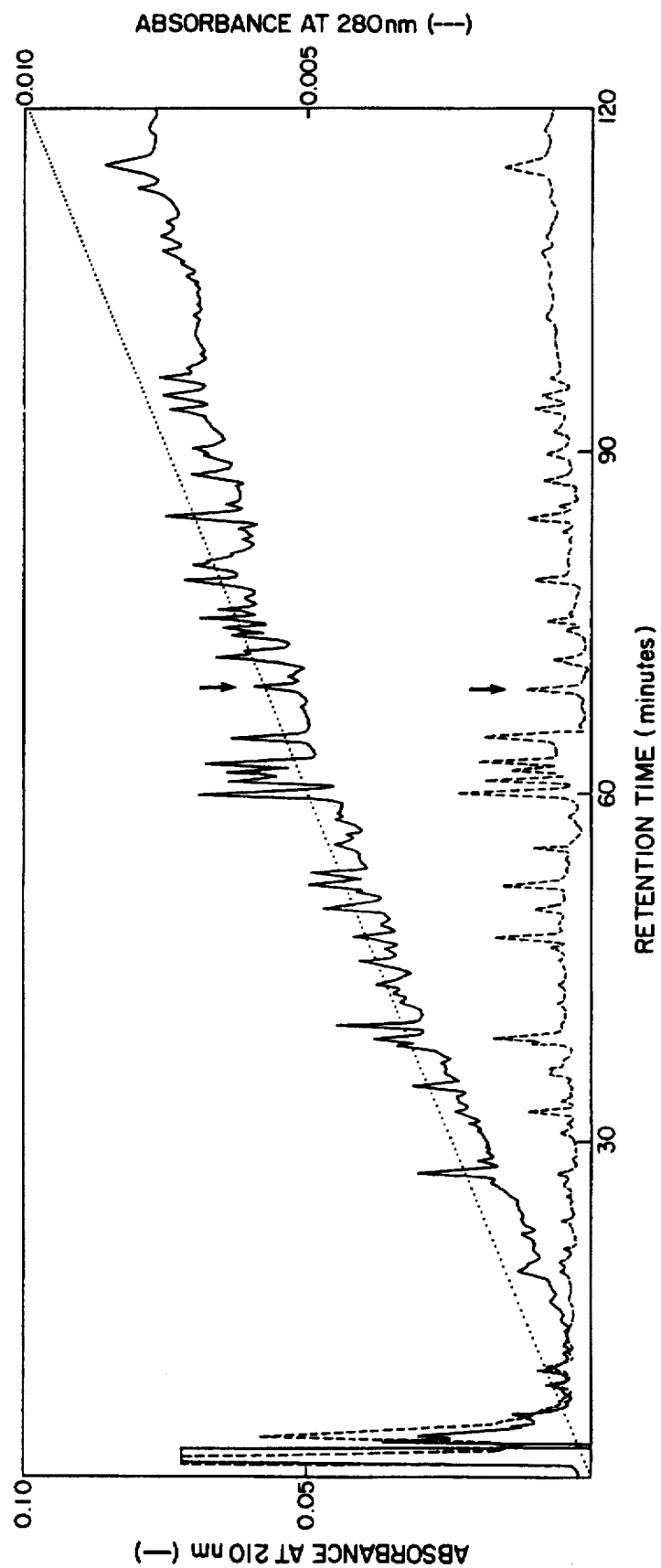

FIG. 16. Elution profile for reverse phase HPLC separation of factor VIII tryptic peptides. The separation was performed on a Synchropak RP-P C-18 column (0.46 cm×25 cm, 10 microns) using a gradient elution of acetonitrile (1 percent to 70 percent in 200 minutes) in 0.1 percent trifluoroacetic acid. The arrow indicates the peak containing the peptide with the sequence AWAYFSDVDLEK.

Figure 17:
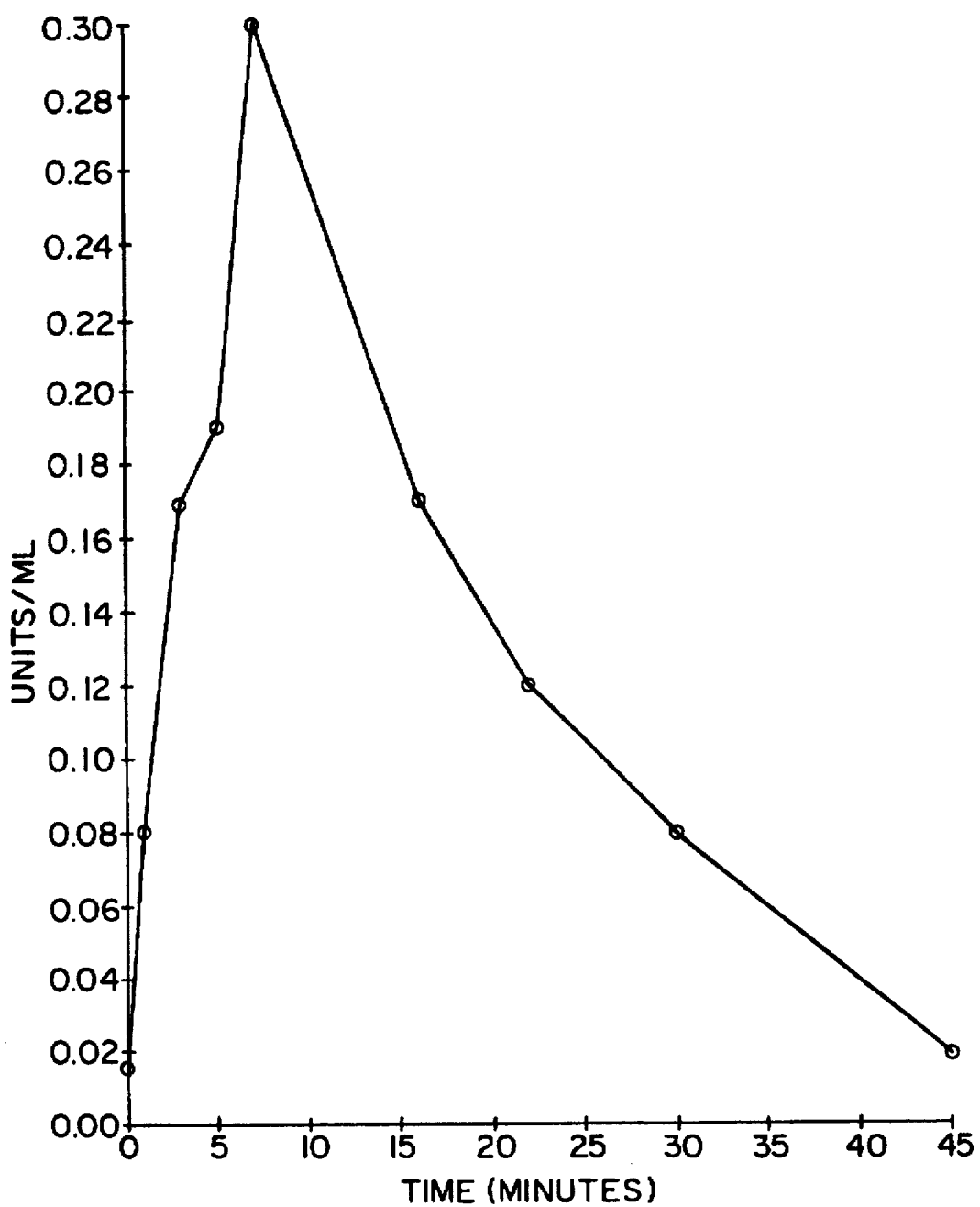

FIG. 17. Thrombin activation of purified factor VIII activity. The cell supernatant was chromatographed on the C8 monoclonal resin, and dialyzed to remove elution buffer. Thrombin (25ng) was added at time 0. Aliquots were diluted 1:3 at the indicated times and assayed for coagulant activity. Units per ml were calculated from a standard curve of normal human plasma.

DETAILED DESCRIPTION

A. Definitions

As used herein, "human factor VIII" denotes a functional protein capable, in vivo or in vitro, of correcting human factor VIII deficiencies, characterized, for example, by hemophilia A. The protein and associated activities are also referred to as factor VIIIC (FVIIIC) and factor VIII coagulant antigen (FVIIICAg)(31a). Such factor VIII is produced by recombinant cell culture systems active form(s) corresponding to factor VIII activity native to human plasma. (One "unit" of human factor VIII activity has been defined as that activity present in one milliliter of normal human plasma.) The factor VIII protein produced herein is defined by means of determined DNA gene and amino acid sequencing, by physical characteristics and by biological activity.

Factor VIII has multiple degradation or processed forms in the natural state. These are proteolytically derived from a precursor, one chain protein, as demonstrated herein. The present invention provides such single chain protein and also provides for the production per se or via in vitro processing of a parent molecule of these various degradation products, and administration of these various degradation products, which have been shown also to be active. Such products contain functionally active portion(s) corresponding to native material.

Allelic variations likely exist. These variations may be demonstrated by one or more amino acid differences in the overall sequence or by deletions, substitutions, insertions or inversions of one or more amino acids in the overall sequence. In addition, the location of and degree of glycosylation may depend on the nature of the host cellular environment. Also, the potential exists, in the use of recombinant DNA technology, for the preparation of various human factor VIII derivatives, variously modified by resultant single or multiple amino acid deletions, substitutions, insertions or inversions, for example, by means of site directed mutagenesis of the underlying DNA. In addition, fragments of human factor VIII, whether produced in vivo or in vitro, may possess requisite useful activity, as discussed above. All such allelic variations, glycosylated versions, modifications and fragments resulting in derivatives of factor VIII are included within the scope of this invention so long as they contain the functional segment of human factor VIII and the essential, characteristic human factor VIII functional activity remains unaffected in kind. Such functional variants or modified derivatives are termed "human factor VIII derivatives" herein. Those derivatives of factor VIII possessing the requisite functional activity can readily be identified by straightforward in vitro tests described herein. From the disclosure of the sequence of the human factor VIII DNA herein and the amino acid sequence of human factor VIII, the fragments that can be derived via restriction enzyme cutting of the DNA or proteolytic or other degradation of human factor VIII protein will be apparent to those skilled in the art.

Thus, human factor VIII in functional form, i.e., "functional human factor VIII", is capable of catalyzing the conversion of factor X to Xa in the presence of factor IXa, calcium, and phospholipid, as well as correcting the coagulation defect in plasma derived from hemophilia A affected individuals, and is further classified as "functional human factor VIII" based on immunological properties demonstrating identity or substantial identity with human plasma factor VIII.

"Essentially pure form" when used to describe the state of "human factor VIII" produced by the invention means substantially free of protein or other materials ordinarily associated with factor VIII when isolated from non-recombinant sources, i.e. from its "native" plasma containing environment.

"DHFR protein" refers to a protein which is capable of exhibiting the activity associated with dihydrofolate reductase (DHFR) and which, therefore, is required to be produced by cells which are capable of survival on medium deficient in hypoxanthine, glycine, and thymidine (−HGT medium). In general, cells lacking DHFR protein are incapable of growing on this medium, and cells which contain DHFR protein are successful in doing so.

"Expression vector" includes vectors which are capable of expressing DNA sequences contained therein, where such sequences are operably linked to other sequences capable of effecting their expression. These expression vectors replicate in the host cell, either by means of an intact operable origin of replication or by functional integration into the cell chromosome. Again, "expression vector" is given a functional definition, and any DLA sequence which is capable of effecting expression of a specified DNA code disposed therein is included in this term as it is applied to the specified sequence. In general, expression vectors of utility in recombinant DNA techniques are often in the form of "plasmids" which refer to circular double stranded DNA loops. However, the invention is intended to include such other forms of expression vectors which serve equivalent functions.

"DNA isolate" means the DNA sequence comprising the sequence encoding human factor VIII, either itself or as incorporated into a cloning vector.

"Recombinant host cell" refers to cell/cells which have been transformed with vectors constructed using recombinant DNA techniques. As defined herein, factor VIII or functional segments thereof are produced in the amounts achieved by virtue of this transformation, rather than in such lesser amounts, and degrees of purity, as might be produced by an untransformed, natural host source. Factor VIII produced by such "recombinant host cells" can be referred to as "recombinant human factor VIII".

Size units for DNA and RNA are often abbreviated as follows: b=base or base pair; kb=kilo (one thousand) base or kilobase pair. For proteins we abbreviate: D=Dalton; kD=kiloDalton. Temperatures are always given in degrees Celsius.

B. Host Cell Cultures and Vectors

Useful recombinant human factor VIII may be produced, according to the present invention, in a variety of recombinant host cells. A particularly preferred system is described herein.

In general, prokaryotes are preferred for cloning of DNA sequences in constructing the vectors useful in the invention. For example, E. coli K12 strain 294 (ATCC No. 31446) is particularly useful. Other microbial strains which may be used include E. coli strains such as E. coli B, and E. coli X1776 (ATTC No. 31537), and E. coli c600 and c600hfl, E. coli W3110 (F⁻, λ⁻, prototrophic, ATTC No. 27325), bacilli such as Bacillus subtilus, and other enterobacteriaceae such as Salmonella typhimurium or Serratia marcesans, and various pseudomonas species. These examples are, of course, intended to be illustrative rather than limiting.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species (32). pBR322 contains genes for ampicillin and tetracycline resistance and thus provides easy means for identifying and selecting transformed cells. The pBR322 plasmid, or other microbial plasmid, must also contain, or be modified to contain, promoters which can be used by the microbial organism for expression of its own proteins. Those promoters most commonly used in recombinant DNA construction include the β-lactamase (penicillinase) and lactose promoter systems (33–35) and a tryptophan (trp) promoter system (36, 37). While these are the most commonly used, other microbial promoters have been discovered and utilized, and details concerning their nucleotide sequences have been published, enabling a skilled worker to ligate them functionally with plasmid vectors (38).

In addition to prokaryotes, eukaryotic microbes, such as yeast cultures, may also be used. *Saccharomyces cerevisiae*, or common baker's yeast, is the most commonly used among eukaryotic microorganisms, although a number of other strains are commonly available. For expression in Saccharomyces, the plasmid YRp7, for example, (39–41) is commonly used. This plasmid already contains the trp1 gene which provides a selection marker for a mutant strain of yeast lacking the ability to grow in tryptophan, for example, ATCC No. 44076 or PEP4-1 (42). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (43) or other glycolytic enzymes (44, 45), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions, are the promoter regions for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

Use of cultures of cells derived from multicellular organisms as cell hosts is preferred, particularly for expression of underlying DNA to produce the functional human factor VIII hereof, and reference is particularly had to the preferred embodiment hereof. In principle, vertebrate cells are of particular interest, such as VERO and HeLa cells, Chinese hamster ovary (CHO) cell lines, and W138, BHK, COS-7 and MDCK cell lines. Expression vectors for such cells ordinarily include (if necessary) (an) origin(s) of replication, a promoter located in front of the gene to be expressed, along with any necessary ribosome binding sites, RNA splice sites, polyadenylation site, and transcriptional terminator sequences.

For use in mammalian cells, the control functions on the expression vectors may be provided by viral material. For example, commonly used promoters are derived from polyoma, Simian Virus 40 (SV40) and most particularly Adenovirus 2. The early and late promoters of SV40 virus are useful as is the major late promoter of adenovirus as described above. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from adenovirus or other viral (e.g. Polyoma, SV40, VSV, BPV, etc.) source, or may be provided by the host cell chromosomal replication mechanism, if the vector is integrated into the host cell chromosome.

In selecting a preferred host cell for transfection by the vectors of the invention which comprise DNA sequences encoding both factor VIII and DHFR protein, it is appropriate to select the host according to the type of DHFR protein employed. If wild type DHFR protein is employed, it is preferable to select a host cell which is deficient in DHFR, thus permitting the use of the DHFR coding sequence as a marker for successful transfection in selective medium which lacks hypoxanthine, glycine, and thymidine.

On the other hand, if DHFR protein with low binding affinity for MTX is used as the controlling sequence, it is not necessary to use DHFR resistant cells. Because the mutant DHFR is resistant to methotrexate, MTX containing media can be used as a means of selection provided that the host cells themselves are methotrexate sensitive. Most eukaryotic cells which are capable of absorbing MTX appear to be methotrexate sensitive.

Alternatively, a wild type DHFR gene may be employed as an amplification marker in a host cell which is not deficient in DHFR provided that a second drug selectable marker is employed, such as neomycin resistance.

Examples which are set forth hereinbelow describe use of BHK cells as host cells and expression vectors which include the adenovirus major late promoter.

C. General Methods

If cells without formidable cell wall barriers are used as host cells, transfection is carried out by the calcium phosphate precipitation method (46). However, other methods for introducing DNA into cells such as by nuclear injection or by protoplast fusion may also be used.

If prokaryotic cells or cells which contain substantial cell wall constructions are used, the preferred method of transfection is calcium treatment using calcium chloride (47).

Construction of suitable vectors containing the desired coding and control sequences employs standard ligation techniques. Isolated plasmids or DNA fragments are cleaved, tailored, and religated in the form desired to form the plasmids required.

Cleavage is performed by treating with restriction enzyme (or enzymes) in suitable buffer. In general, about 1 μg plasmid or DNA fragments are used with about 1 unit of enzyme in about 20 μl of buffer solution for 1 hour. (Appropriate buffers and substrate amounts for particular restriction enzymes are specified by the manufacturer. Likewise, standard conditions for use of T4 ligase, T4 polynucleotide kinase and bacterial alkaline phosphatase are provided by the manufacturer.) After incubations, protein is removed by extraction with phenol and chloroform, and the nucleic acid is recovered from the aqueous fraction by precipitation with ethanol. Standard laboratory procedures are available (48).

Sticky ended (overhanging) restriction enzyme fragments are rendered blunt ended, for example, by either:

Fill in repair: 2–15 μg of DNA were incubated in 50 mM NaCl , 10 mM Tris (pH 7.5), 10 mM $MgCl_2$, 1 mM dithiothreitol with 250 µM each four deoxynucleoside triphosphates and 8 units DNA polymerase Klenow fragment at 24° C. for 30 minutes. The reaction was terminated by phenol and chloroform extraction and ethanol precipitation, or S1 digestion: 2–15 µg of DNA were incubated in 25 mM NaOAc (pH 4.5), 1 mM $ZnCl_2$, 300 mM NaCl with 600 units $S_1$ nuclease at 37° for 30 minutes, followed by phenol, chloroform and ethanol precipitation.

Synthetic DNA fragments were prepared by known phosphotriester (47a) or phosphoramidite (47b) procedures. DNA is subject to electrophoresis in agarose or polyacrylamide slab gels by standard procedures (48) and fragments were purified from gels by electroelution (48a). DNA "Southern" blot hybridization followed the (49a) procedure.

RNA "Northern" blot hybridizations followed electrophoresis in agarose slab gels containing 6 percent formaldehyde. (48, 49b) Radiolabeled hybridization probes are prepared by random calf thymus DNA primed synthesis (49c) employing high specific activity $^{32}$P-labeled nucleotide triphosphates ($^{32}$P: Amersham; Klenow DNA polymerase: BRL, NEB or Boehringer-Mannheim). Short oligonucleotide probes may be end-labelled with T4 polynucleotide kinase. "Standard salt" Southern hybridization conditions ranged from: Hybridization in 5× SSC (1× SSC=0.15M NaCl 0.015M $Na_3$ citrate), 50 mM Na Phosphate pH 7, 10 percent dextran sulfate, 5× Denhardt's solution (1× Denhardt's=0.02 percent ficoll, 0.02 percent polyvinylpyrrolidone, 0.02 percent bovine serum albumin), 20–100 µg/ml denatured salmon sperm DNA, 0–50 percent formamide at temperatures ranging from 24° to 42° C., followed by washes in 0.2–1× SSC plus 0.1 percent SDS at temperatures ranging from 24°–65° C. Dried filters were exposed to Kodak XAR film using DuPont Lightning-Plus intensifying screens at −80° C. See, generally, (48).

For Northern blot screening of cell and tissue RNAs, hybridization was in 5× SSC, 5× Denhardt's solution, 10 percent dextran sulfate, 50 percent formamide, 0.1 percent SDS, 0.1 percent sodium pyrophosphate, 0.1 mg/ml *E. coli* tRNA at 42° C. overnight with $^{32}$P-labeled probe prepared from the 189 bp StuI/HincI fragment of λ120 containing exon A sequence. Wash conditions were 0.2× SSC, 0.1 percent SDS at 42° C.

Human DNA was prepared from peripheral blood lymphocytes (46,XY) or lymphoblast cells (49,XXXXY, N.I.G.M.S. Human Genetic Mutant Cell Repository, Camden, N.J., No. GM1202A) (48). *E. coli* plasmid DNA was prepared as in (48) and bacteriophage λ DNA (48). Tissue RNA was prepared by either the guanidinium thiocyanate method (48, 49f) or the method of (49b). Polyadenylated RNA was isolated on oligo (dT) cellulose (49h).

DNA sequence analysis was performed by the method of (49i).

For the λ/4X library, five 50 µg aliquots of the 49, XXXXY DNA was digested in a 1 ml volume with Sau3AI concentrations of 3.12, 1.56, 0.782, 0.39, and 0.195 U/ml for 1 hr at 37° C. Test digestion and gel analysis had shown that under these conditions at 0.782 U/ml Sau3AI, the weight average size of the DNA was about 30 kb; thus these digests generate a number average distribution centered at 15 kb. DNA from 5 digests was pooled, phenol and chloroform extracted, ethanol precipitated and electrophoresed on a 6 g/l low-gelling temperature horizontal agarose gel (48) (Seaplaque agarose, FMC Corporation), in two 5.6×0.6× 0.15 cm slots. The 12–18 kb region of the gel was cut out and the DNA purified by melting the gel slice as described in (48).

Charon 30 arms were prepared by digesting 50 µg of the vector with BamHI and isolating the annealed 31.9 kb arm fragment from a 6 g/l low-gelling temperature agarose gel as described above. For construction of the λ/4X library, the optimal concentration of Charon 30 BamHI arms and 12–18 kb Sau3A partial 49,XXXXY DNA was determined as described (48). The ligated DNA was packaged with an in vitro extract, "packagene" (Promega Biotec, Inc., Madison, Wis.). In a typical reaction about 1.3 µg of Charon 30 BamHI arms were ligated to 0.187 µg of 12–18 kb Sau3A insert DNA in a 10 µl volume. Packaging the plating of the DNA gave about $1.3 \times 10^6$ phage plaques. To generate the λ4X library, $1.7 \times 10^6$ phage were plated at 17000 phage per 150 cm plate. These plates were grown overnight, scraped into 10 mM Tris HCl, pH 7.5, 0.1M NaCl, 10 mM $MgCl_2$, 0.5 g/l gelatin, and centrifuged briefly, to amplify the phage. Generally, a suitable number ($0.5–2 \times 10^6$) of these phage were plated out and screened (48). In some cases the ligated and in vitro packaged phage were screened directly without amplification.

For the isolation of λ482, a clone containing a 22 kb BclII fragment of the Factor VIII genome, and the BamHI arm fragments of the vector λ1059 (49) were isolated by gel electrophoresis. Separately, 100 µg of DNA from the 49,XXXXY cell line was digested with BclII and the 20–24 kb fraction isolated by gel electrophoresis. About 0.8 µg of λ1059 arms fragments and 5 percent of the isolated BclII DNA were ligated in a volume of 10 µl (48) to generate 712,000 plaques. Four hundred thousand of those were screened in duplicate with 2.2 kb StuI/EcoRI probe of λ114.

The cosmid/4X library was generated from the 49,XXXXY DNA used to generate the λ/4X library, except that great care was used in the DNA isolation to avoid shearing or other breakage. The DNA was partially cleaved with five concentrations of Sau3AI and the pooled DNA sized on a 100 to 400 g/l sucrose gradient (49). The fractions containing 35–45 kb DNA were pooled, dialyzed, and ethanol precipitated. Arm fragments of the cosmid vector pGcos4 were prepared following the principles described elsewhere (50). In brief, two separate, equal aliquots of pGcos4 were cut with SstI (an isoschizomer of SacI) or SalI and then treated with bacterial alkaline phosphatase. These aliquots were then phenol and chloroform extracted, pooled, ethanol precipitated and cut with BamHI. From this digest two arm fragments of 4394 and 4002 b were isolated from a low-gelling temperature agarose gel. These arm fragments were then ligated to the isolated, 40 kb Sau3AI partial digest DNA. In a typical reaction, 0.7 µg of pGcos4 arm fragments were ligated to 1 µg of 40 kb human 4X DNA in a volume of 10 µl (48). This reaction was then packaged in vitro and used to infect *E. coli* HB101, a recA$^{31}$ strain (48). This reaction generated about 120,000 colonies when plated on tetracycline containing plates. About 150,000 cosmids were screened on 20 150-mm plates in duplicate as described, with overnight amplification on chloramphenicol-containing plates (48).

Double-stranded cDNA was prepared as previously described (36, 67) employing either oligo(dT)12–18 or synthetic deoxyoligonucleotide 16-mers as primers for first-strand synthesis by reverse transcriptase. Following isolation by polyacrylamide gels, cDNA of the appropriate size (usually 600 bp or greater) was either C-tailed with terminal transferase, annealed together with G-tailed PstI-digested pBR322 and transformed into *E. coli* strain DH1 (76), or ligated with a 100-fold molar excess of synthetic DNA EcoRI adaptors, reisolated on a polyacrylamide gel, inserted by ligation in EcoRI-digested λGT10, packaged into phage particles and propagated on *E. coli* strain C600hfl (68). As a modification of existing procedures an adaptor consisting of a complementary synthetic DNA 18-mer and 22-mer (5'-CCTTGACCGTAAGACATG and 5'AATTCATGTCTTACGGTCAAGG) was phosphorylated at the blunt terminus but not at the EcoRI cohesive terminus to permit efficient ligation of the adaptor to double-stranded cDNA in the absence of extensive self-ligation at the EcoRI site. This effectively substituted for the more laborious procedure of ligating self-complementary EcoRI linkers to EcoRI methylase-treated double-stranded cDNA, and subsequently removing excess linker oligomers from the cDNA termini by EcoRI digestion. To improve the efficiency of obtaining cDNA clones >3500 bp extending from the poly (A) to the nearest existing 3' factor VIII probe sequences made available by genomic cloning (i.e., exon A), second-strand cDNA synthesis was specifically primed by including in the reaction a synthetic DNA 16-mer corresponding to a sequence within exon B on the mRNA sense strand.

D. Adenovirus Subcloning

Adenovirus 2 DNA was purchased from Bethesda Research Laboratories (BRL). The viral DNA was cleaved with HindIII and electrophoresed through a 5 percent polyacrylamide gel (TBE buffer). The region of the gel containing the HindIII B fragment (49j) was excised and the DNA electroeluted from the gel. After phenol-chloroform extraction, the DNA was concentrated by ethanol precipitation and cloned into HindIII-cleaved pUC13 (49k) to generate the plasmid pAdHindB. This HindIII subclone was digested with HindIII and SalI, and a fragment was isolated spanning adenoviral coordinates 17.1–25.9 (49j). This fragment was cloned into HindIII, SalI cleaved pUC13 to generate the plasmid pUCHS. From pAdHindB the SalI to XhoI fragment, coordinates 25.9–26.5, was isolated and cloned into pUCHS at the unique SalI site to create pUCHSX. This plasmid reconstructs the adenoviral sequences from position 17.1 within the first late leader intervening sequence to the XhoI site at position 26.5 within the third late leader exon.

The adenovirus major late promoter was cloned by excising the HindIII C, D, and E fragments (which comigrate) from the acrylamide gel, cloning them into pUC13 at the HindIII site, and screening for recombinants containing the HindIII C fragment by restriction analysis. This subclone was digested with SacI, which cleaved at position 15.4, 5' of the major late promoter (49j) as well as within the polylinker of pUC13. The DNA was recircularized to form pMLP2, containing the SacI to HindIII fragment (positions 15.4–17.1) cloned in the SacI and HindIII sites of pUC13.

E. Construction of Neomycin Resistance Vector

The neomycin resistance marker contained within *E. coli* transposon 5 was isolated from a Tn5 containing plasmid (49l). The sequence of the neomycin resistance gene has been previously published (49m). The neo fragment was digested with BglII, which cleaves at a point 36 bp 5' of the translational initiation codon of the neomycin phosphotransferase gene, and treated with exonuclease Bal31. The phosphotransferase gene was excised with BamHI, which cleaves the DNA 342 bp following the translational termination codon, and inserted into pBR322 between a filled-in HindIII site and the BamHI site. One clone, pNeoBal6, had the translational initiation codon situated 3 bp 3' of the filled in HindIII site (TCATCGATAAGCTCGCATG . . . ). This plasmid was digested with ClaI and BamHI, whereupon the 1145 bp fragment spanning the phosphotransferase gene was isolated and inserted into the mammalian expression vector pCVSVEHBS (see infra.). The resultant plasmid, pSVENeoBa16, situates the neomycin phosphotransferase gene 3' of the SV40 early promoter and 5' of the polyadenylation site of the HBV surface antigen gene (49n). When introduced into mammalian tissue culture cells, this plasmid is capable of expressing the phosphotransferase gene and conferring resistance to the aminoglycoside G418 (49o).

F. Transfection of Tissue Culture Cells

The BHK-21 cells (ATCC) are vertebrate cells grown in tissue culture. These cells, as is known in the art, can be maintained as permanent cell lines prepared by successive serial transfers from isolated normal cells. These cell lines are maintained either on a solid support in liquid medium, or by growth in suspensions containing support nutrients.

The cells are transfected with 5 μg of desired vector (4 μg pAML3P.8cl and 1 μg pSVEneoBal6) as prepared above using the method of (49p).

The method insures the interaction of a collection of plasmids with a particular host cell, thereby increasing the probability that if one plasmid is absorbed by a cell, additional plasmids would be absorbed as well (49q). Accordingly, it is practicable to introduce both the primary and secondary coding sequences using separate vectors for each, as well as by using a single vector containing both sequences.

G. Growth of Transfected Cells and Expression of Peptides

The BHK cells which were subjected to transfection as set forth above were first grown for two days in non-selective medium, then the cells were transferred into medium containing G418 (400 μg/ml), thus selecting for cells which are able to express the plasmid phosphotransferase. After 7–10 days in the presence of the G418, colonies became visible to the naked eye. Trypsinization of the several hundred colonies and replating allowed the rapid growth of a confluent 10 cm dish of G418 resistant cells.

This cell population consists of cells representing a variety of initial integrants. In order to obtain cells which possessed the greatest number of copies of the FVIII expression plasmid, the cells were next incubated with an inhibitor of the DHFR protein.

H. Treatment with Methotrexate

The G418 resistant cells are inhibited by methotrexate (MTX), a specific inhibitor of DHFR at concentrations greater than 50 nN. Consistent with previous studies on the effects of MTX on tissue culture cells, cells resistant to MTX by virtue of expression of the multiple copies of the DHFR gene contained within the FVIII expression vector are selected for, and a concomitant increase in expression of the FVIII encoding sequences can be observed. By stepwise increasing the amount of MTX, amplification of the plasmid pAML3P.8cl is affected, thus increasing the copy number. The upper limit of the amplification is dependent upon many factors, however cells resistant to millimolar concentrations of MTX possessing hundreds or thousands of copies of the DHFR expression (and thus the FVIII expression) plasmid may be selected in this manner.

For Factor VIII expression, G418-resistant BHK cells which arose after transfection with pAML3P.8cl and pSVE-NeoBa16 were incubated with media containing 100 nM and 250 nM NTX as described (49r). After 7–10 days, cells resistant to 250 nM MTX were assayed for Factor VIII expression by activity, radioimmunoassay and mRNA Northern analysis.

I. Factor VIII antibodies

A variety of polyclonal and monoclonal antibodies to Factor VIII were used throughout this work. CC is a polyclonal antibody derived from the plasma of a severely affected hemophiliac (49s). C8 is a neutralizing monoclonal antibody which binds to the 210 kD portion of Factor VIII (49t). C10 is a monoclonal antibody with properties similar to C8 and was isolated essentially as described by (49t). A commercial neutralizing monoclonal antibody which binds the 80 kD portion of Factor VIII was obtained from Synbiotic Corp., San Diego, Calif., Product No. 10004. C7F7 is a neutralizing monoclonal antibody that binds to the 80 kD portion of Factor VIII. C7F7 was induced and purified as follows: Six-week-old female BALB/c mice were multiply inoculated with approximately 10 µg of purified Factor VIII and splenocytes fused with X63-Ag8.653 mouse myeloma cells (49u) three days after the final inoculation. The hybridization procedure and isolation of hybrid cells by cloning methods followed previously described protocols (49r). Specific antibody producing clones were detected by solid phase RIA procedures (49w). Positive clones were subsequently assayed for coagulation prolongation capacity by APTT assay described above. Monoclonal C7F7 was expanded by growth in syngeneic animals; antibody was purified from ascites fluids by protein A-Sepharose CL-4B chromatography (49x).

J. Radioimmune Assays for Factor VIII

Two radioimmune assays (RIA) were developed to assay Factor VIII produced from BHK and other cell lines. Both are two stage assays in which the CC antibody bound to a solid support is used to bind Factor VIII (49t). This immune complex is then detected with $I^{125}$ labeled C10 antibody (210 kD specific) or $I^{125}$ labeled C7F7 antibody (80 kD specific).

Briefly, the two-stage RIAs are performed as follows: the 96 wells of a microtiter dish are coated overnight with 100 µl of 50 mM $NaHCO_3$ buffer, pH 9.6 containing 2.5 mg/l of CC antibody which has been purified by protein A-sepharose chromatography (49x). The wells are washed three times with 200 µl of PBS containing 0.05 percent Tween 20 and blocked with 200 µl of PBS containing 0.1 percent gelatin and 0.01 percent methiolate for 1 to 2 hours. The wells are washed as before and 100 µl of sample added and incubated overnight. The wells are washed and 100 µl of $I^{125}$ labeled (82) C10 or C7F7 antibody (1000 cpm/µl ) added and incubated 6 to 8 hours. The wells are washed again and counted. The standard curve is derived from samples of normal plasma diluted 1:10 to 1:320.

K. Factor VIII Monoclonal Antibody Column

A human factor VIII monoclonal antibody column was prepared by incubation of 1.0 mg of C8 antibody (in 0.1M $NaHCO_3$, pH8.5) with 1.0 ml of Affi-Gel 10 (Bio-Rad Laboratories, Richmond, Calif.) for four hours at 4° C. Greater than 95 percent of the antibody was coupled to the gel, as determined by the Bio-Rad Protein Assay (Bio-Rad Laboratories). The gel was washed with 50 volumes of water and 10 volumes of 0.5M imidazole, pH6.9, containing 0.15M NaCl.

L. Chromatography of Media on Monoclonal Column

Media was applied to the monoclonal antibody column (1 ml of resin) and washed with 0.05M imidazole buffer, pH6.4, containing 0.15M NaCl until material absorbing at 280 nm was washed off. The column was eluted with 0.05M imidazole, pH6.4, containing 1.0M KI and 20 percent ethylene glycol. Samples were diluted for assay and dialized for subsequent analysis.

M. Preparation of Factor VIII Fusion Proteins and Fusion Protein Antisera

E. coli containing the plasmids constructed for fusion protein expression were grown in M-9 media at 37° C. Fusion protein expression was induced by the addition of indole acrylic acid at a final concentration of 50 µg/mL for time periods of 2.5 to 4 hours. The cells were harvested by centrifugation and frozen until use.

The cell pellets for fusion 3 were suspended in 100 mL of 20 mM sodium phosphate, pH 7.2, containing 10 µg/mL lysozyme and 1 µg/mL each of RNase and DNase. The suspension was stirred for 30 minutes at room temperature to thoroughly disperse the cell pellet. The suspension was then sonicated for four minutes (pulsed at 60 percent power). The solution was centrifuged at 8000 rpm in a Sorvall RC-2B centrifuge in a GSA rotor. The pellet was resuspended n 100 mL of 0.02M sodium phosphate, pH 7.2. The suspension was layered over 300 mL of 60 percent glycerol. The sample was centrifuged at 4000 rpm for 20 minutes in an RC-3B centrifuge. Two layers resulted in the glycerol. Both pellet and the bottom glycerol layer showed a single protein band of the expected molecular weight of 25,000 daltons when analyzed on SDS polyacrylamide gels. The pellet was dissolved in 0.02M sodium phosphate buffer containing 0.1 percent SDS. The resuspended pellet and the lower glycerol layer were dialyzed against 0.02M ammonium bicarbonate, pH 8.0, to remove glycerol. The solution was lyophilized and redissolved in 0.01M sodium phosphate buffer containing 0.1 percent SDS, and frozen until use.

The cell pellets for fusion proteins 1 and 4 were suspended in 0.05M Tris, pH 7.2, containing 0.3M sodium chloride and 5 mM EDTA. Lysozyme was added to a concentration of 10 µg/mL. Samples were incubated for 5 minutes at room temperature. NP-40 was added to 0.2 percent and the suspension incubated in ice for 30 minutes. Sodium chloride was added to yield a final concentration of 3M and DNase added (1 µg/mL). The suspension was incubated 5 minutes at room temperature. The sample was centrifuged and the supernatant discarded. The pellet was resuspended in a small volume of water and recentrifuged. The cell pellets were dissolved in solutions containing 0.1 percent to 1 percent SDS and purified by either preparative SDS polyacrylamide gel electrophoresis followed by electroelution of the fusion protein band, or by HPLC on a TSK 3000 column equilibrated with 0.1M sodium phosphate containing 0.1 percent SDS.

Rabbit antisera was produced by injecting New Zealand white rabbits with a sample of fusion protein suspended in Freund's complete adjuvant (first injection) following by boosts at two week intervals using the sample suspended in Freund's incomplete adjuvant. After six weeks, sera was obtained and analyzed by Western Blot analysis for reactivity with human plasma derived factor VIII proteins.

N. Assays for Detection of Expression of Factor VIII Activity

Correction of Hemophilia A plasma—Theory—Factor VIII activity is defined as that activity which will correct the coagulation defect of factor VIII deficient plasma. One unit of factor VIII activity has been defined as that activity present in one milliliter of normal human plasma. The assay is based on observing the time required for formation of a visible fibrin clot in plasma derived from a patient diagnosed as suffering from hemophilia A (classic hemophilia). In this assay, the shorter the time required for clot formation, the greater the factor VIII activity in the sample being tested. This type of assay is referred to as activated partial thromboplastin time (APTT). Commercial reagents are available for such determinations (for example, General Diagnostics Platelin Plus Activator; product number 35503).

Procedure—All coagulation assays were conducted in 10×75 mm borosilicate glass test tubes. Siliconization was performed using SurfaSil (product of Pierce Chemical Company, Rockford, Ill.) which had been diluted 1 to 10 with petroleum ether. The test tubes were filled with this solution, incubated 15 seconds, and the solution removed. The tubes were washed three times with tap water and three times with distilled water.

Platelin Plus Activator (General Diagnostics, Morris Plains, N.J.) was dissolved in 2.5 ml of distilled water according to the directions on the packet. To prepare the sample for coagulation assays, the Platelin plus Activator solution was incubated at 37° C. for 10 minutes and stored on ice until use. To a siliconized test tube was added 50 microliters of Platelin plus Activator and 50 microliters of factor VIII deficient plasma (George King Biomedical Inc, Overland Park, Kans.). This solution was incubated at 37° C. for a total of nine minutes. Just prior to the end of the nine minute incubation of the above solution, the sample to be tested was diluted into 0.05M Tris-HCl, pH 7.3, containing 0.02 percent bovine serum albumin. To the plasma/activator suspension was added 50 microliters of the diluted sample, and, at exactly nine minutes into the incubation of the suspension, the coagulation cascade was initiated by the addition of 50 microliters of calcium chloride (0.033M). The reaction mixture was quickly mixed and, with gentle agitation of the test tube, the time required for the formation of a visible fibrin clot to form was monitored. A standard curve of factor VIII activity can be obtained by diluting normal plasma (George King Biomedical, Inc., Overland Park, Kans.) 1:10, 1:20, 1:50, 1:100, and 1:200. The clotting time is plotted versus plasma dilution on semilog graph paper. This can then be used to convert a clotting time into units of factor VIII activity.

O. Chromogenic Peptide Determination

Theory—Factor VIII functions in the activation of factor X to factor $X_a$ in the presence of factor $IX_a$, phospholipid, and calcium ions. A highly specific assay has been designed wherein factor $IX_a$, factor X, phospholipid, and calcium ions are supplied. The generation of factor $X_a$ in this assay is therefore dependent upon the addition of a source of factor VIII activity. The more factor VIII added to the assay, the more factor $X_a$ is generated. After allowing the generation of factor $X_a$, a chromogenic peptide substrate is added to the reaction mixture. This peptide is specifically cleaved by factor $X_a$, is not effected by factor X, and is only slowly cleaved by other proteases. Cleavage of the peptide substrate releases a para-nitro-anilide group which has absorbance at 405 nm, while the uncleaved peptide substrate has little or no absorbance at this wavelength. The generation of absorbance due to cleavage of the chromogenic substrate is dependent upon the amount of factor $X_a$ in the test mixture after the incubation period, the amount of which is in turn dependent upon the amount of functional factor VIII in the test sample added to the reaction mixture. This assay is extremely specific for factor VIII activity and should be less subject to potential false positives when compared to factor VIII deficient plasma assay.

Procedure—Coatest factor VIII was purchased from Helena Laboratories, Beaumont, Tex. (Cat. No. 5293). The basic procedure used was essentially that provided by the manufacturer for the "End Point Method" for samples containing less than 5 percent factor VIII. Where indicated, the times of incubation were prolonged in order to make the assay more sensitive. For certain assays the volumes of reagents recommended by the manufacturer were altered. This change in the protocol does not interfere with the overall results of the assay.

The chromogenic substrate (S-2222+I-2581) for factor $X_a$ was dissolved in 10 milliliters of water, resulting in a substrate concentration of 2.7 millimoles per liter. This substrate solution was aliquoted and stored frozen at −20° C. The $FIX_a$+FX reagent contained the factor $IX_a$ and factor X and was dissolved in 10 milliliters of water. The solution was aliquoted and stored frozen at −70° C. until use. Also supplied with the kit were the following solutions: 0.025 molar calcium chloride; phospholipid (porcine brain); and Buffer Stock Solution (diluted one part of Stock Solution to nine parts of water for the assay, resulting in a final concentration of 0.06M Tris-HCl, pH 7.3, containing 0.02 percent bovine albumin). These solutions were stored at 4° C. until use.

The phospholipid +$FIX_a$+FX reagent is prepared by mixing one volume of phospholipid with five volumes of $FIX_a$+FX reagent.

The following procedure was employed:

| Reagent | Sample Tube | Reagent Blank |
|---|---|---|
| Phospholipid + $FIX_a$ + FX | 200 μl | 200 μl |
| Test sample | 100 | — |
| Buffer working solution | — | 100 |
| Mix well and incubate at 37° C. for 4 minutes Calcium chloride | 100 | 100 |
| Mix well and incubate at 37° C. exactly 10 minutes S-2222 + I-2581 | 200 | 200 |
| Mix well and incubate at 37° C. exactly 10 minutes Acetic acid (50 percent) Mix well | 100 | 100 |

The absorbance of the sample at 405 nm was determined against the reagent blank in a spectrophotometer within 30 minutes.

The absorbance at 405 was related to factor VIII units by calibrating the assay using a standard normal human plasma (George King Biomedical, Overland Park, Kans.).

EXAMPLE OF PREFERRED EMBODIMENT

1. General Strategy for Obtaining the Factor VIII Gene

The most common process of obtaining a recombinant DNA gene product is to screen libraries of cDNA clones obtained from mRNA of the appropriate tissue or cell type. Several factors contributed to use also of an alternative method of screening genomic DNA for the factor VIII gene. First, the site of synthesis of factor VIII was unknown. Although the liver is frequently considered the most likely source of synthesis, the evidence is ambiguous. Synthesis in liver and possibly spleen have been suggested by organ perfusion and transplantation studies (56). However, factor VIII activity is often increased in patients with severe liver failure (56a). Recent conflicting studies employing monoclonal antibody binding to cells detect highest levels of the protein in either liver sinusoidal endothelial (51), hepatocyte (52) or lymph node cells (followed in amount by lung, liver and spleen; (53)). In contrast, the factor VIII related antigen (von Willebrand Factor) is almost certainly synthesized by endothelial cells (54). Not only is the tissue source uncertain, the quantity of factor VIII in plasma is extremely low. The circulating concentration of about 100–200 ng/ml (55) is about 1/2,000,000 the molar concentration of serum albumin, for example. Thus, it was not clear that cDNA libraries made from RNA of a given tissue would yield factor VIII clones.

Based on these considerations, it was decided to first screen recombinant libraries of the human genome in bacteriophage lambda (henceforth referred to as genomic libraries). Although genomic libraries should contain the factor VIII gene, the likely presence of introns might present obstacles to the ultimate expression of the recombinant protein. The general strategy was to:

1. Identify a genomic clone corresponding to a sequenced portion of the human factor VIII protein.
2. Conduct a "genomic walk" to obtain overlapping genomic clones that would include the entire mRNA coding region.
3. Use fragments of the genomic clones to identify by hybridization to RNA blots tissue or cell sources of factor VIII mRNA and then proceed to obtain cDNA clones from such cells.
4. In parallel with no. 3, to express portions of genomic clones in SV40 recombinant "exon expression" plasmids. RNA transcribed from these plasmids after transfection of tissue culture (cos) cells should be spliced in vivo and would be an alternative source of cDNA clones suitable for recombinant factor VIII protein expression.

The actual progress of this endeavor involved simultaneous interplay of information derived from cDNA clones, genomic clones of several types, and SV40 recombinant "exon expression" clones, which, of necessity, are described separately below.

2. Genomic Library Screening Procedures

The factor VIII gene is known to reside on the human X chromosome (56). To increase the proportion of positive clones, genomic libraries were constructed from DNA obtained from an individual containing 4X chromosomes. (The lymphoblast cell line is karyotyped 49,XXXXY; libraries constructed from this DNA are referred to herein as "4X libraries"). 49,XXXXY DNA was partially digested with Sau3AI and appropriate size fractions were ligated into λ phage or cosmid vectors. Details of the construction of these λ/4X and cosmid/4X libraries are given below. The expected frequency of the factor VIII gene in the λ/4X library is about one in 110,000 clones and in the cosmid library about one in 40,000.

These libraries were screened for the factor VIII gene with synthetic oligonucleotide probes based on portions of the factor VIII protein sequence. These oligonucleotide probes fall into two types, a single sequence of 30 to 100 nucleotides based on codon choice usage analysis (long probes) and a pool of probes 14–20 nucleotides long specifying all possible degeneracy combinations for each codon choice (short probes).

The main advantage of long probes is that they can be synthesized based on any 10–30 amino acid sequence of the protein. No special regions of low codon redundancy need be found. Another advantage is that since an exact match with the gene sequence is not necessary (only stretches of complementarity of 10–14 nucleotides are required), interruption of complementarity due to presence of an intron, or caused by gene polymorphism or protein sequencing error, would not necessarily prevent usable hybridization. The disadvantage of long probes is that only one codon is selected for each amino acid. We have based our choice of codons on a table of mammalian codon frequency (57), and when this gave no clear preference, on the codon usage of the Factor IX gene (58). Since the expected sequence match of the long probes is unknown, the hybridization stringency must be determined empirically for each probe. This was performed by hybridization to genomic DNA blots and washes at various stringencies.

The advantage of short probes is that every codon possible is synthesized as a pool of oligonucleotides. Thus if the amino acid sequence is correct, a short probe should always hybridize to the gene of interest. The main limitation is the complexity of the pool of sequences that can be synthesized. Operationally a pool of 32 different sequences might be considered as a maximum pool size given the signal to noise limitations of hybridization to genomic libraries. This means that only protein sequences in regions of low codon redundancy can be used. A typical probe would be a pool of 16 17-mers specifying all possible sequences over a 6 amino acid fragment of protein sequence.

As with long probes, the hybridization stringency used for short probes had been determined empirically. This is because under ordinarily used hybridization conditions (6× SSC), the stability of the hybrids depends on the two factors—the length and the G-C content; stringent conditions for the low G-C content probes are not at all stringent for the high G-C content ones. A typical pool of 16 17-mers might have a range of 41 to 65 percent G-C and these probes will melt in 6× SSC over a 10° C. temperature range (from 48°–58° C.). Since the correct sequence within the pool of 16 is not known in advance, one uses a hybridization stringency just below 48° C. to allow hybridization of the lowest G-C content sequence. However, when screening a large number of clones, this will give many false positives of shorter length and higher G-C content. Since the change in melting temperature is 1° to 2° C. per base pair match, probe sequences as short as 12 or 13 of the 17 will also bind if they have a high G-C content. At random in the human genome a pooled probe of 16 17-mers will hybridize with 1200 times as many 13 base sequences as 17 base sequences.

A hybridization technique was developed for short probes which equalizes the stability of G-C and A-T base pairs and greatly enhances the utility of using short probes to screen libraries of high DNA sequence complexity.

Figure 1A:
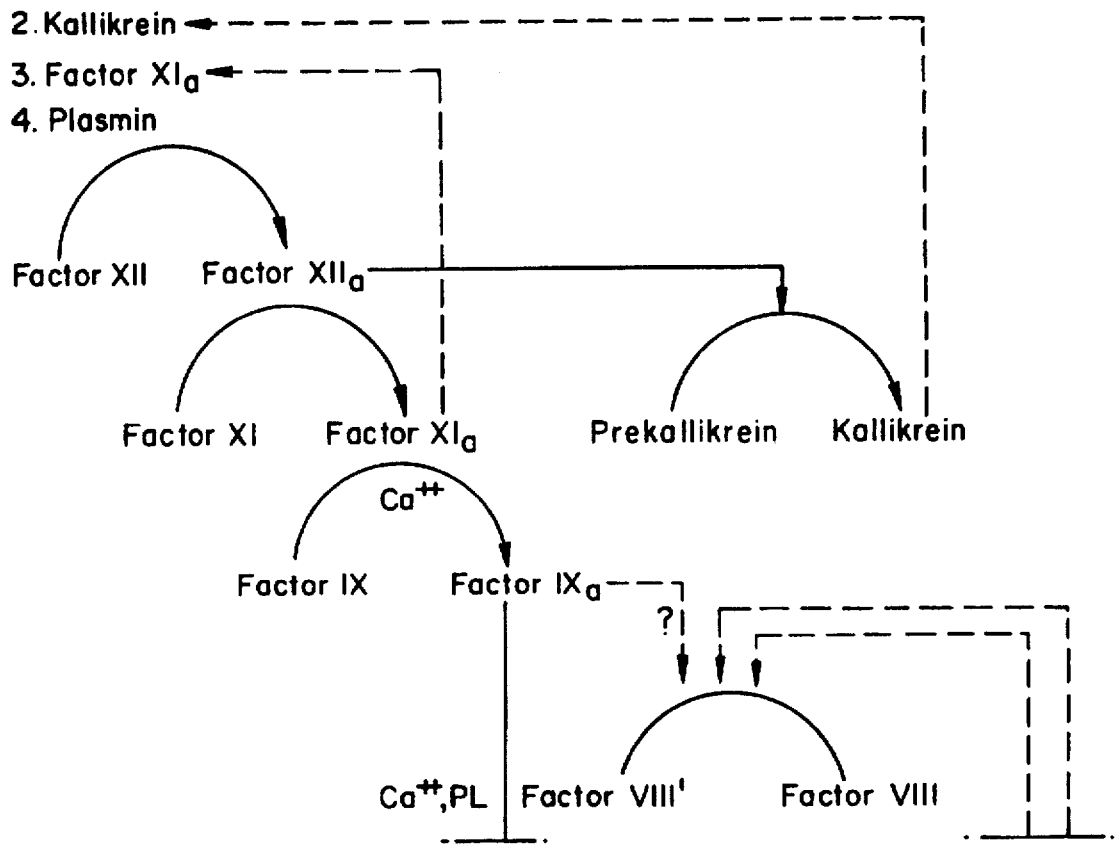
FIG. 1. Diagrammatic representation of the coagulation cascade (2).
Figure 1B:
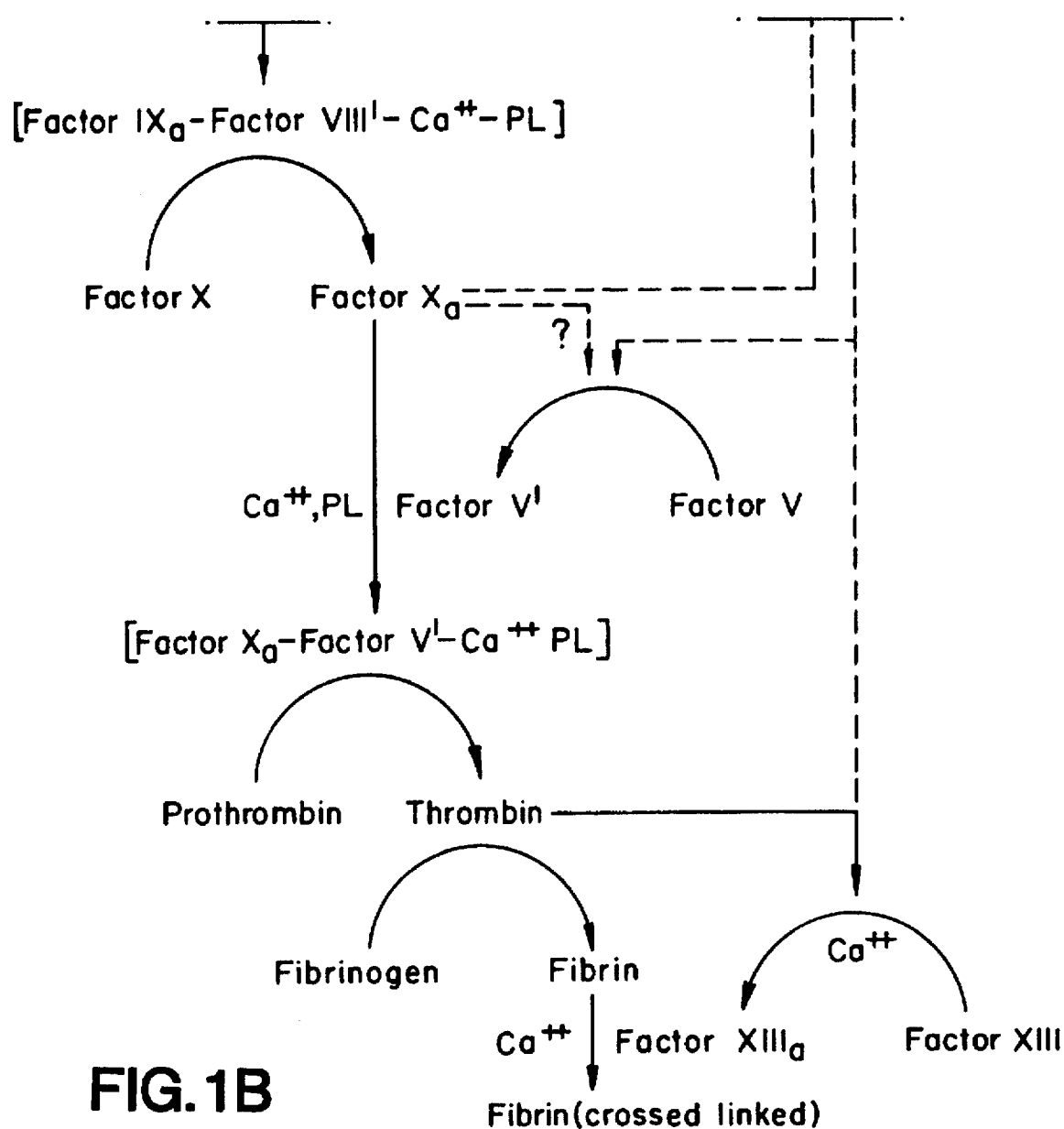
Figure 2A:
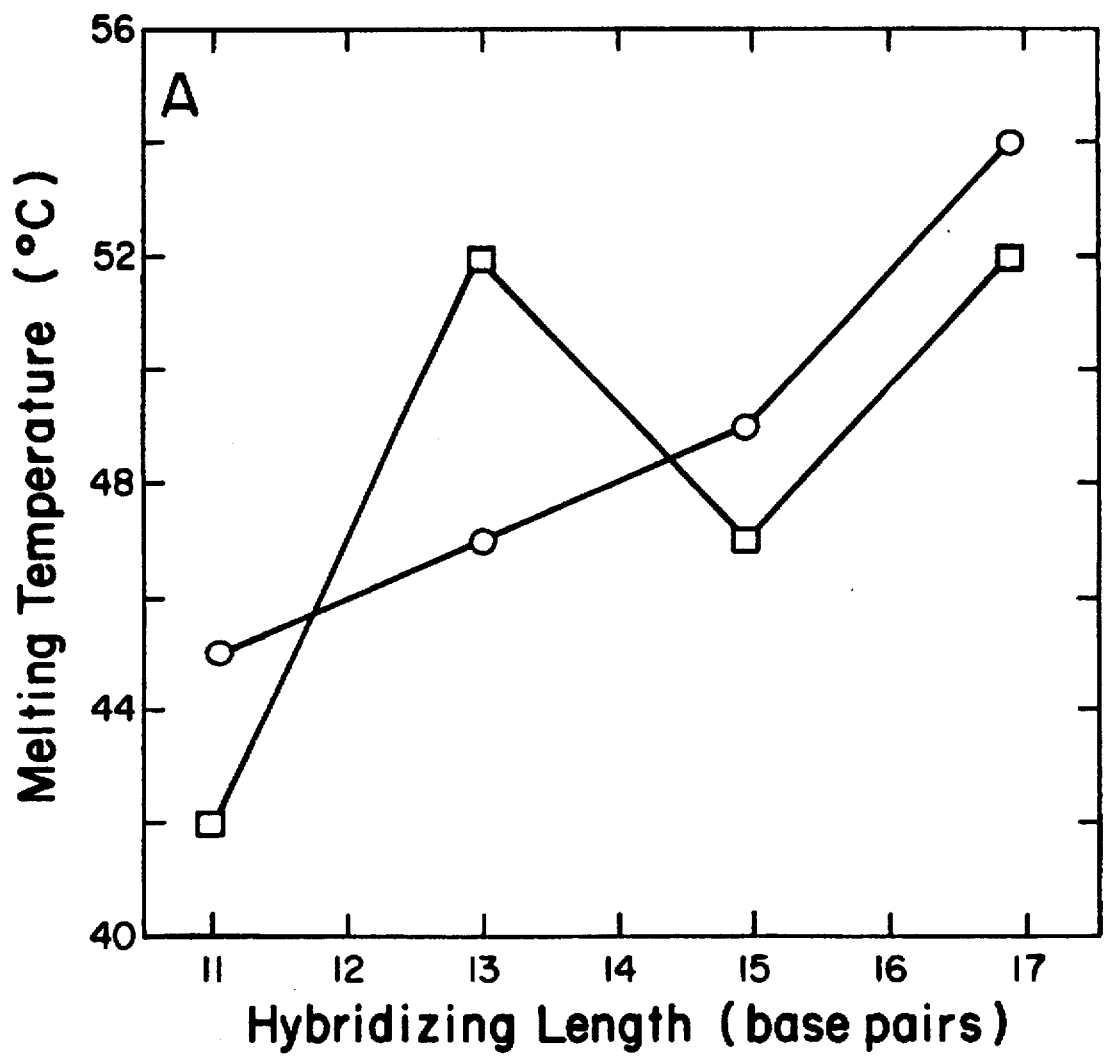
FIG. 2. Melting of DNA in TMACl and 6× SSC. A: For each point ten duplicate aliquots of λ DNA were first bound to nitrocellulose filters. These filters were then hybridized without formamide at 37° C. as described in Methods. Pairs of spots were then washed in 6× SSC, 0.1 percent SDS (□) or 3.0M TMACl, 50 mM Tris HCl, pH 8.0, 0.1 percent SDS, 2 mM EDTA (0) in 2° C. increments from 38° to 56° C. The melting temperature is the point where 50 percent of the hybridization intensity remained. B: A melting experiment as in panel A was performed by binding aliquots of pBR322 DNA to nitrocellulose filters. Probe fragments of various lengths were generated by digestion of pBR322 with MspI, end-labeling of the fragments with $^{32}$P, and isolation on polyacrylamide gels. The probe fragments from 18 to 75 b were hybridized without formamide at 37° C. and those from 46 to 1374 b in 40 percent formamide at 37° C. as described in Methods. The filters were washed in 3.0M tetramethylammonium chloride (TMACl), 50 mM Tris HCl, pH 8.0, 0.1 percent SDS, 2 mM EDTA in 3° C. increments to determine the melting temperature. (0) melting temperature determined for pBR322 MspI probe fragments, (△) melting temperatures in 3.0M TMACl from panel A for 11–17 b probes.
Figure 2B:
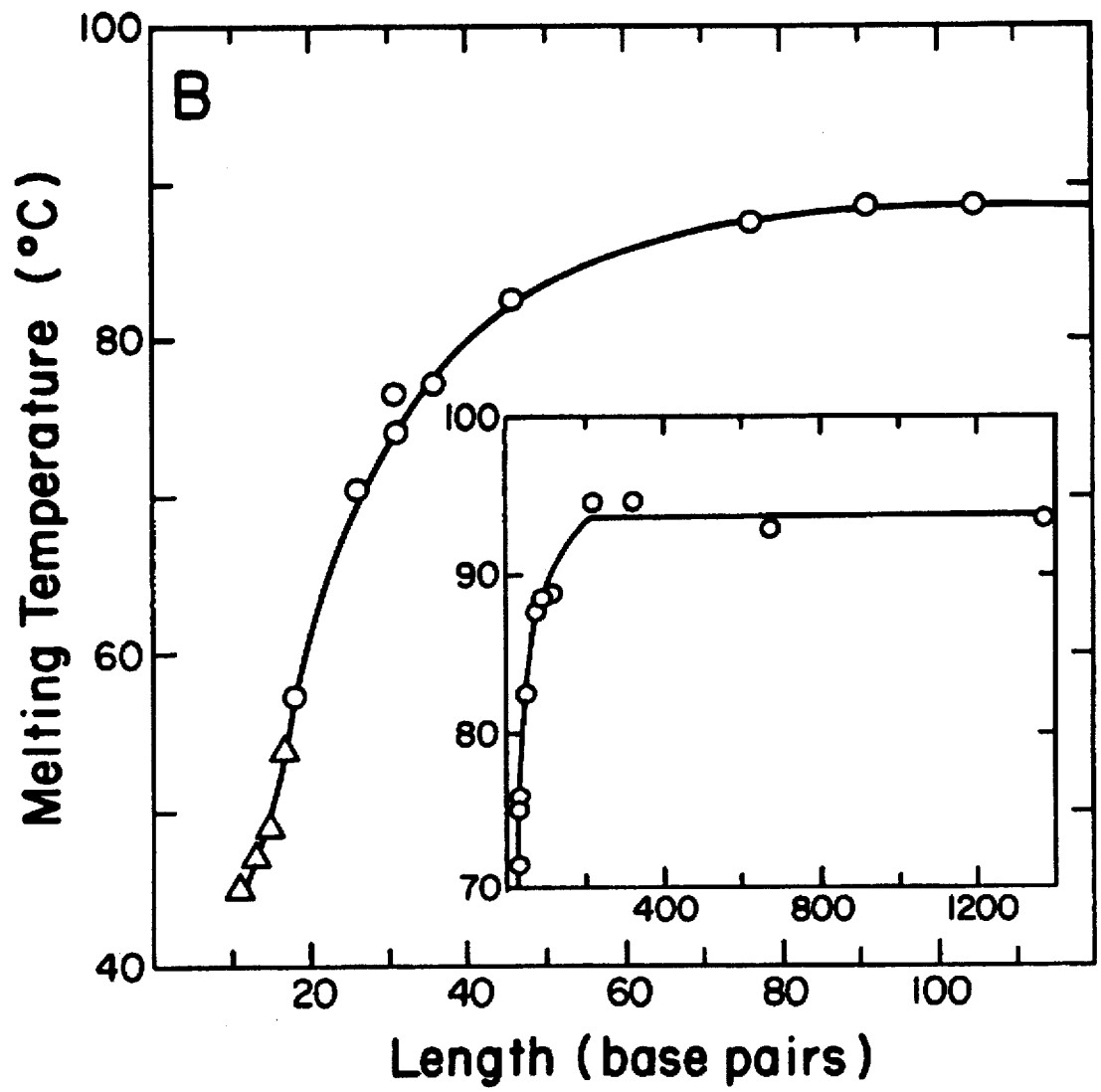

In FIG. 2A is plotted the melting temperature of 4 short probes under ordinary (6× SSC) and 3.0M TMACl wash conditions. In 3.0M TMACl the probes melt as a nearly linear function of length, while in 6× SSC, the melting is greatly influenced by the G-C content. The high melting temperature in 6× SSC of the 13-mer that is 65 percent G-C clearly demonstrates this conclusion. FIG. 2B shows the melting temperature in 3.0M TMACl as a function of length for 11 to thousands of bases. This figure allows the rapid selection of hybridization conditions for a probe with an exact match of any length desired.

The TMACl hybridization procedure has great utility whenever an exact sequence match of some known length is desired. Examples of this technique include: 1. Screening of a human genomic library with a pool of 16 17-mers. We have used a 3.0M TMACl wash at 50° C., which allows hybridization of only 17, 16, and a few 15 base sequences. The large number of high G-C content probes of lower homology are thus excluded. 2. If a short probe screen yields too many positives to sequence easily, the mostly likely candidates can be found by a TMACl melting procedure. Replicas of the positives are hybridized and washed at 2° C. intervals (for 17-mers (which melt at 54° C.) 46°, 48°, 50°, 52°, 54°, and 56° C. would be used). The positives that melt at the highest temperature will match the probe most closely. With a standard of known sequence the homology can be predicted ±1 base or better for a 17-mer. 3. Similarly, if a long probe screen yields too many positives, pooled short probes based on the same protein sequence can be synthesized. Since one member of this pool would contain a perfect match, TMACl melting experiments could refine the choice of best candidate positives. 4. In site directed mutagenesis, an oligonucleotide typically 20 long with 1 or more changes in the center is synthesized. The TMACl wash procedure can easily distinguish the parental and mutant derivatives even for a 1 base mismatch in the middle of a 20-mer. This is because the desired mutation matches the probe exactly. The wash conditions can simply be determined from FIG. 2B. 5. Selection of one particular gene out of a family of closely related genes. A melting experiment similar to that described above has been used to select one particular gene out of a collection of 100 very similar sequences.

3. First Isolation of the Factor VIII Genomic Clone

Factor VIII enriched preparations were prepared from human cryoprecipitate by polyelectrolyte chromatography and immunoadsorption as previously described (79). This material was dialyzed into 0.1 percent sodium dodecyl sulfate (SDS) and 1 percent ammonium bicarbonate, lyophilized, and stored at −20° C. until use.

Due to contamination of the factor VIII preparations by other plasma proteins, further fractionation was required in order to purify the factor VIII as well as separate the various polypeptide chains believed to arise from the factor VIII. This was accomplished by chromatography of the protein on Toya Soda TSK 4000 SW columns using high pressure liquid chromatography in the presence of SDS. Such chromatography separates the proteins by molecular size.

The lyophilized protein was reconstituted in distilled water and made 1 percent SDS and 0.1M sodium phosphate, pH 7.5. The TSK column (0.75×50 cm; Alltech, Deerfield, Ill.) was equilibrated at room temperature with 0.1 percent SDS in 0.1M sodium phosphate, pH 7.0. Samples of approximately 0.15 to 0.25 mL were injected and the column was developed isocratically at a flow rate of 0.5 mL per minute. The absorbance was monitored at 280 nm and fractions of 0.2 mL were collected. A representative elution profile is shown in FIG. 15. Aliquots were analyzed by sodium dodecyl sulfate gel electrophoresis on gradient gels of 5 percent to 10 percent polyacrylamide and analyzed by silver staining (80). The material which eluted after 25 minutes corresponded to a doublet of proteins at 80,000 and 78,000 D. The fractions containing these proteins were pooled as indicated by bar in FIG. 15, from three separate preparative TSK runs, and stored at −20 degrees until use.

The purified 80,000 dalton protein from the TSK fractionation (0.8 nmoles) was dialyzed overnight against 8M urea, 0.36M Tris-HCl, pH 8.6, and 3.3 mM ethylenediamine-tetraacetic acid under a nitrogen atmosphere. Disulfide bonds were reduced by the inclusion of 10 mM dithiothreitol in the above dialysis buffer. The final volume was 1.5 ml. The cysteines were alkylated with 15 microliters of 5M iodoacetic acid (dissolved in 1M NaOH). The reaction was allowed to proceed for 35 minutes at room temperature in the dark, and the alkylation reaction was quenched by the addition of dithiothreitol to a final concentration of 100 mM. The protein solution was dialyzed against 8M urea in 0.1M ammonium bicarbonate for four hours. The dialysis solution was changed to gradually dilute the urea concentration (8M, 4M, 2M, 1M, and finally 0.5M urea) over a period of 24 hours. Tryptic digestion was performed on the reduced, alkylated 80,000 dalton protein by the addition of TPCK-treated trypsin (Sigma Chem. Co.) at a weight ratio of 1 part trypsin to 30 parts factor VIII protein. The digestion was allowed to continue for 12 hours at 37° C. The reaction mixture was frozen until use. HPLC separation of the tryptic peptides was performed on a high resolution Synchropak RP-P C-18 column (0.46×25 cm, 10 microns) at room temperature with a Spectra-Physics 8000 chromatograph. Samples of approximately 0.8 mL were injected and the column was developed with a gradient of acetonitrile (1 percent to 70 percent in 200 minutes) in 0.1 percent trifluoroacetic acid. The absorbance was monitored at 210 nm and 280 nm (FIG. 16). Each peak was collected and stored at 4° C. until subjected to sequence analysis in a Beckman spinning cup sequencer with on-line PTH amino acid identification. The arrow in FIG. 16, eluting at approximately 23 percent acetonitrile, indicates the peak containing the peptide with the sequence AWAYFSDVDLEK. This sequence was used to generate the oligonucleotide probe 8.3 for human genomic library screening.

Long and short probes were synthesized based on the considerations just discussed. The second long probe used was based on the sequence of a 12 amino acid factor VIII tryptic fragment, AWAYFSDVDLEK. The DNA sequence chosen to synthesize for this probe was 5'-CTTTTCCAGGTCAACGTCGGAGAAATAAGCCC-AAGC. This probe (called 8.3) was first tested in genomic blot hybridizations. FIG. 3A shows genomic Southern blots of normal male (1X) and 49,XXXXY (4X) DNA hybridized with labeled 8.3 probe and washed at various stringencies. Even at the highest stringency (1× SSC, 46° C.) a single band of 3.8 kb (EcoRI) and 9.4 kb (BamHI) was observed. The intensity of this band had a ratio of about 1:4 in the 1X and 4X lanes as would be expected for the X-linked factor VIII gene. Control experiments had demonstrated that a known X-linked gene probe (Factor IX) gave the expected 1:4 hybridization ratio, while an autosomal gene (albumin) gave a 1:1 ratio.

Based on these genomic blot results, the 8.3 probe was used to screen the λ/4X library. 500,000 phage were grown on fifty 150 mm plates and duplicate nitrocellulose filters were hybridized with $^{32}$P-labeled 8.3 probe at a wash stringency of 1× SSC, 37° C. (FIG. 3). Upon retesting, 15 strongly hybridizing and 15 more weakly hybridizing clones were obtained. DNA was prepared from these isolated plaques, cleaved with restriction endonucleases, and blot hybridized with probe 8.3. Many of the strongly hybridizing clones yielded a hybridizing EcoRI fragment of 3.8 kb, the same size detected in the genomic blot. In addition, all strongly hybridizing clones displayed an identical 262 base pair Sau3AI fragment upon hybridization with the 8.3 probe. Sau3AI fragments were cloned into the single-stranded phage vector M13mp8 (86), screened by hybridization, and sequenced by the dideoxy procedure. The DNA sequence of the 262 bp fragment showed considerable homology with the 8.3 probe. The homology included regions of continuous matches of 14 and 10 bp with an overall homology of 83 percent. The first ten residues of the peptide fragment agreed with that deduced from the DNA sequence of the recombinant clones and they were preceded by a lysine codon as expected for the product of a tryptic digest. The final two predicted residues did not match the DNA sequence. However, the DNA at this juncture contained a good consensus RNA splice donor sequence (60, 61) followed shortly by stop codons in all three possible reading frames. This suggested the presence of an intron beginning at this position. (This suggestion was confirmed with cDNA clones described below.) An open reading frame extended almost 400 b 5' of the region of homology. In this region several consensus splice acceptor sequences were identified. Inspection of the DNA-predicted protein sequence for this region revealed matches with protein sequence of several additional tryptic peptide fragments of factor VIII. This demonstrated that an exon of a genomic clone for human factor VIII had been obtained.

4. Extension of Genomic Clones: λLibrary Genome Walking

Initially 8 independent factor VIII genomic clones were obtained from the λ/4X library. These contained overlapping segments of the human genome spanning about 28 kb. From the estimated size of the factor VIII protein, it was assumed that the complete gene would encompass 100–200 kb, depending on the length of introns. Hence the collection of overlapping clones was expanded by "genome walking".

Figure 4:
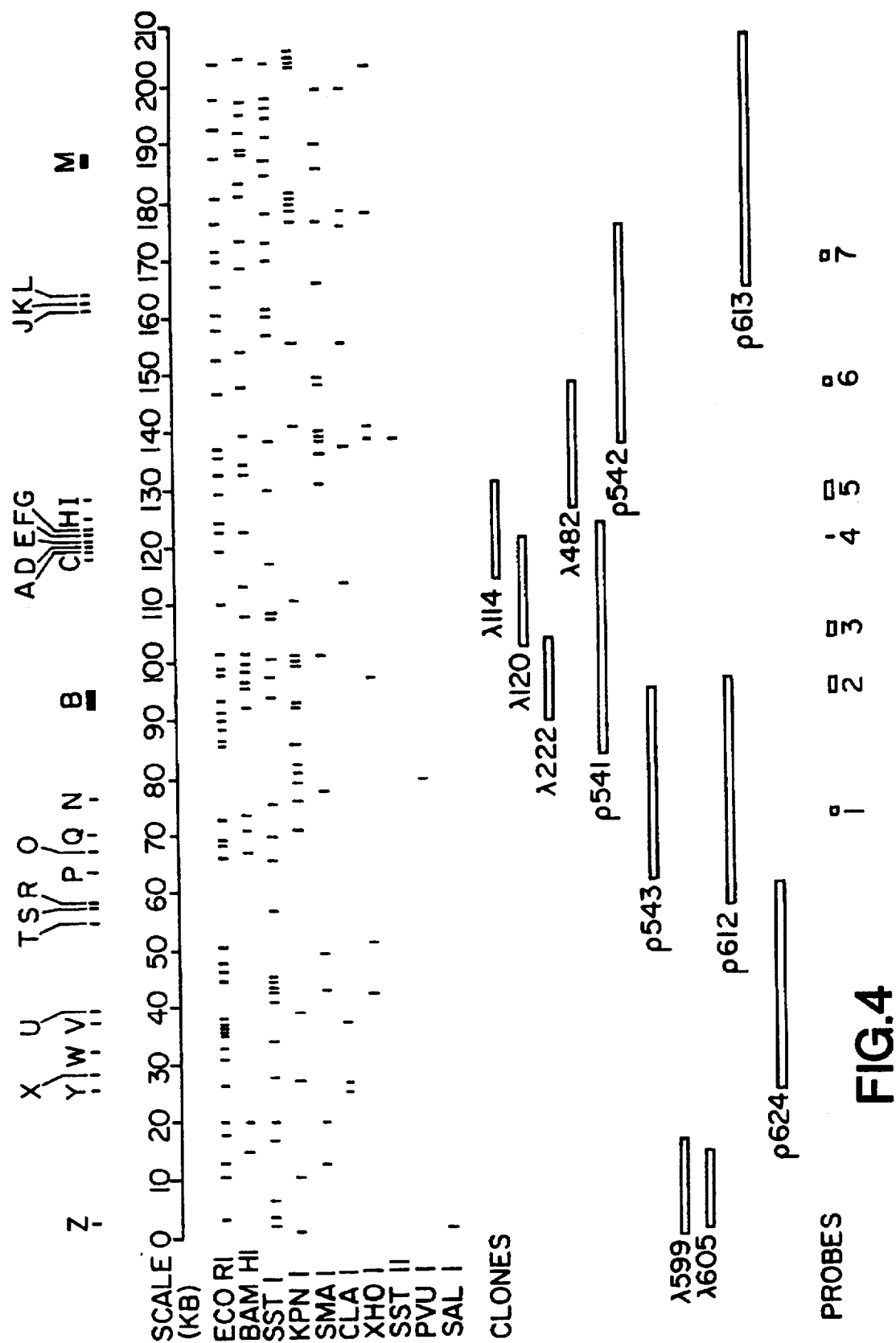
FIG. 4. Map of the Human Factor VIII Gene. The top line shows the positions and relative lengths of the 26 protein coding regions (Exons A to Z) in the Factor VIII gene. The direction of transcription is from left to right. The second line shows the scale of the map in kilobase pairs (kb). The location of the recognition sites for the 10 restriction enzymes that were used to map the Factor VIII gene are given in the next series of lines. The open boxes represent the extent of human genomic DNA contained in each of the λ phage (λ114, λ120, λ222, λ482, λ599 and λ605) and cosmid (p541, p542, p543, p612, 613, p624) clones. The bottom line shows the locations of probes used in the genomic screens and referred to in the text: 1) 0.9 kb EcoRI/BamHI fragment from p543; 2) 2.4 kb EcoRI/BamHI fragment from λ222; 3) 1.0 kb NdeI/BamHI triplet of fragments from λ120; 4) oligonucleotide probe 8.3; 5) 2.5 kb StuI/EcoRI fragment from λ114; 6) 1.1 kb EcoRI/BamHI fragment from λ482; 7) 1.1 kb BamHI/EcoRI fragment from p542. Southern blot analysis of 46,XY and 49,XXXXY genomic DNA revealed no discernible differences in the organization of the Factor VIII gene.

The first step in this process was the mapping of restriction endonuclease cleavage sites in the existing genomic clones (FIG. 4). DNA from the clones was digested with restriction enzymes singly or in combinations, and characterized by gel electrophoresis (followed by Southern blot hybridization in some cases). DNA fragments generated by EcoRI and BamHI digestion were subcloned into pUC plasmid vectors (59) for convenience. Restriction mapping, DNA sequence analysis, and blot hybridizations with the 8.3 probe determined the gene orientation.

Next, single copy fragments near the ends of the 28 kb region were identified as "walk" probes. Digests of cloned DNA were blot hybridized with total $^{32}$P-labeled human DNA. With this technique only fragments containing sequences repeated more than about 50 times in the genome will hybridize (87, 88). Non-hybridizing candidate walk probe fragments were retested for repeated sequences by hybridization to 50,000 phage from the λ/4X library.

In the 5' direction, a triplet of 1 kb probe fragments was isolated from λ120 DNA digested with NdeI and BamHI (see FIG. 4). One million λ/4X bacteriophage were screened with this probe. A resulting clone, λ222, was shown to extend about 13 kb 5' of λ120 (see FIG. 4).

In the 3' direction, a 2.5 kb StuI/EcoRI restriction fragment of λ114 was identified as a single copy walk probe. Exhaustive screening of the λ/4X, and subsequently other λ/human genomic libraries, failed to yield extending clones. Under-representation of genomic regions in λ libraries has been observed before (62). It was decided to specifically enrich genomic DNA for the desired sequences and construct from it a limited bacteriophage library.

Southern blot hybridization of human genomic DNA with the 2.5 kb StuI/EcoRI probe showed a 22 kb hybridizing BclI restriction fragment. Restriction mapping showed that cloning and recovery of this fragment would result in a large 3' extension of genomic clones. Human 49,XXXXY DNA was digested with BclI, and a size fraction of about 22 kb was purified by gel electrophoresis. This DNA was ligated into the BamHI site of the bacteriophage vector λ1059 and a library was prepared. (The previously used vector, Charon 30, could not accommodate such a large insert.) Six hybridizing clones were obtained from 400,000 phage screened from this enriched library. The desired clone, designated λ482, extended 17 kb further 3' than our original set of overlapping genomic clones (FIG. 4).

5. Genome Walking: Cosmid Clones

A new genomic library was constructed with cosmid vectors. Cosmids (63), a plasmid and bacteriophage hybrid, can accommodate approximately 45 kb of insert, about a three-fold increase over the average insert size of the λ/4X DNA library. A newly constructed cosmid vector, pGcos4, has the following desirable attributes:

1. A derivative of the tetracycline resistance gene of pBR322 was used that did not contain a BamHI site. This allowed a BamHI site to be put elsewhere in the plasmid and to be used as the cloning site. Tetracycline resistance is somewhat easier to work with than the more commonly used ampicillin resistance due to the greater stability of the drug.
2. The 403 b HincII fragment of λ containing the cos site was substituted for the 641 b AvaI/PvuII fragment of pBR322 so that the copy number of the plasmid would be increased and to remove pBR322 sequences which interfere with the transformation of eukaryotic cells (75). 3. A mutant dihydrofolate reductase gene with an SV40 origin of replication and promoter was included in the pGcos4 vector. In this way any fragments cloned in this vector could then be propagated in a wide range of eucaryotic cells. It was expected this might prove useful in expressing large fragments of genomic DNA with their natural promoters. 4. For the cloning site, a synthetic 20-mer with the restriction sites EcoRI, PvuI, BamHI, PvuI, and EcoRI was cloned into the EcoRI site from pBR322. The unique BamHI site is used to clone 35–45 b Sau3A1 fragments of genomic DNA. The flanking EcoRI sites can be used for subcloning the EcoRI fragments of the insert. The PvuI sites can be used to cut out the entire insert in most cases. PvuI sites are exceedingly rare in eucaryotic DNA and are expected to occur only once every 134,000 b based on dinucleotide frequencies of human DNA.

Figure 5:
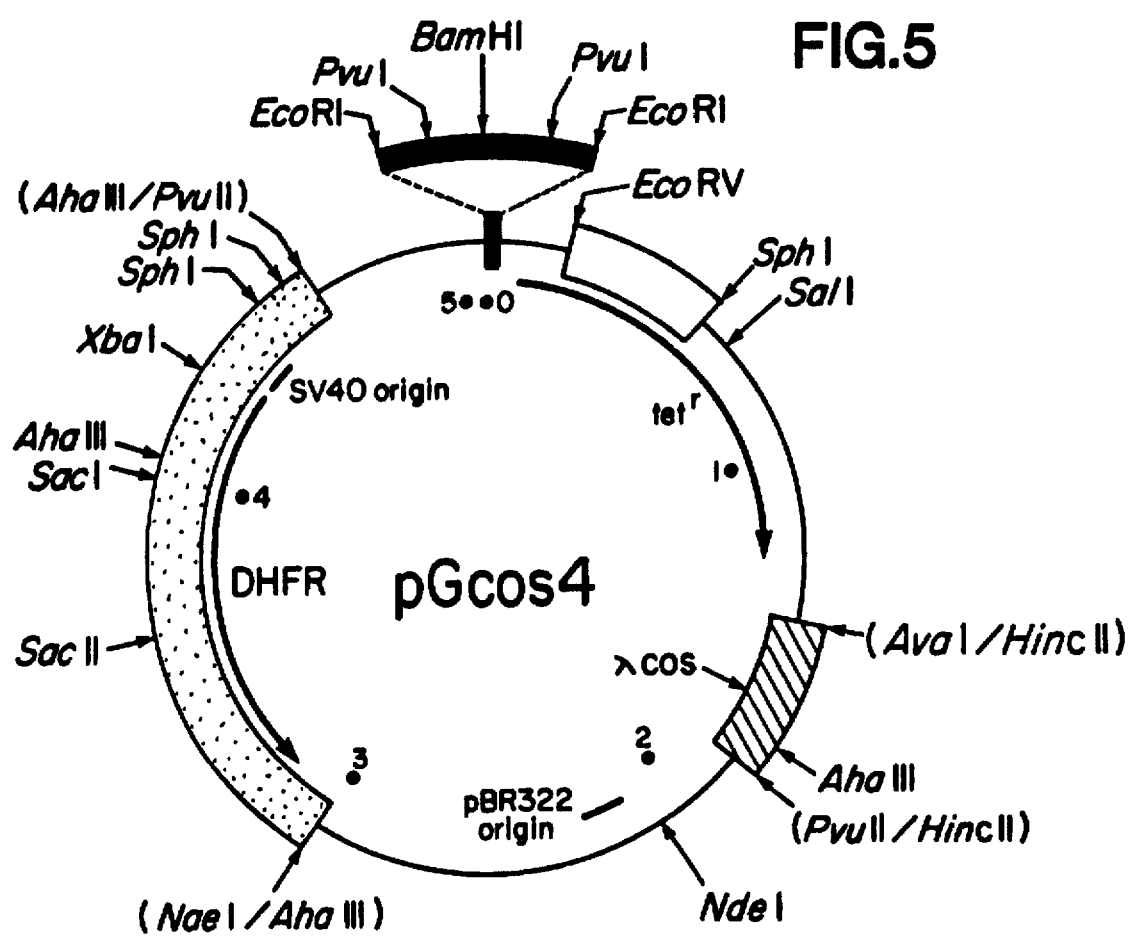
FIG. 5. Cosmid vector pGcos4. The 403 b annealed HincII fragment of λc1857S7 (Bethesda Research Lab.) containing the cos site was cloned in pBR322 from AvaI to PvuII to generate the plasmid pGcos1. Separately, the 1624 b PvuII to NaeI fragment of pFR400 (49n), containing an SV40 origin and promoter, a mutant dihydrofolate reductase gene, and hepatitis B surface antigen termination sequences, was cloned into the pBR322 AhaIII site to generate the plasmid mp33dhfr. A three-part ligation and cloning was then performed with the 1497 b SphI to NdeI fragment of pGcos1, the 3163 b NdeI to EcoRV fragment of mp33dhfr, and the 376 b EcoRV to SphI fragment of pKT19 to generate the cosmid vector pGcos3. pKT19 is a derivative of pBR322 in which the BamHI site in the tetracycline resistance gene has the mutated nitroguanosine treatment. pGcos4 was generated by cloning the synthetic 20mer, 5' AATTCGATCGGATCCGATCG, in the EcoRI site of pGcos3.

FIG. 5 gives the scheme for constructing the cosmid vector, pGcos4. 35–45 kb Sau3A1 fragments of 49, XXXXY DNA were cloned in this vector. About 150,000 recombinants were screened in duplicate with a 5' 2.4 kb EcoRI/BamHI fragment of 222 and a 3' 1 kb EcoRI/BamHI fragment of λ482 which were single copy probes identified near the ends of the existing genomic region. Four positive cosmid clones were isolated and mapped. FIG. 4 includes cosmids p541, p542 and p543. From this screen, these cosmid clones extended the factor VIII genomic region to a total of 114 kbp. Subsequent probing with cDNA clones identified numerous exons in the existing set of overlapping genomic clone, but indicated that the genomic walk was not yet complete. Additional steps were taken in either direction.

A 3' walk probe was prepared from a 1.1 kb BamHI/EcoRI fragment of p542 (FIG. 4). This probe detected the overlapping cosmid clone p613 extending about 35 kb farther 3'. At a later time, the full Factor VIII message sequence was obtained by cDNA cloning (see below). When a 1.9 kb EcoRI cDNA fragment containing the 3'-terminal portion of the cDNA was hybridized to Southern blots of human genomic and cosmid cloned DNA, it identified a single 4.9 kb EcoRI band and 5.7, 3.2 and 0.2 kb BamHI bands in both noncloned (genomic) and p613 DNA. This implied that the 3' end of the gene had now been reached, as we later confirmed by DNA sequence analysis.

A 5' walk probe was prepared from a 0.9 kb EcoRI/pamHI fragment of p543. It detected an overlapping cosmid clone p612, which slightly extended the overlapping region. The 5'-most genomic clones were finally obtained by screening cosmid/4X and λ/4X libraries with cDNA derived probes. As shown in FIG. 4, λ1599, λ605 and p624 complete the set of recombinant clones spanning Factor VIII gene. (These clones overlap and contain all of the DNA of this region of the human genome with the exception of an 8.4 kb gap between p624 and λ599 consisting solely of intron DNA.) Together, the gene spans 200 kb of the human X chromosome. This is by far the largest gene yet reported. Roughly 95 percent of the gene is comprised of introns which must be properly processed to produce template mRNA for the synthesis of Factor VIII protein.

The isolation of the factor VIII gene region in λ and cosmid recombinant clones is not sufficient to produce a useful product, the factor VIII protein. Several approaches were followed to identify and characterize the protein coding (exon) portions of the gene in order to ultimately construct a recombinant expression plasmid capable of directing the synthesis of active factor VIII protein in transfected microorganisms or tissue culture cells. Two strategies failed to yield substantially useful results: further screening of genomic clones with new oligonucleotide probes based on protein sequencing, and the use of selected fragments of genomic clones as probes to RNA blot hybridizations. However, coding regions for the factor VIII protein were isolated with the use of SV40 "exon expression" vectors, and, ultimately, by cDNA cloning.

6. SV40 exon expression vectors

It is highly unlikely that a genomic region of several hundred kb could be completely characterized by DNA sequence analysis or directly used to synthesize useful amounts of factor VIII protein. Roughly 95 percent of the human factor VIII gene comprises introns (intervening sequences) which must be removed artificially or by eukaryotic RNA splicing machinery before the protein could be expressed. A procedure was created to remove introns from incompletely characterized restriction fragments of genomic clones using what we call SV40 expression vectors. The general concept entails inserting fragments of genomic DNA into plasmids containing an SV40 promoter and producing significant amounts of recombinant RNA which would be processed in the transfected monkey cos cells. The resulting spliced RNA can be analyzed directly or provide material for cDNA cloning. In theory at least, this technique could be used to assemble an entire spliced version of the factor VIII gene.

Our first exon expression constructions used existing SV40 cDNA vectors that expressed the hepatitis surface antigen gene (73). However, the genomic factor VIII fragments cloned into these vectors gave no observable factor VIII RNA when analyzed by blot hybridization. It was surmised that the difficulty might be that in the course of these constructions the exon regions of the cDNA vectors had been joined to intron regions of the factor VIII gene. To circumvent these difficulties, the exon expression vector pESVDA (ATCC Accession No. 99,776, deposited with American Type Culture Collection (ATCC, 12301 Parklawn Drive, Rockville, Md. 20852, U.S.A. under the Budapest Treaty on Oct. 28, 1996) was constructed as shown in FIG. 6. This vector contains the SV40 early promoter, the Adenovirus II major late first splice donor site, intron sequences into which the genomic factor VIII fragments could be cloned, followed by the Adenovirus II E1b splice acceptor site and the hepatitis B surface antigen 3' untranslated and polyadenylation sequences (49j).

Figure 7A:
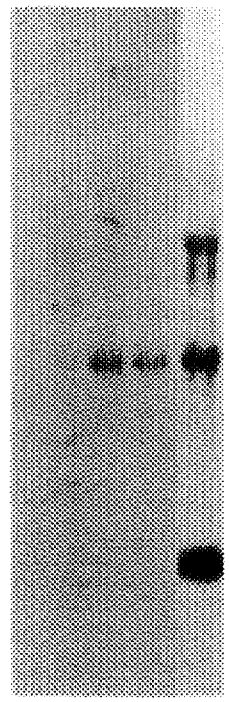
FIG. 7. Analysis of RNA transcripts from pESVDA vectors. Confluent 10 cm dishes of COS-7 cells (77) were transfected with 2 μg plasmid DNA using the modified DEAE-dextran method (84) as described (73). RNA was prepared 4 days post-transfection from cytoplasmic extracts (49n) and electrophoresed in denaturing formaldehyde-agarose gels. After transfer to nitrocellulose, filters were hybridized with the appropriate $^{32}$P-labelled DNA as described in Methods. Filters were washed in 2× SSC, 0.2 percent SDS at 42° and exposed to Kodak XR5 film. The position of the 28S and 18S ribosomal RNAs are indicated by arrow in each panel.
Figure 7B:
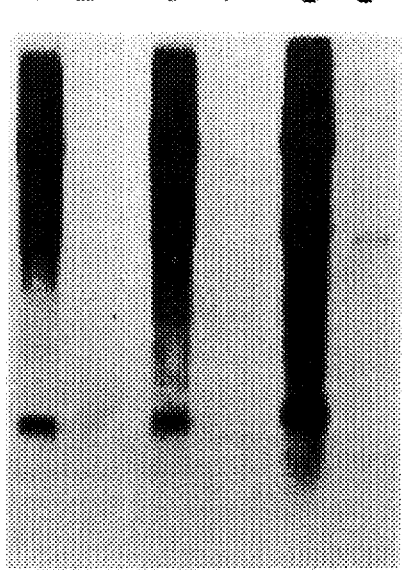
Figure 7C:
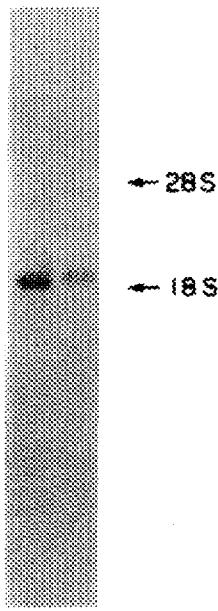

Initially the 9.4 kb BamHI fragment and the 12.7 kb SstI fragment of λ114 were cloned in the intron region of pESVDA (see FIG. 6). Northern blot analysis of the RNA synthesized by these two constructions after transfection of cos cells is shown in FIG. 7. With the 9.4 kb BamHI construction, a hybridizing RNA band of about 1.8 kb is found with probes for exon A, and hepatitis 3' untranslated sequence. To examine the RNA for any new factor VIII exons, a 2.0 kbp StuI/BamHI fragment of λ114, 3' of exon A, was hybridized in a parallel lane. This probe also showed an RNA band of 1.8 kb demonstrating the presence of additional new factor VIII exons in this region. Each of these three probes also hybridized to an RNA band from a construction containing the 12.7 kb SstI genomic fragment. This RNA band was about 2.1 kb. This observation suggested that an additional 200–300 bp of exon sequences were contained in this construction 3' of the BamHI site bordering the 9.4 kb BamHI fragment.

Control experiments showed that this system is capable of correctly splicing known exon regions. A 3.2 kb genomic HindIII fragment of murine dhfr spanning exons III and IV was cloned in pESVDA. An RNA band of 1 kb was found with a murine dhfr probe. This is the size expected if the exons are spliced correctly. Constructions with the 9.4 kb BamHI factor VIII or 3.2 kb dhfr genomic fragments in the opposite orientation, gave no observable RNA bands with any of the probes (FIG. 7).

A cDNA copy of the RNA from the 12.7 kb SstI construction was cloned in pBR322 and screened. One nearly full length (1700 bp) cDNA clone (S36) was found. The sequence of the 950 bp SstI fragment containing all of the factor VIII insert and a portion of the pESVDA vector on either side is presented in FIG. 8. The sequence begins and ends with the Adenovirus splice donor and acceptor sequences as expected. In between there are 888 bp of factor VIII sequence including exon A. The 154 bp preceding and the 568 bp following exon A contain several factor VIII 80K tryptic fragments, confirming that these are newly identified exons. Sequences of the genomic region corresponding to these exons showed that the 154 bp 5' of exon A are contained in one exon, C, and that the region 3' of exon A is composed of 3 exons, D, E, and I of 229, 183 and 156 bp, respectively. Each of these exons is bounded by a reasonable splice donor and acceptor site (60, 61).

Subsequent comparison of the S36 exon expression cDNA with the factor VIII cell line cDNA clones showed that all the spliced factor VIII sequence in S36 is from factor VIII exons. This included as expected exons C, A, D, E, and I. However, 47 bp of exon A were missing at the C, A junction and exons F, G, and H had been skipped entirely. The reading frame shifts resulting from such aberrant RNA processing showed that it could not correspond exactly to the factor VIII sequence. At the C, A junction a good consensus splice site was utilized rather than the authentic one. The different splicing of the S36 clone compared with the authentic factor VIII transcript may be because only a portion of the RNA primary transcript was expressed in the cos cell construction. Alternatively, cell type or species variability may account for this difference.

7. cDNA Cloning a. Identification of a cell line producing Factor VIII mRNA

To identify a source of RNA for the isolation of factor VIII cDNA clones, polyadenylated RNA was isolated from numerous human cell lines and tissues and screened by Northern blot hybridization with the 189 bp StuI-HincII fragment from the exon A region of λ120. Poly(A)+ RNA from the CH-2 human T-cell hybridoma exhibited a hybridizing RNA species. The size of the hybridizing RNA was estimated to be about 10 kb. This is the size mRNA expected to code for a protein of about 300 kD. By comparison with control DNA dot-blot hybridizations (66), the amount of this RNA was determined to be 0.0001–0.001 percent of the total cellular poly(A)+ RNA in the CH-2 cell line. This result indicated that isolation of factor VIII cDNA sequences from this source would require further enrichment of specific sequences or otherwise entail the screening of extremely large numbers of cDNA clones.

b. Specifically Primed cDNA Clones

The DNA sequence analysis of Factor VIII genomic clones allowed the synthesis of 16 base synthetic oligonucleotides to specifically prime first strand synthesis of cDNA. Normally, oligo(dT) is used to prime cDNA synthesis at the poly(A) tails of mRNA. Specific priming has two advantages over oligo(dT). First, it serves to enrich the cDNA clone population for factor VIII. Second, it positions the cDNA clones in regions of the gene for which we possessed hybridization probes. This is especially important in cloning such a large gene. As cDNA clones are rarely longer than 1000–2000 base pairs, oligo(dT) primed clones would usually be undetectable with a probe prepared from most regions of the factor VIII gene. The strategy employed was to use DNA fragments and sequence information from the initial exon A region to obtain specifically primed cDNA clones. We proceeded by obtaining a set of overlapping cDNA clones in the 5' direction based upon the characterization of the earlier generation of cDNA clones. In order to derive the more 3' region of cDNA, we employed cDNA and genomic clone fragments from 3' exons to detect oligo(dT) primed cDNA clones. Several types of cDNA cloning procedures were used in the course of this endeavor and will be described below.

The initial specific cDNA primer, 5'-CAGGTCAACATCAGAG ("primer 1"; see FIG. 9) was synthesized as the reverse complement of the 16 3'-terminal residues of the exon A sequence. C-tailed cDNA was synthesized from 5 µg of CH-2 cell poly(A)+ RNA with primer 1, and annealed into G-tailed pBR322 as described generally in (67). Approximately 100,000 resulting $E.$ $coli$ transformants were plated on 100 150 mm dishes and screened by hybridization (48) with the 189 bp StuI/HincII fragment from the exon A region of the genomic clone λ120 (FIG. 4). One bona fide hybridizing clone ("p1.11") was recovered (see FIG. 9). DNA sequence analysis of p1.11 demonstrated identity with our factor VIII genomic clones. The 447 bp cDNA insert in p1.11 contained the first 104 b of genomic exon A (second strand synthesis apparently did not extend back to the primer) and continued further into what we would later show to be exons B and C. The 5' point of divergence with exon A sequence was bordered by a typical RNA splice acceptor site (61).

Although the feasibility of obtaining factor VIII cDNA clones from the CH-2 cell line had now been demonstrated, further refinements were made. Efforts of several types were made to further enrich CH-2 RNA for factor VIII message. A successful strategy was to combine specifically primed first strand cDNA synthesis with hybrid selection of the resulting single stranded cDNA. Primer 1 was used with 200 µg of poly(A)+ CH-2 RNA to synthesize single stranded cDNA. Instead of using DNA polymerase to immediately convert this to double stranded DNA, the single stranded DNA was hybridized to 2 µg of 189 bp StuI/HincII genomic fragment DNA which had been immobilized on activated ABM cellulose paper (Schleicher and Schuell "Transa-Bind"; see (48). Although RNA is usually subject to hybrid selection, the procedure was applied after cDNA synthesis in order to avoid additional manipulation of the rare, large and relatively labile factor VIII RNA molecules. After elution, the material was converted to double stranded cDNA, size selected, and 0.5 ng of recovered DNA was C-tailed and cloned into pBR322 as before. Approximately 12,000 recombinant clones were obtained and screened by hybridization with a 364 bp Su3A/StuI fragment derived from the previous cDNA clone p1.11. The probe fragment was chosen deliberately not to overlap with the DNA used for hybrid selection. Thus avoided was the identification of spurious recombinants containing some of the StuI/HincII DNA fragment which is invariably released from the DBM cellulose. 29 hybridizing colonies were obtained. This represents a roughly 250-fold enrichment of desired clones over the previous procedure.

Each of the 29 new recombinants was characterized by restriction mapping and the two longest (p3.12 and p3.48; FIG. 9) were sequenced. These cDNA clones extended about 1500 bp farther 5' than p1.11. Concurrent mapping and sequence analysis of cDNA and genomic clones revealed the presence of an unusually large exon (exon B, FIG. 4) which encompassed p3.12 and p3.48. Based on this observation, DNA sequence analysis of the genomic clone λ222 was extended to define the extent of this exon. Exon B region contained an open reading frame of about 3 kb. 16 mer primers 2 and 3 were synthesized to match sequence within this large exon in the hope of obtaining a considerable extension in cDNA cloning.

At this point, it was demonstrated that a bacteriophage based cDNA cloning system could be employed, enabling production and screening of vast numbers of cDNA clones without prior enrichment by hybrid selection. λGT10 (68) is a phage λ derivative with a single EcoRI restriction site in its repressor gene. If double stranded cDNA fragments are flanked by EcoRI sites they can be ligated into this unique site. Insertion of foreign DNA into this site renders the phage repressor minus, forming a clear plaque. λGT10 without insert forms turbid plaques which are thus distinguishable from recombinants. In addition to the great transformation efficiency inherent in phage packaging, λ cDNA plaques are more convenient to screen at high density than are bacterial colonies.

Double stranded cDNA was prepared as before using primer 3, 5'-AACTCTGTTGCTGCAG (located about 550 bp downstream from the postulated 5' end of exon B). EcoRI "adaptors" were ligated to the blunt ended cDNA. The adaptors consisted of a complementary synthetic 18 mer and 22 mer of sequence 5'-CCTTGACCGTAAGACATG and 5'-AATTCATGTCTTACGGTCAAGG. The 5' end of the 18mer was phosphorylated, while the 5' end of the 22mer retained the 5'-OH with which it was synthesized. Thus, when annealed and ligated with the cDNA, the adaptors form overhanging EcoRI sites which cannot self-ligate. This allows one to avoid EcoRI methylation of cDNA and subsequent EcoRI digestion which follows linker ligation in other published procedures (83). After gel isolation to size select the cDNA and remove unreacted adapters, an equimolar amount of this cDNA was ligated into EcoRI cut λGT10, packaged and plated on $E.$ $coli$ c600hfl. About 3,000,000 clones from 1 µg of poly(A)+ RNA were plated on 50 150 mm petri dishes and hybridization screened with a 300 bp HinfI fragment from the 5' end of exon B. 46 duplicate positives were identified and analyzed by EcoRI digestion. Several cDNA inserts appeared to extend about 2500 bp 5' of primer 3. These long clones were analyzed by DNA sequencing. The sequences of the 5' ends of λ13.2 and λ13.27 are shown in FIG. 10. They possessed several features which indicated that we had reached the 5' end of the coding region for factor VIII. The initial 109 bp contained stop codons in all possible reading frames. Then appeared an ATG triplet followed by an open reading frame for the rest of the 2724 bp of the cDNA insert in λ13.2. Translation of the sequence following the initiator ATG gives a 19 amino acid sequence typical of a secreted protein "leader" or "pre" sequence (69). Its salient features are two charged residues bordering a 10 amino acid hydrophobic core. Following this putative leader sequence is a region corresponding to amino terminal residues obtained from protein sequence analysis of 210 kD and 95 kD thrombin digest species of factor VIII.

c. Oligo(dT) primed cDNA clones

Several thousand more 3' bases of factor VIII mRNA remained to be converted into cDNA. The choice was to prime reverse transcription with oligo(dT) and search for cDNA clones containing the 3' poly(A)+ tails of mRNA. However, in an effort to enrich the clones and to increase the efficiency of second strand DNA synthesis, established procedures were replaced with employment of a specific primer of second strand cDNA synthesis. The 16-mer primer 4, 5'-TATTGCTGCAGTGGAG, was synthesized to represent message sense sequence at a PstI site about 400 bp upstream of the 3' end of exon A (FIG. 9). mRNA was reverse transcribed with oligo(dT) priming, primer 4 was added with DNA polymerase for second strand synthesis, and EcoRI adapted cDNA then ligated into λGT10 as before. 3,000,000 plaques were screened with a 419 bp PstI/HincII fragment contained on p3.12, lying downstream from primer 4. DNA was prepared from the four clones recovered. These were digested, mapped, and blot hybridized with further downstream genomic fragments which had just been identified as exons using SV40 exon expression plasmids described above. Three of the four recombinants hybridized. The longest, λ10.44, was approximately 1,800 base pairs. The DNA sequence of λ10.44 showed that indeed second strand synthesis began at primer 4. It contained all exon sequences found in the SV40 exon expression clone S36 and more. However, the open reading frame of λ10.44 continued to the end of the cDNA. No 3' untranslated region nor poly(A) tail was found. Presumably second strand synthesis had not gone to completion.

To find clones containing the complete 3' end, we rescreened the same filters with labeled DNA from λ10.44. 24 additional clones were recovered and mapped, and the two longest (λ10.3 and λ10.9.2) were sequenced. They contained essentially identical sequences which overlapped λ10.44 and added about 1900 more 3' base pairs. 51 base pairs beyond the end of the λ10.44 terminus, the DNA sequence showed as TGA translation stop codon followed by an apparent 3' untranslated region of 1805 base pairs. Diagnostic features of this region are stop codons dispersed in all three reading frames and a poly(A) signal sequence, AATAAA 189), followed 15 bases downstream with a poly(A) stretch at the end of the cDNA (clone λ10.3 contains 8 A's followed by the EcoRI adapter at this point, while λ10.9.2 contains over 100 A's at its 3' end).

d. Complete cDNA Sequence

The complete sequence of overlapping clones is presented in FIG. 10. It consists of a continuous open reading frame coding for 2351 amino acids. Assuming a putative terminal signal peptide of 19 amino acids, the "mature" protein would therefore have 2332 amino acids. The calculated molecular weight for this protein is about 267,000 daltons. Taking into account possible glycosylation, this approximates the molecular weight of native protein as determined by SDS polyacrylamide gel electrophoresis.

The "complete" cDNA length of about 9000 base pairs (depending on the length of 3' poly(A)) agrees with the estimated length of the mRNA determined by Northern blot hybridization. The 5' (amino terminal coding) region contains substantial correspondence to the peptide sequence of 210 kD derived factor VIII material and the 3' (carboxy terminal coding) region contains substantial correspondence to the peptide sequence of 80 kD protein.

8. Expression of Recombinant Factor VIII a. Assembly of full length clone

In order to express recombinant Factor VIII, the full 7 kb protein coding region was assembled from several separate cDNA and genomic clones. We describe below and in FIG. 11 the construction of three intermediate plasmids containing the 5', middle, and 3' regions of the gene. The intermediates are combined in an expression plasmid following an SV40 early promoter. This plasmid in turn serves as the starting point for various constructions with modified terminal sequences and different promoters and selectable markers for transformation of a number of mammalian cell types.

The 5' coding region was assembled in a pBR322 derivative in such a way as to place a ClaI restriction site before the ATG start codon of the Factor VIII signal sequence. Since no other ClaI site is found in the gene, it becomes a convenient site for refinements of the expression plasmid. The convenient ClaI and SacI containing plasmid pT24-10 (67a) was cleaved with HindIII, filled in with DNA polymerase, and cut with SacI. A 77 b AluI/SacI was recovered from the 5' region of the Factor VIII cDNA clone λ13.2 and ligated into this vector to produce the intermediate called pF8Cla-Sac. (The AluI site is located in the 5' untranslated region of Factor VIII and the SacI site 10 b beyond the initiator ATG at nucleotide position 10 in FIG. 10; the nucleotide position of all restriction sites to follow will be numbered as in FIG. 10 beginning with the A of the initiator codon ATG.) An 85 b ClaI/SacI fragment containing 11 bp of adaptor sequence (the adaptor sequence 5' ATCGATAAGCT is entirely derived from pBR322) was isolated from pF8Cla-Sac and ligated along with an 1801 b SacI/KpnI (nucleotide 1811) fragment from λ13.2 into a ClaI/KpnI vector prepared from a pBR322 subclone containing a HindIII fragment (nuc. 1019–2277) of Factor VIII. This intermediate, called pF8Cla-Kpn, contained the initial 2277 coding nucleotides of Factor VIII preceded by 65 5' untranslated base pairs and the 11 base pair ClaI adapter sequence. pF8Cla-Kpn was opened with KpnI and SphI (in the pBR322 portion) to serve as the vector fragment in a ligation with a 466 b KpnI/HindIII fragment derived from an EcoRI subclone of λ13.2 and a 1654 b HindIII/SphI (nuc. 4003) fragment derived from the exon B containing subclone p222.8. This produced pF8Cla-Sph containing the first 3931 b of Factor VIII coding sequence.

The middle part of the coding region was derived from a three-piece ligation combining fragments of three pBR322/cDNA clones or subclones. p3.48 was opened with BamHI (nuc. 4743) and SalI (in pBR322 tet region) to serve as vector. Into these sites were ligated a 778 b BamHI/NdeI (nuc. 5520) fragment from p3.12 and a 2106 b NdeI/SalI (in pBR322) fragment from the subclone pλ10.44R1.9. Proper ligation resulted in a tetracycline resistant plasmid pF8Sca-RI.

The most 3' portion of Factor VIII cDNA was cloned directly into an SV40 expression vector. The plasmid pCVS-VEHBV contains an SV40 early promoter followed by a polylinker and the gene for the Hepatitis B surface antigen.

[pCVSVEHBV, also referred to as pCVSVEHBS, is a slight variant of p342E (73). In particular, pCVSVEHBV was obtained as follows: The 540 bp HindIII-HindIII fragment encompassing the SV40 origin of replication (74) was ligated into plasmid pML (75) between the EcoRI site and the HindIII site. The plasmid EcoRI site and SV40 HindIII site were made blunt by the addition of Klenow DNA polymerase I in the presence of the 4 dNTPs prior to digestion with HindIII. The resulting plasmid, pESV, was digested with HindIII and BamHI and the 2900 b vector fragment isolated. To this fragment was ligated a HindIII-BglII fragment of 2025 b from HBV modified to contain a polylinker (DNA fragment containing multiple restriction sites) at the EcoRI site. The HBV fragment encompasses the surface antigen gene and is derived by EcoRI-BglII digestion of cloned HBV DNA (74). The double stranded linker DNA fragment (5'dAAGCTTATCGATTCTAGAATTC3' ...) was digested with HindIII and EcoRI and added to the HBV fragment, converting the EcoRI-BglII fragment to a HindIII-BglII fragment. Although this could be done as a 3 part ligation consisting of linker, HBV fragment, and vector, it is more convenient and was so performed to first add the HindIII-EcoRI linker to the cloned HBV DNA and then excise the HindIII-BglII fragment by codigestion of the plasmid with those enzymes. The resulting plasmid, pCVSVEHBV, contains a bacterial origin of replication from the pBR322 derived pML, and ampicillin resistance marker, also from pML, an SV40 fragment oriented such that the early promoter will direct the transcription of the inserted HBV fragment, and the surface antigen gene from HBV. The HBV fragment also provides a polyadenylation signal for the production of polyadenylated mRNAs such as are normally formed in the cytoplasm of mammalian cells.]

The plasmid pCVSVEHBV contained a useful ClaI site immediately 5' to an XbaI site in the polylinker. This plasmid was opened with XbaI and BamHI (in the Hepatitis Ag 3' untranslated region) and the ends were filled in with DNA polymerase. This removed the Hepatitis surface antigen coding region but retained its 3' polyadenylation signal region, as well as the SV40 promoter. Into this vector was ligated a 1883 b EcoRI fragment (with filled in ends) from the cDNA clone λ10.3. This contained the final 77 coding base pairs of Factor VIII, the 1805 b 3' untranslated region, 8 adenosine residues, and the filled in EcoRI adaptor. By virtue of joining the filled in restriction sites, the EcoRI end was recreated at the 5' end (from filled in XbaI joined to filled in EcoRI) but destroyed at the 3' end (filled in EcoRI joined to filled in BamHI). This plasmid was called pCVSVE/10.3.

The complete factor VIII cDNA region was joined in a three-piece ligation. pCVSVE/10.3 was opened with ClaI and EcoRI and served as vector for the insertion of the 3870 b ClaI/ScaI fragment from pF8Cla-Sca and the 3182 b ScaI/EcoRI fragment from pF8Sca-RI. This expression plasmid was called pSVEFVIII.

b. Construction for Expression of Factor VIII in Tissue Culture Cells

A variant vector based on PSVEFVIII, containing the adenovirus major late promoter, tripartide leader sequence, and a shortened Factor VIII 3'-untranslated region produced active factor VIII when stably transfected into BHK cells.

FIG. 12 shows the construction of pAML3P.8cl, the expression plasmid that produces active factor VIII. To make this construction first the SstII site in pFD11 (49r) and the ClaI site in pEHED22 (49y) were removed with Klenow DNA polymerase I. These sites are in the 3' and 5' untranslated regions of the DHFR gene on these plasmids. Then a three-part ligation of fragments containing the deleted sites and the hepatitis B surface antigen gene from pCVSVEHBS (supra) was performed to generate the vector pCVSVEHED22ΔCS which has only one ClaI and one SstII site. The plasmid pSVEFVIII containing the assembled factor VIII gene (FIG. 11) was cleaved with ClaI and HpaI to excise the entire coding region and about 380 b of the 3' untranslated region. This was inserted into the ClaI, SstII deletion vector at its unique ClaI and HpaI sites, replacing the surface antigen gene to give the expression plasmid pSVE.8c1D.

Separately, the adenovirus major late promoter with its tripartite 5' leader was assembled from two subclones of portions of the adenovirus genome along with a DHFR expression plasmid, pEHD22 (49y). Construction of the two adenovirus subclones, pUCHSX and pMLP2, is described in the methods. pMLP2 contains the SstI to HindIII fragment from adenovirus coordinates 15.4 to 17.1 cloned in the SstI to HindIII site of pUC13 (59). pUCHSX contains the HindIII to XhoI fragment coordinates 17.1 to 26.5 cloned in the HindIII to SalI site of pUC13. When assembled at the HindIII site, these two adenovirus fragments contain the major late promoter of adenovirus, all of the first two exons and introns, and part of the third exon up to the XhoI site in the 5' untranslated region.

A three-part ligation assembled the adenovirus promoter in front of the DHFR gene in the plasmid pAML3P.D22. This put a ClaI sit shortly following the former XhoI site in the third exon of the adenovirus tripartite 5' leader. Finally, the SV40 early promoter of the factor VIII expression plasmid, pSVE.8c1D, was removed with ClaI and SalI and replaced with the adenovirus promoter to generate the final expression plasmid, pAML3P.8c1 (see FIG. 12). This plasmid contains the adenovirus tripartite leader spliced in the third exon to the 5' untranslated region of factor VIII. This is followed by the full length Factor VIII structural gene including its signal sequence. The 3' untranslated region of the factor VIII gene is spliced at the HpaI site to the 3' untranslated region of Hepatitis B surface antigen gene. This is followed by the DHFR gene which has an SV40 early promoter and a Hepatitis 3' untranslated region conferring a functional polyadenylation signal.

The factor VIII expression plasmid, pAML3P.8c1, was cotransfected into BHK cells with the neomycin resistance vector pSVEneoBal6 (ATCC No. CRL 8544, deposited 20 April 1984). These cells were first selected with G418 followed by a selection with methotrexate.

Initial characterization of the Factor VIII RNA produced by the BHK cell line was performed by Northern analysis of poly(A)$^+$ cytoplasmic RNA by hybridization to a $^{32}$P-labeled Factor VIII DNA probe. This analysis shows a band approximately 9 kb in length. Based on hybridization intensities, this band is about 100 to 200 fold enriched when compared to the 9 kb band found in the CH-2 cell line.

9. Identification of Recombinant Factor VIII a. Radioimmune assay

Radioimmune assays were performed as described in the Methods on supernatants and lysed cells from the BHK Factor VIII producing cell line. Table 1 shows that the supernatants (which contain factor VIII activity) (See 96) also contain approximately equal amounts of the 210 kD (C10) and the 80 kD (C7F7) portions of Factor VIII as judged by these RIAs. Factor VIII can also be detected in the cell lysates by both RIAs. Control cell lines not expressing factor VIII produced RIA values of less than 0.001 units per ml.

TABLE 1

| Factor VIII RIA of BHK cell line transfected with pAML3P.8c1 | | |
| --- | --- | --- |
| | C10 | C7F7 |
| Cell Supernatant | | |
| Exp. 1 | 0.14 U/ml | 0.077 |
| Exp. 2 | 0.022 | 0.021 |
| Cell Lysate | 0.42 | 0.016 |
| Exp. 1 | | |

$I^{125}$ cpm bound were converted to units/ml with a standard curve based on dilutions of normal plasma. All values are significantly above background. Limits of detection were 0.005 U/ml for the CIO and 0.01 U/ml for the C7F7 assays.

b. Chromogenic Assay on BHK Cell Media

As is shown in Table 2, media from these cells generated an absorbance at 405 nm when tested in the Coatest assay. As described above, this assay is specific for factor VIII activity in the activation of factor X. Addition of monoclonal antibodies specific for factor VIII decreased the amount of factor $X_a$ generated as evidenced by the decrease in absorbance from 0.155 for the media to 0.03 for the media plus antibodies (after subtracting out the blank value). Therefore, the cells are producing an activity which functions in an assay specific for factor VIII activity and this activity is neutralized by antibodies specific for factor VIII.

Incubation of the media in the reaction mixture without the addition of the factor $IX_a$, factor X, and phospholipid did not result in an increase in the absorbance at 405 nm above the blank value. The observed activity is therefore not due to the presence of a nonspecific protease cleaving the substrate, and in addition neutralized by antibodies specific for factor VIII.

TABLE 2

Factor VIII Activity of BHK cell line determined by chromogenic assay[1].

| Sample | Absorbance at 405 nm | Absorbance at 405 nm (Control value subtracted). |
|---|---|---|
| Media | 0.193 | 0.155 |
| Buffer control[2] | 0.038 | (0.0) |
| Media + factor VIII antibody[3] | 0.064 | 0.030 |
| Buffer control[2] + factor VIII antibody | 0.034 | (0.0) |

[1]Reactions modified as follows: 50 μl each of $IX_a$/X/phospholipid, $CaCl_2$, and 1-100 diluted sample were incubated 10 minutes at 37° C. S2222 (50 μl was added and reaction terminated with 100 μl) of 50 percent acetic acid after 60 minutes at 37° C.
[2]Buffer used in place of sample was 0.05M Tris - HCl, pH 7.3, containing 0.2 percent bovine serum albumin.
[3]Antibody was a mixture of C8 and C7F7 (10 μg each). The media was preincubated 5 minutes prior to start of assay.

c. Chromatography of Media on Monoclonal Resin

Serum containing media containing factor VIII activity was chromatographed on the C8 monoclonal antibody (ATCC No. 40115, deposited 20 April 1984) column as described (supra). The eluted fractions were diluted 1:100 and assayed for activity. To 50 μl of the diluted peak fraction was added various monoclonal antibodies known to be neutralizing for plasma factor VIII activity. The results shown in Table 3 demonstrate that the factor VIII activity eluted from the column (now much more concentrated than the media) was also neutralized by these factor VIII antibodies.

TABLE 3

Chromogenic Assay[1] of Peak Fraction of Monoclonal Antibody Eluate

| Sample | Absorbance at 405 nM[1] |
|---|---|
| Peak Fraction[2] | 0.186 |
| Peak fraction plus factor VIII Antibody[3] | 0.060 |
| Buffer Control | 0.000 |
| Buffer Control plus factor VIII Antibody | 0.045 |

[1]Assay was performed as follows: 50 μl of diluted sample was incubated 5 minutes with 50 μl of $IX_a$/X/phospholipid solution at 37° C. The reaction was incubated with 50 μl of $CaCl_2$, and allowed to proceed 10 minutes at 37° C. The chromogenic substrate (50 μl) was added, and the reaction teminated by the addition of 100 μl of 50 percent acetic acid after 10 minutes.
[2]Peak fraction was diluted 1:100 in 0.05M Tris, pH 7.2, containing 0.15M NaCl for assays.
[3]Antibody was 10 μl of Symbiotic antibody added to the diluted sample and incubated 5 minutes at room temperature.

d. Coagulant Activity of Purified Factor VIII.

The activity detected in the cell media was purified and concentrated by passage over a C8 monoclonal resin (supra). The peak fraction was dialyzed against 0.05M imidazole, pH6.9, containing 0.15M NaCl, 0.02M glycine ethyl ester, 0.01M $CaCl_2$, and 10 percent glycerol in order to remove the elution buffer. The Activity peak fraction was assayed by coagulation analysis in factor VIII deficient plasma (Table 4). A fibrin clot was observed at 84 seconds. With no addition, the hemophilia plasma formed a clot in 104.0 seconds. Therefore, the eluted fraction corrected the coagulation defect in hemophilia plasma. Normal human plasma was diluted and assayed in the same manner. A standard curve prepared from this plasma indicated that the eluted fraction had approximately 0.01 units per milliliter of factor VIII coagulant activity.

TABLE 4

Coagulant Activity of Monoclonal Antibody Purified Factor VIII

| Sample | Clotting time (sec.) |
|---|---|
| Recombinant factor VIII[1a] | 86.5 |
| Recombinant factor VIII[1a] and C7F7 antibody | 101.3 |
| Control[2] | 101.3 |
| Recombinant factor VIII[1b] | 82.4 |
| Recombinant factor VIII[1b] and 10λ Synbiotic antibody | 110.6 |
| Control[2] | 95.5 |

[1]Factor VIII was peak fraction eluted from the C8 monoclonal resin and dialyzed for 1½ (1a) or 2 (1b) hours in order to remove elution buffer.
[2]Control buffer was 0.05M Tris, pH 7.3, containing 0.2 percent bovine serum albumin.

e. Thrombin Activation of Purified Factor VIII.

Activation of coagulant activity by thrombin is a well established property of factor VIII. The eluted fraction from the monoclonal column was analyzed for this property. After dialysis of the sample to remove the elution buffer (supra), 100 μl of the eluate was diluted with 100 μl of 0.05M imidazole, pH7.6, containing 0.15M NaCl, 0.02M glycine ethyl ester, 0.01M $CaCl_2$ and 10 percent glycerol. This dilution was performed to dilute further any remaining elution buffer (which might interfere with thrombin functioning) as well as to increase the pH of the reaction mixture. Thrombin (25 ng) was added to the solution and the reaction was performed at room temperature. Aliquots of 25 μl were removed at various time points, diluted 1:3, and assayed for coagulation activity. The results are shown in FIG. 17. The factor VIII activity increased with time, and subsequently decreased, as expected for a factor VIII activity. The amount of thrombin added did not clot factor VIII deficient plasma in times observed for these assays, and the observed time dependent increase and subsequent decrease in observed coagulation time proved that the activity being monitored was in fact due to thrombin activation of factor VIII. The observed approximately 20-fold activation by thrombin is in agreement with that observed for plasma factor VIII.

f. Binding of Recombinant Factor VIII to Immobilized von Willebrand Sepharose.

Factor VIII is known to circulate in plasma in a reversible complex with von Willebrand Factor (vWF) (10–20). A useful form of recombinant factor VIII should therefore also possess this capacity for forming such a complex in order to confirm identity as factor VIII. In addition, the ability to form such a complex would prove the ability of a recombinant factor VIII to form the natural, circulating form of the activity as the factor VIII/vWF complex upon infusion into hemophiliacs. In order to test the ability of recombinant factor VIII to interact with vWF, vWF was purified and immobilized on a resin as follows:

Human von Willebrand factor was prepared by chromatography of human factor VIII concentrates (purchased from, e.g., Cutter Laboratories) on a Sepharose CL4B resin equilibrated with 0.05M Tris, pH 7.3, containing 0.15M NaCl. The von Willebrand factor elutes at the void volume of the column. This region was pooled, concentrated by precipitation with ammonium sulfate at 40 percent of saturation and re-chromatographed on the column in the presence of the above buffer containing 0.25M CaCl$_2$ in order to separate the factor VIII coagulant activity from the von Willebrand factor. The void volume fractions were again pooled, concentrated using ammonium sulfate, and dialyzed against 0.1M sodium bicarbonate. The resulting preparation was covalently attached to cyanogen bromide activated Sepharose (purchased from Pharmacia) as recommended by the manufacturer. The column was washed with 0.02M Tris, pH 7.3, containing 0.05M NaCl and 0.25M CaCl$_2$ in order to remove unbound proteins. The recombinant factor VIII was prepared in serum free media and applied to a 1.0 ml column of the vWF resin at room temperature.

The column was washed to remove unbound protein and eluted with 0.02M Tris, pH 7.3, containing 0.05M NaCl and 0.25M CaCl$_2$. Fractions of 1.0 ml were collected, diluted 1:10 and assayed. The results are shown in Table 5. The factor VIII activity is absorbed from the media onto the column. The activity can subsequently be eluted from the column using high salt (Table 5), as expected for the human factor VIII. Therefore, the factor VIII produced by the BHK cells has the property of specific interaction with the von Willebrand factor protein.

TABLE 5

| Sample | Absorbance at 405 nm |
| --- | --- |
| Cell Media | 0.143 |
| Wash | 0.075 |
| Eluted Fractions | |
| 1 | 0.000 |
| 2 | 0.410 |
| 3 | 0.093 |
| 4 | 0.017 |
| 5 | 0.000 |
| 6 | 0.000 |

[1]Assay procedures were that recommended by the manufacturer, except that all volumes were decreased by one half.

10. Analysis of Fusion Proteins

The purpose of this set of experiments was to prove immunological identity of the protein encoded by the clone with the polypeptides in plasma. This was accomplished by expressing portions of the gene as fusion proteins in *E. coli*. All or part of the coding sequences of the cloned gene can be expressed in forms designed to provide material suitable for raising antibodies. These antibodies, specific for desired regions of the cloned protein, can be of use in analysis and purification of proteins. A series of *E. coli*/factor VIII "fusion proteins" were prepared for this purpose. Fragments of factor VIII clones were ligated into the BglII site of the plasmid pNCV (70) in such a way as to join factor VIII coding sequences, in proper reading frame, to the first 12 amino acids of the fused *E. coli* trp LE protein (48, 70, 71). Substantial amounts of recombinant protein product are usually produced from this strong trp promoter system.

pfus1 was constructed by isolating a 189 bp StuI/HincII fragment of factor VIII (coding for amino acids 1799–1860) and ligating this into the SmaI site of pUC13 (49K). This intermediate plasmid was digested with BamHI and EcoRI and the 200 bp fragment inserted into pNCV (70) from which the 526 bpBglII to EcoRI fragment had been removed. This plasmid, pfus1, produces under trp promoter control a 10 kD fusion protein consisting of 16 trpLE and linker coded amino acids, followed by 61 residues of factor VIII and a final 9 linker coded and trpE carboxy terminal residues.

pfus3 was constructed by removing a 290 bp AvaII fragment of factor VIII (amino acids 1000–1096), filling in the overhanging nucleotides using Klenow fragment of DNA polymerase, and ligating this now blunt-ended DNA fragment into pNCV which had been cut with BglII and similarly filled in. This plasmid, with the filled in fragment in the proper orientation (as determined by restriction digests and DNA sequence analysis), directs the synthesis of an approximately 40 kD fusion protein containing 97 amino acids of factor VIII embedded within the 192 amino acid trpLE protein.

pfus4 was made by cutting a factor VIII subclone, λ222.8, with BanI, digesting back the overhang with nuclease S$_1$, followed by PstI digestion and isolation of the resulting 525 bp blunt/PstI fragment (amino acids 710–885). This was ligated into pNCV, which had been digested with BglII, treated with S$_1$, digested with PstI, and the vector fragment isolated. pfus4 directs the synthesis of a 22 kD fusion protein containing 175 amino acids of factor VIII following the initial 12 amino acids of trpLE.

The fusion proteins were purified and injected into rabbits in order to generate antibodies as described Supra. These antibodies were tested for binding to plasma derived factor VIII by Western Blot analysis.

The results of such a Western transfer are shown in FIG. 13. Each of the fusion proteins reacts with the plasma factor VIII. Fusion 1 was generated from the region of the gene encoding an 80,000 dalton polypeptide. It can be seen that fusion 1 antisera react only with the 80,000 dalton band, and do not react with the proteins of higher molecular weight. Fusion 3 and 4 antisera show cross reactivity with the proteins of greater than 80,000 daltons, and do not react with the 80,000 dalton band. The monoclonal antibody C8 is an activity neutralizing monoclonal directed against factor VIII and is known to react with the 210,000 dalton protein. FIG. 14 demonstrates that fusion 4 protein will react with this monoclonal antibody, thereby demonstrating that the amino acid sequence recognized by C8 is encoded by fusion 4 polypeptide. This further supports the identity of fusion 4 protein containing protein sequences encoding the 210,000 dalton protein. The above studies conclusively prove that the gene encodes the amino acid sequence for both the 210,000 and 80,000 dalton proteins.

11. Pharmaceutical Compositions

The compounds of the present invention can be formulated according to known methods to prepare pharmaceutically useful compositions, whereby the human factor VIII product hereof is combined in admixture with a pharmaceutically acceptable carrier vehicle. Suitable vehicles and their formulation, inclusive of other human proteins, e.g. human serum albumin, are described for example in Remington's *Pharmaceutical Sciences* by E. W. Martin, which is hereby incorporated by reference. Such compositions will contain an effective amount of the protein hereof together with a suitable amount of vehicle in order to prepare pharmaceutically acceptable compositions suitable for effective administration to the host. For example, the human factor VIII hereof may be parenterally administered to subjects suffering, e.g., from hemophilia A.

The average current dosage for the treatment of a hemophiliac varies with the severity of the bleeding episode. The average doses administered intraveneously are in the range of: 40 units per kilogram for pre-operative indications, 15 to 20 units per kilogram for minor hemorrhaging, and 20 to 40 units per kilogram administered over an 8-hours period for a maintenance dose.

Bibliography

1. *Hemostasis and Thrombosis*, Bloom and Thomas, Eds., Churchill, Livingstone, N.Y. (1981).
2. Davie, et al., *Ann. Rev. Biochem.* 44, 799 (1975).
3. Jackson, et al., *Ann. Rev. Biochem.* 49, 767 (1980).
4. Wright, J. *Am. Med. Assoc.* 170, 325 (1959).
5. Schmer, et al., *J. Biol. Chem.* 247, 2512 (1972).
6. Legaz, et al., *J. Biol. Chem.* 248, 3946 (1973).
7. Shapiro, et al., *J. Clin. Invest.* 52, 2198 (1973).
8. Nilsson, et al., *Acta. Med Scand.* 159, 179 (1957).
9. McKee, *Ann. NY Acad. Sci.* 240, 8 (1975).
10. Thelin, et al., *Arch. Biochem. Biophs.* 95, 70 (1961).
11. Griggs, et al., *Proc. Natl. Acad. Sci.* 70, 2814 (1973).
12. Donati, et al., *Thromb. Res.* 2, 97 (1973).
13. Weiss, et al., *Br. J. Haematol* 18, 89 (1970).
14. Weiss, et al., *Thromb. Diath. Haemorrh* 27, 212 (1972).
15. Weiss, et al., *Science* 182, 1149 (1973).
16. Rick, et al., *Blood* 42, 737 (1973).
17. Rick, et al., *Thromb. Res.* 7, 909 (1975).
18. Thelin, et al., *Arch. Biochem. Biophys.* 95, 70 (1961).
19. Owen, et al., *Thromb. Diath. Haemorrh.* 27, 502 (1972).
20. Cooper, et al., *Proc. Natl. Acad. Sci.* 70, 2326 (1973).
21. Vehar, et al., *Biochemistry* 19, 401 (1980).
22. Fulcher, et al., *Proc. Natl. Acad. Sci.* 79, 1648 (1982).
23. Fulcher, et al., *Blood* 61, 807 (1983).
24. Fulcher, et al., *Blood* 63, 486 (1984).
25. Fass, et al., *Blood* 59, 594 (1982).
26. Knutson, et al., *Blood* 59, 615 (1982).
27. Fay, et al., *Proc. Natl. Acad. Sci.* 79, 7200 (1982).
28. Gordon, et al., *Thrombosis Res.* 6, 127 (1975).
29. Sacharski, et al., *Mayo Clinic Proc.* 44, 784 (1969).
30. Green, et al., *Blood* 37, 47 (1971).
31. Schwinn, et al., U.S. Pat. No. 4,067,964.
31a. Zimmerman, et al., *Haemostasis and Thrombosis*, Bloom and Thomas, Eds., Churchill, Livingstone, N.Y., p.111 (1981).
32. Bolivar, et al., *Gene* 2, 95 (1977).
33. Chang, et al., *Nature* 275, 615 (1978).
34. Itakura, et al., *Science* 198, 1056 (1977).
35. Goeddel, et al., *Nature* 281, 544 (1979).
36. Goeddel, et al., *Nucleic Acids Res.* 8, 4057 (1980).
37. European Patent Appln. Publ. No. 0036776.
38. Siebenlist, et al., *Cell* 20, 269 (1980).
39. Stinchcomb, et al., *Nature* 282, 39 (1979).
40. Kingsman, et al., *Gene* 7, 141 (1979).
41. Tschemper, et al., *Gene* 10, 157 (1980).
42. Jones, *Genetics* 85, 12 (1977).
43. Hitzeman, et al., *J. Biol. Chem.* 255, 2073 (1980).
44. Hess, et al., *J. Adv. Enzyme Res.* 7, 149 (1968).
45. Holland, et al., *Biochemistry* 17, 4900 (1978).
46. Graham, et al., *Virology* 52, 546 (1978).
47. Cohen, et al., *PNAS (USA)* 69, 2110 (1972).
47a. Crea, et al., *Nucleic Acids Res.*, 2331 (1980)
47b. Beaucage, et al., *Tetrahedron Lett.* 22, 1859 (1981)
48. Maniatis, et al., *Molecular Cloning: A Laboratory Manual*, Cold Spring Harbor Laboratory, Cold Spring Harbor, N.Y. (1982).
48a. Lawn, et al., *Nucleic Acids Res.* 9, 1045 (1981).
49. Karn, et al., *Proc. Natl. Acad. Sci. USA* 77, 5172 (1980).
49a. Southern, *J. Molec. Biol.* 98, 503 (1975).
49b. Goldberg, *Proc. Natl. Acad. Sci. USA* 77, 5794 (1980).
49c. Taylor, et al., *Biochem. biophys. Acta* 442, 324 (1976).
49f. Ullrich, et al., *Science* 196, 1313 (1977).
49g. Berger, et al., *Biochemistry* 18, 5143 (1979).
49h. Aviv, et al., *Proc. Natl. Acad. Sci. USA* 69, 1408 (1972).
49i. Sanger, et al., *Proc. Natl. Acad. Sci. USA* 74, 5463 (1977).
49j. Gingeras, et al., *J. Biol. Chem.* 257 13475 (1982).
49k. Norrander, et al., *Gene* 26, 101 (1983).
49l. Picken, et al., *Inf. and Immun.* 42, 269 (1983).
49m. Beck, et al., *Gene* 19, 327 (1982).
49n. Simonson, et al., *Mol. Cell Biol.*, 3, 2250 (1983).
49o. Southern, et al., *Mol. and Applied Gen.* 1, 327 (1982).
49p. Graham, et al., *Virology* 52, 456 (1978).
49q. Wiglet, et al., *Proc. Natl. Acad. Sci. USA* 77, 3567 (1980).
49r. Simonson, et al., *Proc. Natl. Acad. Sci. USA* 80, 2495 (1983).
49s. Rotblat, et al., *Thromb. Res.* 21, 431 (1981).
49t. Rotblat, et al., *J. Lab. Clin. Med.* 101, 736 (1983).
49u. Kearney, et al., *J. Immun.* 123, 1548 (1979).
49v. Kohler, et al., *Nature* 256, 495 (1975).
49w. Benton, et al., *Virol.* 117, 490 (1982).
49x. Chalon, et al., *J. Immun.* 9, 359 (1979).
49y. U.S. Ser. No. 459152, filed 19 Jan. 1983.
50. Ish-Horowitz, et al., *Nucl. Acids Res.*, 9, 2989 (1981).
51. Stel, et al., *Nature* 303, 530 (1983).
52. Kelly, et al., *Brit. J. Haem.* (1984).
53. Exmer, et al., *Thrombosis Res.* 32, 427 (1983).
54. Jaffe, et al., *J. Clin. Invest.* 53, 36a (1974).
55. Fay, et al., *Proc. Natl. Acad. Sci. USA* 79, 7200 (1982).
56. Zimmerman, et al., *Haemostasis and Thrombosis* Bloom, A. L. and Duncan, P. T. (Churchill Livinstone, New York) pp. 111–123 (1981).
56a. Meili, et al., *Thromb. Diathes. Haemorrh.* 24, 161 (1970).
57. Grantham, et al., *Nuclei Arts Res.* 8, r49 (1980).
58. Kurachi, et al., *Proc. natl. Acad. Sci. USA* 79, 6461 (1982).
59. Viera, et al., *Gene* 19, 259 (1982).
60. Breathnach, et al., *Ann. Rev. Biochem* 50, 349 (1981).
61. Sharp, *Cell* 23, 643 (1981).
62. Fritsch, et al., *Cell* 19, 959 (1980).
63. Collins, et al., *Proc. Natl. Acad. Sci. USA* 75, 4242 (1978).
66. Kafatos, et al., *Nucleic Acids Res.*, 7,1541 (1979).
67. Capon, et al., *Nature* 304, 507 (1983).
67a. Capon, et al., *Nature* 301, 33 (1983).
68. Huynh, et al., *Practical Approaches in Biochemistry* (IRL Press Ltd., Oxford, England) (1984).
69. Perlman, et al., *J. Mol. Biol.* 167, 391 (1983).
70. Kleid, et al., *Science* 214, 1125 (1981).
71. Goeddel, et al., *Nature* 87, 411 (1980).
73. Crowley, et al., *Mol. Cell Biol.* 3, 44 (1983).
74. Liu, et al., *DNA* 1, 213 (1982).
75. Lusky, et al., *Nature* 293, 79 (1981).
76. Hanahan, *J. Mol. Biol.* 166, 557 (1983).
77. Gluzman *Cell* 23, 175 (1981).
78. Grunstein, et al., *Proc. Natl. Acad. Sci. USA* 72, 3961 (1975).
79. Tuddenham, et al., *Symposium on Factors VIII/von Willebrand Factor*, October 7–9, 1982, p.1.

80. Morrissey, *Anal. Bioclem* 117, 307 (1981).
81. Laemmli, *Nature* 227, 680 (1970).
82. Greenwood, et al., *Biochem. J.* 89, 114 (1963).
83. Maniatis, et al., *Cell* 15, 687 (1963).
84. Sompayrac. et al., *Proc. Natl. Acad. Sci. USA* 78, 7575 (1981).
86. Messing, et al., *Nucl. Acids Res.* 9, 304 (1981).
87. Wood, et al., *J. Biol. Chem.* 256, 1502 (1981).
88. Shen, et al., *Cell* 19, 379 (1981).
89. Proudfoot, et al., *Nature* 252, 359 (1976).

We claim:

1. A recombinant DNA vector which expresses exons of genomic DNA fragments inserted into the vector, which vector comprises: (1) a promoter operably linked to a splice donor site followed by a splice acceptor site and (2) a genomic DNA fragment inserted between said splice donor and splice acceptor sites, wherein the genomic DNA fragment comprises a splice acceptor site followed by a splice donor site, and wherein said vector, upon transcription in a transfected eukaryotic cell culture, expresses the corresponding RNA segment of said genomic DNA fragment free of any intron.

2. The vector of claim 1 wherein the genomic DNA fragment codes for a polypeptide of interest.

3. The vector of claim 2 wherein the polypeptide is human factor VIII.

4. A eukaryotic cell culture transfected with a vector according to claim 1.

5. pESVDA.

6. A eukaryotic cell culture transfected with a vector according to claim 5.

* * * * *

UNITED STATES PATENT AND TRADEMARK OFFICE
CERTIFICATE OF CORRECTION

PATENT NO. : 5,683,905

DATED : November 4, 1997

INVENTOR(S) : Daniel J. Capon et al.

It is certified that error appears in the above-identified patent and that said Letters Patent is hereby corrected as shown below:

On the title page, after item [73] insert:

-- [*] The term of this patent shall not extend beyond the expiration date of Pat. No. 5,561,053.--

Signed and Sealed this

Twenty-seventh Day of January, 1998

*Attest:*

BRUCE LEHMAN

*Attesting Officer*    *Commissioner of Patents and Trademarks*